(12) United States Patent
Teufel et al.

(10) Patent No.: US 12,318,454 B2
(45) Date of Patent: *Jun. 3, 2025

(54) BICYCLIC PEPTIDE LIGANDS SPECIFIC FOR MT1-MMP

(71) Applicant: BicycleRD Limited, Cambridge (GB)

(72) Inventors: Daniel Paul Teufel, Cambridge (GB); Catherine Lucy Stace, Cambridge (GB); Silvia Pavan, Cambridge (GB); Edward Walker, Cambridge (GB); Leonardo Baldassarre, Cambridge (GB)

(73) Assignee: BicycleRD Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/315,869

(22) Filed: May 11, 2023

(65) Prior Publication Data

US 2024/0082410 A1    Mar. 14, 2024

Related U.S. Application Data

(60) Continuation of application No. 17/443,222, filed on Jul. 22, 2021, now Pat. No. 11,672,868, which is a continuation of application No. 16/705,446, filed on Dec. 6, 2019, now Pat. No. 11,103,591, which is a division of application No. 15/523,266, filed as application No. PCT/GB2015/053247 on Oct. 29, 2015, now Pat. No. 10,532,106.

(30) Foreign Application Priority Data

Oct. 29, 2014  (GB) ...................................... 1419237
Aug. 27, 2015  (GB) ...................................... 1515245

(51) Int. Cl.
| | | |
|---|---|---|
| *C07K 7/08* | (2006.01) | |
| *A61K 31/195* | (2006.01) | |
| *A61K 47/54* | (2017.01) | |
| *A61K 47/64* | (2017.01) | |
| *A61K 51/04* | (2006.01) | |
| *A61K 51/08* | (2006.01) | |
| *C07K 7/02* | (2006.01) | |
| *A61P 35/00* | (2006.01) | |

(52) U.S. Cl.
CPC ............ *A61K 47/64* (2017.08); *A61K 31/195* (2013.01); *A61K 47/547* (2017.08); *A61K 51/0482* (2013.01); *A61K 51/08* (2013.01); *C07K 7/02* (2013.01); *C07K 7/08* (2013.01); *A61P 35/00* (2018.01)

(58) Field of Classification Search
CPC .... A61K 47/64; A61K 31/195; A61K 47/547; A61K 51/0482; A61K 51/08; C07K 7/02; C07K 7/08; A61P 35/00
See application file for complete search history.

(56) References Cited

U.S. PATENT DOCUMENTS

| | | |
|---|---|---|
| 2,642,514 A | 6/1953 | Herkenhoff |
| 4,650,750 A | 3/1987 | Giese |
| 4,709,016 A | 11/1987 | Giese |
| 5,360,819 A | 11/1994 | Giese |
| 5,516,931 A | 5/1996 | Giese et al. |
| 5,595,756 A | 1/1997 | Bally et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 6,326,144 B1 | 12/2001 | Bawendi et al. |
| 6,468,808 B1 | 10/2002 | Nie et al. |
| 6,552,065 B2 | 4/2003 | Remiszewski et al. |
| 7,151,047 B2 | 12/2006 | Chan et al. |
| 7,192,785 B2 | 3/2007 | Nie et al. |
| 7,390,799 B2 | 6/2008 | Bruncko et al. |
| 8,138,347 B2 | 3/2012 | Knight et al. |
| 8,680,022 B2 | 3/2014 | Gregory et al. |
| 8,685,890 B2 | 4/2014 | Winter et al. |
| 8,778,844 B2 | 7/2014 | Winter et al. |
| 8,906,682 B2 | 12/2014 | June et al. |
| 8,986,655 B2 | 3/2015 | Weiss et al. |
| 9,518,081 B2 | 12/2016 | Winter et al. |
| 9,644,201 B2 | 5/2017 | Winter et al. |
| 9,657,288 B2 | 5/2017 | Winter et al. |

(Continued)

FOREIGN PATENT DOCUMENTS

| | | |
|---|---|---|
| CN | 101497878 A | 8/2009 |
| CN | 105307686 A | 2/2016 |

(Continued)

OTHER PUBLICATIONS

"Cholangiocarcinoma," Merck Manual. Accessed Mar. 12, 2017: http://surgery.usc.edu/divisions/tumor/pancreasdiseases/web%20pages/BILIARY%20SYSTEM/cholangiocarcinoma.

(Continued)

*Primary Examiner* — Julie Ha
*Assistant Examiner* — Kristina M Hellman
(74) *Attorney, Agent, or Firm* — Wolf, Greenfield & Sacks, P.C.

(57) ABSTRACT

The present invention relates to polypeptides which are covalently bound to molecular scaffolds such that two or more peptide loops are subtended between attachment points to the scaffold. In particular, the invention describes peptides which are high affinity binders of membrane type 1 metalloprotease (MT1-MMP). The invention also describes drug conjugates comprising said peptides, conjugated to one or more effector and/or functional groups which have utility in imaging and targeted cancer therapy.

13 Claims, 11 Drawing Sheets

Specification includes a Sequence Listing.

(56) References Cited

U.S. PATENT DOCUMENTS

| | | |
|---|---|---|
| 9,670,482 B2 | 6/2017 | Winter et al. |
| 9,670,484 B2 | 6/2017 | Winter et al. |
| 9,670,521 B2 | 6/2017 | Grabstein et al. |
| 9,868,767 B2 | 1/2018 | Pei et al. |
| 9,932,367 B2 | 4/2018 | Stace et al. |
| 9,994,617 B2 | 6/2018 | Tite et al. |
| 10,118,947 B2 | 11/2018 | Teufel et al. |
| 10,294,274 B2 | 5/2019 | Teufel et al. |
| 10,441,663 B2 | 10/2019 | Bennett et al. |
| 10,532,106 B2 | 1/2020 | Teufel et al. |
| 10,624,968 B2 | 4/2020 | Bennett et al. |
| 10,626,147 B2 | 4/2020 | Pei et al. |
| 10,792,368 B1 | 10/2020 | Teufel et al. |
| 10,800,813 B2 | 10/2020 | Tite et al. |
| 10,857,196 B2 | 12/2020 | Beswick et al. |
| 10,870,679 B2 | 12/2020 | Teufel et al. |
| 10,875,894 B2 | 12/2020 | Chen et al. |
| 10,894,808 B2 | 1/2021 | Teufel et al. |
| 10,899,798 B2 | 1/2021 | Bennett et al. |
| 10,919,937 B2 | 2/2021 | Beswick et al. |
| 10,994,019 B2 | 5/2021 | Teufel et al. |
| 11,103,591 B2 | 8/2021 | Teufel et al. |
| 11,180,531 B2 | 11/2021 | Beswick et al. |
| 11,261,214 B2 | 1/2022 | Chen et al. |
| 11,241,473 B2 | 2/2022 | Beswick et al. |
| 11,306,123 B2 | 4/2022 | Mudd et al. |
| 11,312,749 B2 | 4/2022 | Mudd et al. |
| 11,332,500 B2 | 5/2022 | Mudd et al. |
| 11,396,530 B2 | 7/2022 | Beswick et al. |
| 11,414,488 B2 | 8/2022 | Bennett et al. |
| 11,433,137 B2 | 9/2022 | Bennett et al. |
| 11,623,012 B2 | 4/2023 | Chen et al. |
| 11,672,868 B2 | 6/2023 | Teufel et al. |
| 11,696,956 B2 | 7/2023 | Chen et al. |
| 11,730,819 B2 | 8/2023 | Teufel et al. |
| 11,746,126 B2 | 9/2023 | Bennett et al. |
| 11,814,447 B2 | 11/2023 | Teufel et al. |
| 11,833,211 B2 | 12/2023 | Chen et al. |
| 11,912,792 B2 | 2/2024 | Beswick et al. |
| 11,946,041 B2 | 4/2024 | Chen et al. |
| 11,970,553 B2 | 4/2024 | Mudd et al. |
| 12,049,520 B2 | 7/2024 | Chen et al. |
| 2002/0164788 A1 | 11/2002 | Ellis et al. |
| 2005/0169931 A1 | 8/2005 | Kinch et al. |
| 2009/0222937 A1 | 9/2009 | Arnould et al. |
| 2009/0304721 A1 | 10/2009 | Kinch et al. |
| 2012/0101253 A1 | 4/2012 | Heinis et al. |
| 2012/0172235 A1 | 7/2012 | Winter et al. |
| 2013/0064791 A1 | 3/2013 | Poelstra et al. |
| 2013/0072598 A1 | 3/2013 | Yang et al. |
| 2014/0163201 A1 | 6/2014 | Winter et al. |
| 2014/0249292 A1 | 9/2014 | Tite et al. |
| 2014/0256596 A1 | 9/2014 | Tite et al. |
| 2014/0274759 A1 | 9/2014 | Walker et al. |
| 2015/0087810 A1 | 3/2015 | Moore et al. |
| 2015/0038434 A1 | 5/2015 | Yang et al. |
| 2016/0046721 A1 | 2/2016 | Qian et al. |
| 2016/0031939 A1 | 4/2016 | Stace et al. |
| 2016/0122430 A1 | 5/2016 | Gish et al. |
| 2016/0256579 A1 | 8/2016 | Shalom |
| 2016/0326232 A1 | 10/2016 | Rosa et al. |
| 2017/0067045 A1 | 3/2017 | Winter et al. |
| 2017/0190743 A1 | 7/2017 | Pei et al. |
| 2017/0204150 A1 | 7/2017 | Liu et al. |
| 2017/0304342 A1 | 10/2017 | Cox et al. |
| 2017/0306032 A1 | 10/2017 | Gehlsen |
| 2017/0360952 A1 | 12/2017 | Schwartz et al. |
| 2018/0169254 A1 | 6/2018 | Bennett et al. |
| 2018/0200378 A1 | 7/2018 | Bennett et al. |
| 2018/0318451 A1 | 8/2018 | Skerra et al. |
| 2018/0280525 A1 | 10/2018 | Teufel et al. |
| 2018/0311300 A1 | 11/2018 | Beswick et al. |
| 2018/0362585 A1 | 12/2018 | Teufel et al. |
| 2018/0371020 A1 | 12/2018 | Bennett et al. |
| 2019/0134213 A1 | 5/2019 | Teufel et al. |
| 2019/0184025 A1 | 6/2019 | Chen et al. |
| 2019/0263866 A1 | 8/2019 | Chen et al. |
| 2019/0307836 A1 | 10/2019 | Keen et al. |
| 2019/0389906 A1 | 12/2019 | Beswick et al. |
| 2019/0389907 A1 | 12/2019 | Teufel et al. |
| 2020/0129630 A1 | 4/2020 | Koehler et al. |
| 2020/0131228 A1 | 4/2020 | Beswick et al. |
| 2020/0171161 A1 | 6/2020 | Teufel et al. |
| 2020/0190213 A1 | 6/2020 | Preyer et al. |
| 2020/0215199 A1 | 7/2020 | Bennett et al. |
| 2020/0255477 A1 | 8/2020 | Chen et al. |
| 2020/0283482 A1 | 9/2020 | Keen et al. |
| 2020/0289657 A1 | 9/2020 | Teufel et al. |
| 2020/0291096 A1 | 9/2020 | Keen et al. |
| 2020/0316209 A1 | 10/2020 | Teufel et al. |
| 2020/0338203 A1 | 10/2020 | Chen et al. |
| 2020/0354406 A1 | 11/2020 | Stephen et al. |
| 2020/0354456 A1 | 11/2020 | Bennett et al. |
| 2020/0407709 A1 | 12/2020 | Chen et al. |
| 2021/0040154 A1 | 2/2021 | Mudd et al. |
| 2021/0046145 A1 | 2/2021 | Beswick et al. |
| 2021/0069287 A1 | 3/2021 | Mudd et al. |
| 2021/0079045 A1 | 3/2021 | Bennett et al. |
| 2021/0101932 A1 | 4/2021 | Chen et al. |
| 2021/0101933 A1 | 4/2021 | Chen et al. |
| 2021/0101937 A1 | 4/2021 | Mudd et al. |
| 2021/0122785 A1 | 4/2021 | Teufel et al. |
| 2021/0122804 A1 | 4/2021 | Teufel et al. |
| 2021/0147484 A1 | 5/2021 | Beswick et al. |
| 2021/0147485 A1 | 5/2021 | Teufel et al. |
| 2021/0261620 A1 | 8/2021 | Teufel et al. |
| 2021/0269480 A1 | 9/2021 | Beswick et al. |
| 2021/0299210 A2 | 9/2021 | Keen et al. |
| 2022/0023432 A1 | 1/2022 | Teufel et al. |
| 2022/0024982 A1 | 1/2022 | Chen et al. |
| 2022/0031858 A1 | 2/2022 | McDonnell et al. |
| 2022/0054646 A1 | 2/2022 | Chen et al. |
| 2022/0064218 A1 | 3/2022 | Baldassarre et al. |
| 2022/0064221 A1 | 3/2022 | Lani et al. |
| 2022/0072140 A1 | 3/2022 | Stace et al. |
| 2022/0088118 A1 | 3/2022 | Baldassarre et al. |
| 2022/0088207 A1 | 3/2022 | Chen et al. |
| 2022/0089643 A1 | 3/2022 | Beswick et al. |
| 2022/0119488 A1 | 4/2022 | Lani et al. |
| 2022/0133732 A1 | 5/2022 | Baldassarre et al. |
| 2022/0133733 A1 | 5/2022 | Baldassarre et al. |
| 2022/0135614 A1 | 5/2022 | Teufel |
| 2022/0184222 A1 | 6/2022 | Bennett et al. |
| 2022/0194983 A1 | 6/2022 | Teufel et al. |
| 2022/0213145 A1 | 7/2022 | Chen et al. |
| 2022/0227811 A1 | 7/2022 | Mudd et al. |
| 2022/0242911 A1 | 8/2022 | Mudd et al. |
| 2022/0257784 A1 | 8/2022 | Upadhyaya et al. |
| 2022/0281918 A1 | 8/2022 | Van Rietschoten et al. |
| 2022/0275053 A1 | 9/2022 | Upadhyaya et al. |
| 2022/0289792 A1 | 9/2022 | Chen et al. |
| 2022/0306689 A9 | 9/2022 | Chen et al. |
| 2022/0306694 A1 | 9/2022 | Mudd et al. |
| 2022/0362390 A1 | 11/2022 | Stace et al. |
| 2022/0387611 A1 | 12/2022 | Bennett et al. |
| 2023/0002596 A1 | 1/2023 | Zhang et al. |
| 2023/0008076 A1 | 1/2023 | Keen et al. |
| 2023/0025916 A1 | 1/2023 | Bennett et al. |
| 2023/0025971 A1 | 1/2023 | Bennett et al. |
| 2023/0165966 A1 | 1/2023 | Koehler et al. |
| 2023/0086865 A1 | 3/2023 | Balmford et al. |
| 2023/0129258 A1 | 4/2023 | Upadhyaya et al. |
| 2023/0106511 A1 | 6/2023 | Balmford et al. |
| 2023/0181749 A1 | 6/2023 | Dickson et al. |
| 2023/0220008 A1 | 7/2023 | Chen et al. |
| 2023/0233698 A1 | 7/2023 | Bennett et al. |
| 2023/0287047 A1 | 9/2023 | Beswick et al. |
| 2023/0340020 A1 | 10/2023 | Teufel et al. |
| 2023/0144799 A1 | 11/2023 | Chen et al. |
| 2024/0000957 A1 | 1/2024 | Chen et al. |
| 2024/0108738 A1 | 4/2024 | Keen et al. |
| 2024/0158444 A1 | 5/2024 | Bennett et al. |
| 2024/0173422 A1 | 6/2024 | Chen et al. |
| 2024/0189436 A1 | 6/2024 | Keen et al. |

(56) References Cited

U.S. PATENT DOCUMENTS

| | | |
|---|---|---|
| 2024/0240255 A1 | 6/2024 | Chen et al. |
| 2024/0197897 A1 | 7/2024 | Blakemore et al. |
| 2024/0325554 A1 | 10/2024 | Keen et al. |
| 2024/0336656 A1 | 10/2024 | Mudd et al. |

FOREIGN PATENT DOCUMENTS

| | | |
|---|---|---|
| EP | 2393520 A1 | 12/2011 |
| EP | 3192802 A1 | 7/2017 |
| EP | 2970954 B1 | 10/2018 |
| FR | 2932189 A1 | 12/2009 |
| GB | 1239978 A | 7/1971 |
| JP | 2006514104 A | 4/2006 |
| JP | 2011513298 A | 4/2011 |
| JP | 2011522794 A | 8/2011 |
| JP | 2013518807 A | 5/2013 |
| JP | 2016527180 A | 9/2016 |
| JP | 2018502825 A | 2/2018 |
| WO | WO-1997008320 A1 | 3/1997 |
| WO | WO9819705 A1 | 5/1998 |
| WO | WO0128683 A1 | 4/2001 |
| WO | WO-2001042246 A2 | 6/2001 |
| WO | WO-2002088112 A1 | 11/2002 |
| WO | WO-2003063794 A2 | 8/2003 |
| WO | WO-2004005348 A1 | 1/2004 |
| WO | WO-2004019973 A1 | 3/2004 |
| WO | WO-2004077062 A2 | 9/2004 |
| WO | WO-2004089925 A1 | 10/2004 |
| WO | WO-2004106328 A1 | 12/2004 |
| WO | WO-2005007623 A2 | 1/2005 |
| WO | WO-2005103083 A2 | 11/2005 |
| WO | WO-2005113554 A2 | 12/2005 |
| WO | WO2006029879 A2 | 3/2006 |
| WO | WO-2006078161 A1 | 7/2006 |
| WO | WO-2006078846 A1 | 7/2006 |
| WO | 2006101187 A1 | 9/2006 |
| WO | WO2006105021 A2 | 10/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO2007005874 A2 | 7/2007 |
| WO | WO-2007084786 A1 | 7/2007 |
| WO | WO-2007129161 A2 | 11/2007 |
| WO | WO-2008033561 A2 | 3/2008 |
| WO | WO-2008039218 A2 | 4/2008 |
| WO | WO2008134761 A2 | 6/2008 |
| WO | WO-2008109943 A1 | 9/2008 |
| WO | WO-2008118802 A1 | 10/2008 |
| WO | WO2008132601 A1 | 11/2008 |
| WO | WO-2008157490 A1 | 12/2008 |
| WO | WO2009009116 A2 | 1/2009 |
| WO | WO2009044273 A2 | 4/2009 |
| WO | WO2009073620 A2 | 6/2009 |
| WO | 2009097397 A2 | 8/2009 |
| WO | WO-2009098450 A2 | 8/2009 |
| WO | WO-2009114512 A1 | 9/2009 |
| WO | WO2010019570 A2 | 2/2010 |
| WO | WO2010077634 A1 | 7/2010 |
| WO | WO-2010089115 A1 | 8/2010 |
| WO | WO-2010089117 A1 | 8/2010 |
| WO | WO-2011018227 A2 | 2/2011 |
| WO | WO2011028683 A1 | 3/2011 |
| WO | WO2011056652 A1 | 5/2011 |
| WO | WO2011070024 A1 | 6/2011 |
| WO | WO-2011079015 A1 | 6/2011 |
| WO | WO-2011090760 A1 | 7/2011 |
| WO | WO2011107553 A1 | 9/2011 |
| WO | WO2011109400 A2 | 9/2011 |
| WO | WO2011131407 A1 | 10/2011 |
| WO | WO2011140249 A2 | 11/2011 |
| WO | WO2012032433 A1 | 3/2012 |
| WO | WO-2012057624 A1 | 5/2012 |
| WO | WO2012142237 A1 | 10/2012 |
| WO | WO2012145493 A1 | 10/2012 |
| WO | WO-2013050615 A1 | 4/2013 |
| WO | WO-2013050616 A1 | 4/2013 |
| WO | WO-2013050617 A1 | 4/2013 |
| WO | WO2013079174 A1 | 6/2013 |
| WO | WO2013087699 A1 | 6/2013 |
| WO | WO2013119716 A1 | 8/2013 |
| WO | WO2013132044 A1 | 9/2013 |
| WO | WO2013169264 A1 | 11/2013 |
| WO | WO2014008218 A1 | 1/2014 |
| WO | WO2014036357 A1 | 3/2014 |
| WO | WO-2014044872 A1 | 3/2014 |
| WO | WO2014063012 A1 | 4/2014 |
| WO | WO2014142237 A1 | 9/2014 |
| WO | WO-2014164693 A2 | 10/2014 |
| WO | WO-2014167122 A1 | 10/2014 |
| WO | WO2014190257 A2 | 11/2014 |
| WO | WO-2015116904 A1 | 8/2015 |
| WO | WO-2015171938 A1 | 11/2015 |
| WO | WO-2015179691 A2 | 11/2015 |
| WO | WO2016046574 A1 | 3/2016 |
| WO | WO-2016067035 A1 | 5/2016 |
| WO | WO2016050361 A1 | 7/2016 |
| WO | WO-2016171242 A1 | 10/2016 |
| WO | WO2016171272 A1 | 10/2016 |
| WO | WO-2016174103 A1 | 11/2016 |
| WO | WO2017046658 A1 | 3/2017 |
| WO | 2017102906 A1 | 6/2017 |
| WO | WO-2017161069 A1 | 9/2017 |
| WO | WO-2017173408 A1 | 10/2017 |
| WO | WO-2017182672 A1 | 10/2017 |
| WO | WO-2017191460 A1 | 11/2017 |
| WO | WO2017205738 A1 | 11/2017 |
| WO | WO-2018096365 A1 | 5/2018 |
| WO | WO-2018115203 A1 | 6/2018 |
| WO | WO-2018115204 A1 | 6/2018 |
| WO | WO2018222987 A1 | 6/2018 |
| WO | WO-2018127699 A1 | 7/2018 |
| WO | WO-2018156740 A1 | 8/2018 |
| WO | WO-2018197509 A1 | 11/2018 |
| WO | WO-2018197893 A1 | 11/2018 |
| WO | WO-2019002842 A1 | 1/2019 |
| WO | WO-2019025811 A1 | 2/2019 |
| WO | WO-2019034866 A1 | 2/2019 |
| WO | WO-2019034868 A1 | 2/2019 |
| WO | WO2019084060 A1 | 2/2019 |
| WO | WO-2019094395 A2 | 5/2019 |
| WO | WO-2019122860 A1 | 6/2019 |
| WO | WO-2019122861 A1 | 6/2019 |
| WO | WO-2019122863 A1 | 6/2019 |
| WO | WO-2019162682 A1 | 8/2019 |
| WO | WO-2019193328 A1 | 10/2019 |
| WO | WO2019136442 A1 | 11/2019 |
| WO | WO2019226617 A1 | 11/2019 |
| WO | WO-2019243313 A1 | 12/2019 |
| WO | WO2019243329 A1 | 12/2019 |
| WO | WO2019243353 A1 | 12/2019 |
| WO | WO2019243455 A1 | 12/2019 |
| WO | WO-2019243832 A1 | 12/2019 |
| WO | WO-2019243833 A1 | 12/2019 |
| WO | WO-2020084305 A1 | 4/2020 |
| WO | WO-2008089627 A1 | 5/2020 |
| WO | WO-2020089627 A1 | 5/2020 |
| WO | WO2020120980 A1 | 6/2020 |
| WO | WO-2020120981 A1 | 6/2020 |
| WO | WO-2020120983 A1 | 6/2020 |
| WO | WO-2020120984 A1 | 6/2020 |
| WO | WO-2020128526 A1 | 6/2020 |
| WO | WO2020128527 A1 | 6/2020 |
| WO | WO2020148525 A1 | 7/2020 |
| WO | WO2020148526 A1 | 7/2020 |
| WO | WO2020148527 A1 | 7/2020 |
| WO | WO2020148528 A1 | 7/2020 |
| WO | WO2020148529 A1 | 7/2020 |
| WO | WO2020148530 A1 | 7/2020 |
| WO | WO-2020165600 A1 | 8/2020 |
| WO | WO-2020178574 A1 | 9/2020 |
| WO | WO-2020201753 A1 | 10/2020 |
| WO | WO-2020225577 A1 | 11/2020 |

(56) References Cited

FOREIGN PATENT DOCUMENTS

| | | |
|---|---|---|
| WO | WO-2020229803 A1 | 11/2020 |
| WO | WO-2021019243 A1 | 2/2021 |
| WO | WO2021019244 A1 | 2/2021 |
| WO | WO-2021019245 A1 | 2/2021 |
| WO | WO2021019246 A1 | 2/2021 |
| WO | WO2021028686 A1 | 2/2021 |
| WO | WO2021171028 A1 | 2/2021 |
| WO | WO2021171029 A1 | 2/2021 |
| WO | WO2021038232 A1 | 4/2021 |
| WO | WO-2021064428 A1 | 4/2021 |
| WO | WO2021074622 A1 | 4/2021 |
| WO | WO-2021074647 A1 | 4/2021 |
| WO | WO-2021105694 A1 | 6/2021 |
| WO | WO2021148974 A1 | 7/2021 |
| WO | WO2021234391 A1 | 11/2021 |
| WO | WO-2021250418 A1 | 12/2021 |
| WO | WO-2022029420 A1 | 2/2022 |
| WO | WO2022038158 A1 | 2/2022 |
| WO | WO2022148969 A1 | 7/2022 |
| WO | WO2022148974 A2 | 7/2022 |
| WO | WO2022148975 A1 | 7/2022 |
| WO | WO2022148979 A1 | 7/2022 |
| WO | WO2023089308 A1 | 5/2023 |
| WO | WO2023031623 A2 | 9/2023 |

OTHER PUBLICATIONS

Adley et al., "Expression of membrane type 1 matrix metalloproteinase (MMP-14) in epithelial ovarian cancer: high level expression in clear cell carcinoma," Gynecol Oncol. Feb. 2009; 112(2):319-24.

Angelini et al., "Bicyclic peptide inhibitor reveals large contact interface with a protease target," ACS Chem Biol. May 18, 2012;7(5):817-21.

Augoff et al., "Upregulated expression and activation of membrane-associated proteases in esophageal squamous cell carcinoma," Oncol Rep. Jun. 2014; 31(6):2820-6.

Barbolina et al., "Microenvironmental regulation of membrane type 1 matrix metalloproteinase activity in ovarian carcinoma cells via collagen-induced EGR1 expression," J Biol Chem. Feb. 16, 2007;282(7):4924-4931.

Chandrasekar, "Bladder Cancer," Merck Manual. Modified Sep. 2022; Accessed Sep. 30, 2022: http://www.merckmanuals.com/home/kidney_and_urinary_tract_disorders/cancers_of_the_kidney_and_genitourinary_tract/bladder_cancer.html.

Chandrasekar, "Prostate Cancer," Merck Manual. Modified Sep. 2022; Accessed Sep. 30, 2022: http://www.merckmanuals.com/home/kidney_and_urinary_tract_disorders/cancers_of_the_kidney_and_genitourinary_tract/prostate_cancer.html?qt=prostate cancer &alt=sh.

de la Peña et al., "Expression of the matrix metalloproteases 2, 14, 24, and 25 and tissue inhibitor 3 as potential molecular markers in advanced human gastric cancer," Dis Markers. 2014;2014:285906.

Ellenrieder et al., "Role of MT-MMPs and MMP-2 in pancreatic cancer progression," Int J Cancer. Jan. 1, 2000;85(1):14-20.

Gresh, "Neuroblastoma," Merck Manual. Modified Sep. 2022; Accessed Oct. 3, 2022: https://www.merckmanuals.com/professional/pediatrics/pediatric-cancers/neuroblastoma#.

He et al., "Matrix metalloproteinase-14 is a negative prognostic marker for patients with gastric cancer," Dig Dis Sci. May 2013;58(5):1264-70.

Heinis et al., "Phage-encoded combinatorial chemical libraries based on bicyclic peptides," Nat. Chem. Biol. 2009;5(7):502-7.

Hershman, "Thyroid Cancers," Merck Manual. Revised Sep. 2020; Accessed Sep. 30, 2021: http://www.merckmanuals.com/professional/endocrine-and-metabolic-disorders/thyroid-disorders/thyroid-cancers.

Ip et al., "Atypical localization of membrane type 1-matrix metalloproteinase in the nucleus is associated with aggressive features of hepatocellular carcinoma," Mol Carcinog. Mar. 2007;46(3):225-30.

Kamat et al., "The clinical relevance of stromal matrix metalloproteinase expression in ovarian cancer," Clin Cancer Res. Mar. 15, 2006;12(6):1707-14.

Keith, "Lung Carcinoma," Merck Manual. Accessed Revised Jul. 2020; Accessed Sep. 30, 2021: http://merckmanuals.com/professional/pulmonary-disorders/tumors-of-the-lungs/lung-carcinoma.

Kerkelä et al., "Differential patterns of stromelysin-2 (MMP-10) and MT1-MMP (MMP-14) expression in epithelial skin cancers," Br J Cancer. Mar. 2, 2001;84(5):659-69.

Kikuchi et al., "Immunohistochemical detection of membrane-type-1-matrix metalloproteinase in colorectal carcinoma," Br J Cancer. Jul. 2000;83(2):215-8.

Mark, "Renal Cell Carcinoma," Merck Manual. Revised Sep. 2019; Accessed Sep. 30, 2021: http://www.merckmanuals.com/professional/genitourinary-disorders/genitourinary-cancer/renal-cell-carcinoma.

Mohammad et al., "Prognostic value of membrane type 1 and 2 matrix metalloproteinase expression and gelatinase A activity in bladder cancer," Int J Biol Markers. Apr.-Jun. 2010;25(2):69-74.

National Cancer Institute, "Understanding Cancer," Accessed Dec. 30, 2022: https://www.cancer.gov/about-cancer/understanding.

Nguyen, "Colorectal Cancer," Merck Manual. Revised Mar. 2021; Modified Sep. 2022: https://www.merckmanuals.com/home/digestive-disorders/tumors-of-the-digestive-system/colorectal-cancer#.

PCT Application PCT/GB2020/050505, filed Mar. 3, 2020.

PCT International Search Report and Written Opinion from PCT/GB2015/053247, dated Jan. 18, 2016.

PCT International Search Report and Written Opinion from PCT/GB2020/051140, dated Aug. 12, 2020.

Remacle et al., "Membrane type I-matrix metalloproteinase (MT1-MMP) is internalised by two different pathways and is recycled to the cell surface," J Cell Sci. Oct. 1, 2003;116(Pt 19):3905-16.

Remacle et al., "Novel MT1-MMP small-molecule inhibitors based on insights into hemopexin domain function in tumor growth," Cancer Res. May 1, 2012;72(9):2339-49.

Sepiashvili et al., "Potentially novel candidate biomarkers for head and neck squamous cell carcinoma identified using an integrated cell line-based discovery strategy," Mol Cell Proteomics. Nov. 2012;11(11):1404-15.

Suojanen et al., "A novel and selective membrane type-1 matrix metalloproteinase (MT1-MMP) inhibitor reduces cancer cell motility and tumor growth," Cancer Biol Ther. Dec. 2009;8(24):2362-70.

Thevenard et al., "The YSNSG cyclopeptide derived from tumstatin inhibits tumor angiogenesis by down-regulating endothelial cell migration," Int J Cancer. Mar. 1, 2010;126(5):1055-66.

Trudel et al., "Membrane-type-1 matrix metalloproteinase, matrix metalloproteinase 2, and tissue inhibitor of matrix proteinase 2 in prostate cancer: identification of patients with poor prognosis by immunohistochemistry," Hum Pathol. May 2008;39(5):731-9.

Ulasov et al., "Inhibition of MMP14 potentiates the therapeutic effect of temozolomide and radiation in gliomas," Cancer Med. Aug. 2013;2(4):457-67.

U.S. Appl. No. 16/838,367, filed Apr. 2, 2020.

U.S. Appl. No. 16/871,305, filed May 11, 2020.

Wang et al., "Co-expression of MMP-14 and MMP-19 predicts poor survival in human glioma," Clin Transl Oncol. Feb. 2013;15(2):139-45.

Zarrabi et al., "Inhibition of matrix metalloproteinase 14 (MMP-14)-mediated cancer cell migration," J Biol Chem. Sep. 23, 2011;286(38):33167-77.

Angelini et al., "Bicyclic Peptide Inhibitor Reveals Large Contact Interface with a Protease Target," ACS Chemical Biology, vol. 7, No. 5, Feb. 2012 (pp. 817-821).

No Author Listed, "Bladder Cancer", Merck Manuals, retrieved from internet <<http://www.merckmanuals.com/home/kidney_and_urinary_tract_disorders/cancers_of_the_kidney_and_genitourinary_tract/bladder_cancer.html>> Aug. 21, 2014 (12 pages).

No Author Listed, "Cholangiocarcinoma", Merck Manuals, retrieved from internet <<http://surgery.usc.edu/divisions/tumor/pancreasdiseases/web%20pages/BILIARY%20SYSTEM/cholangiocarcinoma>> Mar. 12, 2017 (2 pages).

(56) References Cited

OTHER PUBLICATIONS

No Author Listed, "Colorectal Cancer", Merck Manuals, retrieved from internet <<http://www.merckmanuals.com/home/digestive_disorders/tumors_of_the_digestive_system/colorectal_cancer.htm>> Aug. 21, 2014 (1 page).

No Author Listed, "Lung Carcinoma", Merck Manuals, retrieved from internet <<http://merckmanuals.com/professional/pulmonary-disorders/tumors-of-the-lungs/lung-carcinoma>> Mar. 12, 2017 (12 pages).

No Author Listed, "Neuroblastoma", Merck Manuals, retrieved from internet <<http://merckmanuals.com/professional/pediatrics/pediatric-cancers/neuroblastoma>> Mar. 12, 2017 (4 pages).

No Author Listed, "Prostate Cancer", Merck Manuals, retrieved from internet <<http://www.merckmanuals.com/home/kidney_and_urinary_tract_disorders/cancers_of_the_kidney_and_genitourinary_tract/prostate_cancer.html?qt=prostate cancer&alt=sh>> Aug. 21, 2014 (7 pages).

No Author Listed, "Renal Cell Carcinoma", Merck Manuals, retrieved from internet <<http://www.merckmanuals.com/professional/genitourinary-disorders/genitourinary-cance-r/renal-cell-carcinoma>> Mar. 21, 2017 (4 pages).

No Author Listed, "Thyroid Cancer", Merck Manuals, retrieved from internet <<http://www.merckmanuals.com/professional/endocrine-and-metabolic-disorders/thyroid-disorders/thyroid-cancers>> Mar. 12, 2017 (3 pages).

No Author Listed, Understanding Cancer and Related Topics, National Institute of Cancer, retrieved from internet <<http://cancer.gov/cancertopics/understandingcancer>> Aug. 21, 2014 (63 pages).

Remacle et al., "Membrane type I-matrix metalloproteinase (MT1-MMP) is internalised by two different pathways and is recycled to the cell surface," Journal of Cell Science, vol. 116, No. pt 19, Oct. 2003 (pp. 3905-3915).

Thevenard et al., "The YSNSG cyclopeptide derived from tumstatin inhibits tumor angiogenesis by down-regulating endothelial cell migration," International Journal of Cancer, vol. 126, No. 5, Mar. 2010 (pp. 1055-1066).

Adley et al., "Expression of Membrane Type 1 Matrix Metalloproteinase (MMP-14) in Epithelial Ovarian Cancer: High Level Expression in Clear Cell Carcinoma," Gynecol Oncol., 2009, vol. 112(2), pp. 319-324.

Augoff et al., "Upregulated Expression and Activation of Membrane-Associated Proteases in Esophageal Squamous Cell Carcinoma," Oncology Reports, 2014, vol. 31, pp. 2820-2826.

Barbolina et al., "Microenvironmental Regulation of Membrane Type 1 Matrix Metalloproteinase Activity in Ovarian Carcinoma Cells via Collagen-Induced EGR1 Expression," The Journal of Biological Chemistry, 2007, vol. 282(7), pp. 4924-4931.

De La Pena et al., "Expression of the Matrix Metalloproteases 2, 14, 24 and 25 and Tissue Inhibitor 3 as Potential Molecular Markers in Advanced Human Gastric Cancer," Disease Markers, 2014, pp. 1-9.

Ellenrieder et al., "Role of MT-MMPs and MMP-2 in Pancreatic Cancer Progression," Int. J. Cancer, 2000, vol. 85, pp. 14-20.

He et al., "Matrix Metalloproteinase-14 is a Negative Prognostic Marker for Patients with Gastric Cancer," Dig Dis Sci, 2013, vol. 58, pp. 1264-1270.

Ip and Fan, "Atypical Localization of Membrane Type 1-Matrix Metalloproteinase in the Nucleus is Associated With Aggressive Features of Hepatocellular Carcinoma," Molecular Carcinogenesis, 2007, vol. 46, pp. 225-230.

Kamat et al., "The Clinical Relevance of Stromal Matrix Metalloproteinase Expression in Ovarian Cancer," Clin Cancer Res, 2006, vol. 12(6), pp. 1707-1714.

Kerkela et al., "Differential Patterns of Stromelysin-2 (MMP-10) and MT1-MMP (MMP-14) Expression in Epithelial Skin Cancers," British Journal of Cancer, 2001, vol. 84(5, pp. 659-669.

Kikuchi et al., "Immunohistochemical Detection of Membrane-Type-1-Matrix Metalloproteinase in Colorectal Carcinoma," British Journal of Cancer, 2000, vol. 83(2), pp. 215-218.

Mohammad et al., "Prognostic Value of Membrane Type 1 and 2 Matrix Metalloproteinase Expression and Gelatinase A Activity in Bladder Cancer," Int. J. Biol. Markers, 2010, vol. 25(2), pp. 69-74.

Sepiashvili et al., "Potentially Novel Candidate Biomarkers for Head and Neck Squamous Cell Carcinoma Identified Using an Integrated Cell Line-based Discovery Strategy," Molecular & Cellular Proteomics, 2012, vol. 11, pp. 1404-1415.

Ulasov et al., "Inhibition of MMP14 Potentiates the Therapeutic Effect of Temozolomide and Radiation in Gliomas," Cancer Medicine, 2013, vol. 2(4), pp. 457-467.

Wang et al., "Co-expression of MMP-14 and MMP-19 Predicts Poor Survival in Human Glioma," Clin. Transl. Oncol., 2013, vol. 15, pp. 139-145.

Anonymous, "UPI000011DEEB," retrieved from the internet: URL:https://www.uniprot.org/uniparc/UPI000011DEEB, 2014, 2 pages.

Adams et al., "Big Opportunities for Small Molecules in Immuno-oncology," Nature Reviews, 2015, 14:603-622.

Hacker et al., "Highly Constrained Bicyclic Scaffolds for the Discovery of Protease-Stable Peptides via mRNA Display", ACS Chem. Biol., 2017, 12(3):795-804.

Hirano et al., "Blockade of B7-H1 and PD-1 by monoclonal antibodies potentiates cancer therapeutic immunity," Cancer Research, 2005, 65(3):1089-1096.

Ho et al., "Expression of CD137 on Hodgkin and Reed-Sternberg cells inhibits T-cell activation by eliminating CD137 ligand expression," Cancer Res., Jan. 15, 2013, 73(2):652-661.

Lian at al, "Screening Bicyclic Peptide Libraries for Protein-Protein Interaction Inhibitors: Discovery of a Tumor Necrosis Factor-alpha Antagonist," Journal of the American Chemical Society, Aug. 14, 2013, 135(32):11990-11995.

Lowe, Derek, "Not alphafold's fault," blog—In the pipeline, 2022, 6 pages.

Lowe, Derek, "The good sides and bad sides of polar compounds," blog—In the pipeline, 2017, 15 pages.

Macheboeuf et al., "Penicillin binding proteins: key players in bacterial cell cycle and drug resistance processes", FEMS Microbiol Rev., 2006, 30(5):673-691.

Micoine et al., "A general strategy for ligation of organic and biological molecules to dawson and keggin polyoxotungstates", Org Chem. Lett., 2007, 9(20):3981-3984.

Nishiwada et al., "Nectin-4 expression contributes to tumor proliferation, angiogenesis and patient prognosis in human pancreatic cancer," Journal of Experimental & Clinical Cancer Research, Biomed Central Ltd., 2015, 34(1):30, 9 pages.

Palma et al., " CD137 and CD137 ligand constitutively coexpressed on human T and B leukemia cells signal proliferation and survival," Int J Cancer., Jan. 20, 2004, 108(3):390-398.

Rajendran et al., "CD137 signaling in Hodgkin and Reed-Sternberg cell lines induces IL-13 secretion, immune deviation and enhanced growth," Oncoimmunology, 2016, 5(6):e1160188, 7 pages.

Solomons, "Organic Chemistry", 4th ed, 1988, p. 902 (3 pages).

Thornber, "Isosterism and molecular modification in drug design", Chem. Soc. Rev, 1979, 8(4):563-580.

Yampolsky et al., "The exchangeability of amino acids in proteins", Genetics, 2005, 170(4):1459-1472.

Adams, "Molecular control of arterial-venous blood vessel identity," J Anat. Jan. 2003;202(1):105-12.

Akanuma et al., "MicroRNA-133a regulates the mRNAs of two invadopodia-related proteins, FSCN1 and MMP14, in esophageal cancer," Br J Cancer. Jan. 7, 2014;110(1):189-98.

Annunziata et al., "Phase 1, open-label study of MEDI-547 in patients with relapsed or refractory solid tumors," Invest New Drugs. Feb. 2013;31(1):77-84.

Anonymous, "Constrained Peptides Unconstrained Thinking Forward-Looking Statements," URL:https://investors.bicycletherapeutics.com/static-files/1e4832c5-1181-4fcc-acd9-c1dbb1c8b594, Aug. 1, 2019.

Askoxylakis et al., "A new peptide ligand for targeting human carbonic anhydrase IX, identified through the phage display technology," PLoS One. Dec. 31, 2010;5(12):e15962.

Ausiello et al., "Functional topography of discrete domains of human CD38," Tissue Antigens. Dec. 2000;56(6):539-47.

(56) References Cited

OTHER PUBLICATIONS

Baek et al. "Effects of Histidine and Sucrose on the Biophysical Properties of a Monoclonal Antibody," Pharm Res (2017) 34; 629-639.
Banerji et al., "Preliminary pharmacokinetic assessment of BT1718: A phase I/IIa trial of BT1718 (a first in class Bicycle Toxin Conjugate) in patients with advanced solid tumours," Nov. 13, 2018;abstract 178.
Barbas et al., "Semisynthetic combinatorial antibody libraries: a chemical solution to the diversity problem," Proceedings of the National Academy of Sciences of the United States of America, vol. 89, No. 10, May 1992 (pp. 4457-4461).
Bardia et al., "Efficacy and Safety of Anti-Trop-2 Antibody Drug Conjugate Sacituzumab Govitecan (IMMU-132) in Heavily Pretreated Patients With Metastatic Triple-Negative Breast Cancer," J Clin Oncol. Jul. 1, 2017;35(19):2141-2148.
Bech et al., "Chemical Strategies for Half-Life Extension of Biopharmaceuticals: Lipidation and Its Alternatives," ACS Medicinal Chemistry Letters, vol. 9, No. 7, Jun. 2018 (pp. 577-580).
Bennett et al., "Abstract 4481: BT5528, an EphA2-targeting Bicycle Toxin Conjugate (BTC): Profound efficacy without bleeding and coagulation abnormalities in animal models," Cancer Res. 2019; 79 (13 suppl); 4481.
Bennett et al., "Abstract 5854: BT5528, a Bicycle Toxin Conjugate targeting EphA2 has potent anti-tumor activity without bleeding or coagulation abnormalities in preclinical models." Cancer Res. 2018;78(13 suppl):5854.
Bennett et al., "Abstract 5855: Bicycle Drug Conjugates Targeting EphA2 for the Treatment of Solid Tumors: Discovery and Selection of BT5528," Cancer Res. 2018; 78 (13 suppl); 5855.
Bennett et al., "MMAE Delivery Using the Bicycle Toxin Conjugate BT5528," Mol Cancer Ther. Jul. 2020; 19(7):1385-1394.
Bennett et al., "The Mechanism of Action of BT1718, a Novel Small-Molecule Drug Conjugate for the Treatment of Solid Tumors Expressing MT1-MMP," AACR-NCI-EOrTC International Conference: Molecular Targets and Cancer Therapeutics 2018;26-30.
Bennett, "BT1718, a Bicycle Drug Conjugate (BTC): Profound Efficacy Without Bleeding and Coagulation Abnormalities in Animal Models," AACR Annual Meeting 2019. 4481.
Berenson, "Multiple Myeloma," Merck Manual. Revised Oct. 2021; Accessed Oct. 4, 2022: https://www.merckmanuals.com/home/blood-disorders/plasma-cell-disorders/multiple-myeloma?query=multiple%20myeloma.
Berge et al., "Pharmaceutical salts," J Pharm Sci. 1977;66(1):1-19.
Bicycle Therapeutics, "Bicycle Therapeutics and Cancer Research UK Announce Inititation of First Clinical Study of a Bicyclic Peptide (Bicycle®)," Press Release. Feb. 13, 2018: https://investors.bicycletherapeutics.com/node/6651/pdf.
Bicycle Therapeutics, "Bicycle Therapeutics to Present New BT1718 Data in the "New Drugs on the Horizon" Session at the 2018 American Association for Cancer Research Meeting," Press Release. Apr. 3, 2018.
Bicycle Therapeutics, "Bicycle Therapeutics to Present on BT5528, a Bicycle Toxin Conjugate Targeting EphA2 for the Treatment of Solid Tumours, at World ADC 2019," Business Wire Release. Mar. 5, 2019.
BicycleTx Limited, "Study BT5528-100 in Patients With Advanced Solid Tumors Associated With EphA2 Expression," ClinicalTrials.gov Identifier NCT04180371. First Posted Nov. 27, 2019; Accessed Dec. 30, 2022: https://clinicaltrials.gov/ct2/show/NCT04180371.
Binda et al., "The EphA2 receptor drives self-renewal and tumorigenicity in stem-like tumor-propagating cells from human glioblastomas," Cancer Cell. Dec. 11, 2012; 22(6); 765-80.
Biron et al., "Improving oral bioavailability of peptides by multiple N-methylation: somatostatin analogues," Angew. Chem. Int. Ed., vol. 47, No. 14, Mar. 2008 (pp. 2595-2599).
Bogaerts et al., "Individual patient data analysis to assess modifications to the RECIST criteria," Eur J Cancer. Jan. 2009;45(2):248-60.
Booth et al., "Crowd control in the crypt," Nat Med. Dec. 2002;8(12):1360-1.
Borghaei et al., "Nivolumab versus Docetaxel in Advanced Nonsquamous Non-Small-Cell Lung Cancer," N Engl J Med. Oct. 22, 2015;373(17):1627-39.
Borrelli et al., "Cell Penetrating Peptides as Molecular Carriers for Anti-Cancer Agents," Molecules, vol. 23, No. 2, Feb. 2018 (28 pages).
Bouchard et al., "Antibody-drug conjugates—a new wave of cancer drugs," Bioorg Med Chem Lett. Dec. 1, 2014;24(23):5357-63.
Brahmer et al., "Nivolumab versus Docetaxel in Advanced Squamous-Cell Non-Small-Cell Lung Cancer," N Engl J Med. Jul. 9, 2015;373(2):123-35.
Brannan et al., "EphA2 in the early pathogenesis and progression of non-small cell lung cancer," Cancer Prev Res (Phila). Dec. 2009;2(12):1039-49.
Brantley-Sieders et al., "Eph receptor tyrosine kinases in tumor and tumor microenvironment," Curr Pharm Des. 2004; 10(27); 3431-42.
Brantley-Sieders et al., "Eph/ephrin profiling in human breast cancer reveals significant associations between expression level and clinical outcome," PLoS One. 2011; 6(9): e24426.
Brantley-Sieders et al., "Impaired tumor microenvironment in EphA2-deficient mice inhibits tumor angiogenesis and metastatic progression," FASEB J. Nov. 2005; 19(13):1884-6.
Bristol-Myers Squibb, "An Investigational Immuno-therapy Study to Investigate the Safety and Effectiveness of Nivolumab, and Nivolumab Combination Therapy in Virus-associated Tumors (CheckMate358)," ClinicalTrials.gov Identifier NCT02488759. First Posted Jul. 2, 2015; Accessed Feb. 23, 2018: https://clinicaltrials.gov/ct2/show/study/NCT02488759.
Cabanillas et al., "Phase I study of maytansine using a 3-day schedule," Cancer Treat Rep. Mar. 1978;62(3):425-8.
Cancer Research UK, "Soft tissue sarcomas," Accessed Sep. 30, 2022: http://about-cancer.cancerresearchuk.org/about-cancer/soft-tissue-sarcoma.
Cancer Research UK, "Triple Negative Breast Cancer," Accessed Sep. 30, 2022: https://www.cancerresearchuk.org/about-cancer/breast-cancer/stages-types-grades/types/triple-negative-breast-cancer#.
Cancer Research UK, "Types of lung cancer," Accessed Sep. 30, 2022: https://www.cancerresearchuk.org/about-cancer/lung-cancer/stages-types-grades/types#.
Cancer Research UK, "Your mouth and cancer drugs," Accessed Sep. 30, 2022: https://www.cancerresearchuk.org/about-cancer/cancer-in-general/treatment/cancer-drugs/side-effects/your-mouth.
Center for Pancreatic and Biliary Diseases, "Bile Duct Cancer," University of Southern California, Department of Surgery. Retreived from https://web.archive.org/web/20171207023733/http://www.surgery.usc.edu:80/divisions/tumor/PancreasDiseases/web%20pages/BILIARY%20SYSTEM/cholangiocarcinoma.html.
Centers for Disease Control and Prevention, "What Can I Do to Reduce My Risk of Ovarian Cancer?" Division of Cancer Prevention and Control. Aug. 3, 2022.
Chabner et al., "Initial clinical trials of maytansine, an antitumor plant alkaloid," Cancer Treat Rep. Mar. 1978;62(3):429-33.
Chahinian et al., "Phase I study of weekly maytansine given by iv bolus or 24-hour infusion," Cancer Treat Rep. Nov.-Dec. 1979;63(11-12):1953-60.
Chan and Nie, "Quantum dot bioconjugates for ultrasensitive nonisotopic detection," Science. Sep. 25, 1998; 281 (5385): 2016-8.
Chang et al., "Five different anti-prostate-specific membrane antigen (PSMA) antibodies confirm PSMA expression in tumor-associated neovasculature," Cancer Res. Jul. 1, 1999; 59(13):3192-8.
Chang et al., "Subtiligase: a tool for semisynthesis of proteins," Proc Natl Acad Sci U S A. Dec. 20, 1994;91(26):12544-8.
Chen and Harrison, "Cell-penetrating peptides in drug development: enabling intracellular targets," Biochem Soc Trans. Aug. 2007;35(Pt 4):821-5.
Chen et al., "Peptide ligands stabilized by small molecules," Angew Chem Int Ed Engl. Feb. 3, 2014;53(6):1602-6.
Chen et al., "Structurally diverse cyclisation linkers impose different backbone conformations in bicyclic peptides," Chembiochem. May 7, 2012; 13(7): 1032-8.

(56) References Cited

OTHER PUBLICATIONS

Chen, "The Bicycle Platform: an Efficient Technology to Generate High Affinity, High Selectivity Molecules (Bicycles) With Unique Drug Like Properties That Are Amenable to Conjugation," URL:https://www.bicycletherapeutics.com/wp-content/uploads/16_PEGS-Bicycle_-30-04-2017-poster.pdf, Apr. 26, 2017.
Cheng et al., "Blockade of EphA receptor tyrosine kinase activation inhibits vascular endothelial cell growth factor-induced angiogenesis," Mol Cancer Res. Nov. 2002; 1(1): 2-11.
Cherney et al., "Macrocyclic amino carboxylates as selective MMP-8 inhibitors," J Med Chem. May 21, 1998;41(11):1749-51.
Chiche et al., "Hypoxia-inducible carbonic anhydrase IX and XII promote tumor cell growth by counteracting acidosis through the regulation of the intracellular pH," Cancer Res. Jan. 1, 2009;69(1):358-68.
Chung et al., "Bicycle synthesis through peptide macrocyclization using aziridine aldehydes followed by late stage disulfide bond installation," Med. Chem. Commun., 2013. 4:1124-1128.
Committee for Medicinal Products for Human Use (CHMP), "Assessment Report: Kadcyla; International non-proprietary name: Trastuzumab emtansine; Procedure No. EMEA/H/C/002389/0000," European Medicines Agency. Sep. 19, 2013;EMA/749228/2013.
Cook et al., "Pharmacokinetic (PK) Assessment of BT1718: A Phase 1/2a Study of BT1718, a First in Class Bicycle Toxin Conjugate (BTC), in Patients (PTS) with Advanced Solid Tumours," Annals of Oncology 2019; vol. 30.
Cortes et al., "Phase II study of the halichondrin B analog eribulin mesylate in patients with locally advanced or metastatic breast cancer previously treated with an anthracycline, a taxane, and capecitabine," J Clin Oncol. Sep. 1, 2010;28(25):3922-8.
Davies and Riechmann, "Antibody VH Domains as Small Recognition Units," Nature Biotechnology, vol. 13, No. 5, May 1995 (pp. 475-479).
Dagher et al., "c-Kit and CD38 are expressed by long-term reconstituting hematopoietic cells present in the murine yolk sac," Biol Blood Marrow Transplant. 1998;4(2):69-74.
Dawson et al., "Synthesis of proteins by native chemical ligation," Science. Nov. 4, 1994;266(5186):776-9.
De Kruif et al., "Selection and Application of Human Single Chain Fv Antibody Fragments from a Semi-synthetic Phage Antibody Display Library with Designed CDR3 Regions," Journal of Molecular Biology, vol. 248, No. 1, Apr. 1995 (pp. 97-105).
Deaglio et al., "CD38 is a signaling molecule in B-cell chronic lymphocytic leukemia cells," Blood. Sep. 15, 2003;102(6):2146-55.
Deonarain et al., "Small-Format Drug Conjugates: A Viable Alternative to ADCs for Solid Tumours?" Antibodies (Basel). 2018;7(2):16.
Derossi et al., "The third helix of the Antennapedia homeodomain translocates through biological membranes," J Biol Chem. Apr. 8, 1994;269(14):10444-50.
Deyle et al., "Phage Selection of Cyclic Peptides for Application in Research and Drug Development." Acc Chem Res. 2017;50(8):1866-1874.
Di, "Strategic approaches to optimizing peptide ADME properties," AAPS J. Jan. 2015;17(1):134-43.
Diamantis and Banerji, "Antibody-drug conjugates—an emerging class of cancer treatment," Br J Cancer. Feb. 16, 2016;114(4):362-7.
Diaz-Perlas et al., "Branched BBB-shuttle peptides: chemoselective modification of proteins to enhance blood-brain barrier transport," Chemical Science, vol. 9, No. 44, Sep. 2018 (pp. 8409-8415).
Driggers et al., "The exploration of macrocycles for drug discovery—an underexploited structural class," Nat Rev Drug Discov. Jul. 2008;7(7):608-24.
Dubois et al., "New ways to image and target tumour hypoxia and its molecular responses," Radiother Oncol. Sep. 2015;116(3):352-7.
Dunne et al., "EphA2 Expression Is a Key Driver of Migration and Invasion and a Poor Prognostic Marker in Colorectal Cancer," Clin Cancer Res. Jan. 1, 2016;22(1):230-242.
Duong and Rodan, "The role of integrins in osteoclast function," J Bone Miner Metab. 1999;17(1):1-6.
Eagan et al., "Early clinical study of an intermittent schedule for maytansine (NSC-153858): brief communication," J Natl Cancer Inst. Jan. 1978;60(1):93-6.
Eder et al., "A phage display derived stabilised bicyclic peptide targeting MMP-14 shows high imaging contrast in small animal PET imaging," Eur J Nucl Med Mol Imaging. Oct. 2015;42(suppl 1):S140-S141.
Eisenhauer et al., "New response evaluation criteria in solid tumours: revised RECIST guideline (version 1.1)," Eur J Cancer. Jan. 2009;45(2):228-47.
Elson-Schwab et al., "Guanidinylated neomycin delivers large, bioactive cargo into cells through a heparan sulfate-dependent pathway," J Biol Chem. May 4, 2007;282(18):13585-91.
EP Office Action issued for EP Application EP 18739911.8, dated Jan. 25, 2023.
Fehrenbacher et al., "Atezolizumab versus docetaxel for patients with previously treated non-small-cell lung cancer (POPLAR): a multicentre, open-label, phase 2 randomised controlled trial," Lancet. Apr. 30, 2016;387(10030):1837-46.
Fiacco and Roberts, "N-Methyl Scanning Mutagenesis Generates Protease-Resistant G Protein Ligands with Improved Affinity and Selectivity," ChemBioChem, vol. 9, No. 14, Sep. 2008 (pp. 2200-2203).
Figure 3.8 of "Immunobiology: The Immune System in Health and Disease," Garland Science, 2001.
Francis et al., "Bone and Soft Tissue Sarcomas: UK Incidence and Survival: 1996-2010," National Cancer Intelligence Network. Nov. 2013;v2.0.
Fumet et al. "Phase Ib/II trail evaluating the safety, tolerability and immunological activity of durvalumab (MEDI4736) (anti-PD-L1) plus tremelimumab (anti-CTLA-4) combined with FOLFOX in patients with metastatic colorectal cancer" ESMO 2018;3(4):1-9.
Funaro et al., "Human CD38 is associated to distinct molecules which mediate transmembrane signaling in different lineages," Eur J Immunol. Oct. 1993;23(10):2407-11.
Funaro et al., "Involvement of the multilineage CD38 molecule in a unique pathway of cell activation and proliferation," J Immunol. Oct. 15, 1990;145(8):2390-6.
Galsky et al., "Phase I trial of the prostate-specific membrane antigen-directed immunoconjugate MLN2704 in patients with progressive metastatic castration-resistant prostate cancer," J Clin Oncol. May 1, 2008;26(13):2147-54.
Gandhi et al., "MP69-11 Carbonic Anhydrase IX Assay: A Paradigm Shift in Diagnosis of Malignant Cystic Renal Lesions, " J Urol. May 18, 2015;193(4S):e870-e871.
Gelb et al., "Abstract A047: MT1-MMP Immunohistochemistry (IHC) analysis of tumor microarrays (TMAs) using a novel scoring system guides patient selection for BT1718 expansion cohorts," Mol Cancer Ther. 2019;18(12 suppl):A047.
Gen path diagnostics (https://genpathdiagnostics.com/patients/oncology/solid-tumors/accessed06/30/23).
Gentilucci et al., "Chemical modifications designed to improve peptide stability: incorporation of non-natural amino acids, pseudopeptide bonds, and cyclization." Curr Pharm Des. 2010;16(28):3185-203.
Gokel et al., "Crown Ethers: Sensors for Ions and Molecular Scaffolds for Materials and Biological Models," Chem. Rev., vol. 104, 2004 (pp. 2723-2750).
Gradishar et al., "Significantly longer progression-free survival with nab-paclitaxel compared with docetaxel as first-line therapy for metastatic breast cancer," J Clin Oncol. Aug. 1, 2009;27(22):3611-9.
Griffiths et al., "Isolation of high affinity human antibodies directly from large synthetic repertoires," EMBO Journal, vol. 13, No. 14, Jul. 1994 (pp. 3245-3260).
Grisold et al., "Peripheral neuropathies from chemotherapeutics and targeted agents: diagnosis, treatment, and prevention," Neuro Oncol. Sep. 2012;14 Suppl 4(Suppl 4):iv45-54.
Gu et al., "The influence of the penetrating peptide iRGD on the effect of paclitaxel-loaded MT1-AF7p-conjugated nanoparticles on glioma cells," Biomaterials. Jul. 2013;34(21):5138-48.

(56) References Cited

OTHER PUBLICATIONS

Guo et al., "Prognostic significance of combinations of RNA-dependent protein kinase and EphA2 biomarkers for NSCLC," J Thorac Oncol. Mar. 2013;8(3):301-8.
Gupta et al., "Intracellular delivery of large molecules and small particles by cell-penetrating proteins and peptides," Adv Drug Deliv Rev. Feb. 28, 2005;57(4):637-51.
Hanna et al., "Randomized phase III trial of pemetrexed versus docetaxel in patients with non-small-cell lung cancer previously treated with chemotherapy," J Clin Oncol. May 1, 2004;22(9):1589-97.
Harrison et al., "Abstract 5144: BT1718, a novel bicyclic peptide-maytansinoid conjugate targeting MT1-MMP for the treatment of solid tumors: Design of bicyclic peptide and linker selection," Cancer Res. 2017;77(13 suppl):5144.
Helft et al., "A phase I study of cantuzumab mertansine administered as a single intravenous infusion once weekly in patients with advanced solid tumors," Clin Cancer Res. Jul. 1, 2004;10(13):4363-8.
Herbst et al., "Pembrolizumab versus docetaxel for previously treated, PD-L1-positive, advanced non-small-cell lung cancer (KEYNOTE-010): a randomised controlled trial," Lancet. Apr. 9, 2016;387(10027):1540-1550.
Hess et al., "Molecular regulation of tumor cell vasculogenic mimicry by tyrosine phosphorylation: role of epithelial cell kinase (Eck/EphA2)," Cancer Res. Apr. 15, 2001;61(8):3250-5.
Hess et al., "Backbone Cyclic Peptidomimetic Melanocortin-4 Receptor Agonist as a Novel Orally Administrated Drug Lead for Treating Obesity," Journal of Medicinal Chemistry, vol. 51, No. 4, Jan. 2008 (pp. 1026-1034).
Hoogenboom and Winter, "By-passing immunisation. Human antibodies from synthetic repertoires of germline VH gene segments rearranged in vitro," Journal of Molecular Biology, vol. 227, No. 2, Sep. 1992 (pp. 381-388).
Hoshino et al., "Mapping of the catalytic and epitopic sites of human CD38/NAD+ glycohydrolase to a functional domain in the carboxyl terminus," J Immunol. Jan. 15, 1997;158(2):741-7.
Hu-Lieskovan et al. "New combination strategies using PD-1/L1 checkpoint inhibitors as a backbone," Cancer J. 2017; 23(1):10-22.
Hurov et al., "BT7480, a novel fully synthetic tumor-targeted immune cell agonist (TICA™) induces tumor localized CD137 agonism." https://www.bicycletherapeutics/com/wp-content/uploads/2020- 06-16-BT7480-AaCR-2020poster-P5552_Final_CD137-in-title-002.pdf 2020.
Ide and Ichikawa, "A novel method for artificial lipid-bilayer formation," Biosensors and Bioelectronics, vol. 21, No. 4, Jan. 2005 (pp. 672-677).
International Search Report and Written Opinion issued by the European Patent Office as International Searching Authority for International Application No. PCT/EP2017/083953 mailed May 9, 2018 (9 pages).
International Search Report and Written Opinion issued by the European Patent Office as International Searching Authority for International Application No. PCT/EP2018/060498, mailed Jul. 5, 2018 (13 pages).
Jackson and Stover, "Using the Lessons Learned From the Clinic to Improve the Preclinical Development of Antibody Drug Conjugates," Pharm Res. Nov. 2015;32(11):3458-69.
Jackson et al., "A human antibody-drug conjugate targeting EphA2 inhibits tumor growth in vivo," Cancer Res. Nov. 15, 2008;68(22):9367-74.
Jespers et al., "Selection of optical biosensors from chemisynthetic antibody libraries," Protein Engineering Design and Selection, vol. 17, No. 10, Oct. 2004 (pp. 709-713).
Jin et al., "(alpha)V(beta)3 Integrin-Targeted Radionuclide Therapy with 64Cu-cyclam-RAFT-c(-RGDfK-)4," Mol Cancer Ther. Sep. 2016;15(9):2076-85.
Jones et al., "Randomized phase III study of docetaxel compared with paclitaxel in metastatic breast cancer," J Clin Oncol. Aug. 20, 2005;23(24):5542-51.
Jones et al., "Targeting membrane proteins for antibody discovery using phage display," Scientific Reports, vol. 6, No. 1, May 2016 (pp. 1-11).
Kanazawa et al., "Non-obese-diabetic mice: immune mechanisms of pancreatic β-cell destruction," Diabetologia, vol. 27, Jul. 1984 (pp. 113-115).
Kang et al., "A randomized, open-label, multicenter, adaptive phase 2/3 study of trastuzumab emtansine (T-DM1) versus a taxane (TAX) in patients (pts) with previously treated HER2-positive locally advanced or metastatic gastric/gastroesophageal junction adenocarcinoma (LA/MGC/GEJC)," J Clin Oncol. Feb. 1, 2016;34(4 suppl).
Kellog et al., "Disulfide-linked antibody-maytansinoid conjugates: optimization of in vivo activity by varying the steric hindrance at carbon atoms adjacent to the disulfide linkage," Bioconjug Chem. Apr. 20, 2011;22(4):717-27.
Kemp and McNamara, "Conformationally restricted cyclic nonapeptides derived from L-cysteine and LL-3-amino-2-piperidone-6-carboxylic acid (LL-Acp), a potent .beta.- turn-inducing dipeptide analog," J Org Chem. 1985;50(26):5834-8.
Kessenbrock et al., "Matrix metalloproteinases: regulators of the tumor microenvironment," Cell. Apr. 2, 2010;141(1):52-67.
Khan et al., "Engineering Lipid Bilayer Membranes for Protein Studies," International Journal of Molecular Sciences, vol. 14, No. 11, Nov. 2013 (pp. 21561-21597).
Kinch et al., "Predictive value of the EphA2 receptor tyrosine kinase in lung cancer recurrence and survival," Clin Cancer Res. Feb. 2003;9(2):613-8.
Kitanaka et al., "CD38 ligation in human B cell progenitors triggers tyrosine phosphorylation of CD19 and association of CD19 with lyn and phosphatidylinositol 3-kinase," J Immunol. Jul. 1, 1997;159(1):184-92.
Kitanaka et al., "CD38-mediated signaling events in murine pro-B cells expressing human CD38 with or without its cytoplasmic domain," J Immunol. Feb. 15, 1999;162(4):1952-8.
Knight and Adams, "Three genes for lupus nephritis in NZB x NZW mice," Journal of Experimental Medicine, vol. 147, No. 6, Jun. 1978 (pp. 1653-1660).
Konopleva et al., "Ligation of cell surface CD38 protein with agonistic monoclonal antibody induces a cell growth signal in myeloid leukemia cells," J Immunol. Nov. 1, 1998;161(9):4702-8.
Kreidieh et al., "Overview, prevention and management of chemotherapy extravasation," World J Clin Oncol. Feb. 10, 2016;7(1):87-97.
Krop et al., "Trastuzumab emtansine versus treatment of physician's choice for pretreated HER2-positive advanced breast cancer (TH3RESA): a randomised, open-label, phase 3 trial," Lancet Oncol. Jun. 2014;15(7):689-99.
Kumagai et al., "Ligation of CD38 suppresses human B lymphopoiesis," J Exp Med. Mar. 1, 1995;181(3):1101-10.
Landolt et al., "Clear Cell Renal Cell Carcinoma is linked to Epithelial-to-Mesenchymal Transition and to Fibrosis," Physiol Rep. Jun. 2017;5(11):e13305.
Lani et al., "Identification of high affinity, highly selective bicyclic peptides (Bicycles®) to transmembrane proteins using phage display screening on whole cells," Abstract, PEGS Summit, Boston, Massachusetts, May 2017 (1 page).
Laudanski et al., "Increased serum level of membrane type 1-matrix metalloproteinase (MT1-MMP/MMP-14) in patients with breast cancer," Folia Histochem Cytobiol. Jan. 1, 2010;48(1):101-3.
Lea and Simeonov, "Fluorescence polarization assays in small molecule screening," Expert Opinion in Drug Discovery, vol. 6, No. 1, Jan. 2011 (pp. 17-32).
Lee and Aarhus, "ADP-ribosyl cyclase: an enzyme that cyclizes NAD+ into a calcium-mobilizing metabolite," Cell Regul. Mar. 1991;2(3):203-9.
Lee et al., "ADP-ribosyl cyclase and CD38. Multi-functional enzymes in Ca+2 signaling," Adv Exp Med Biol. 1997;419:411-9.
Lee et al., "Structural determination of a cyclic metabolite of NAD+ with intracellular Ca2+-mobilizing activity," J Biol Chem. Jan. 25, 1989;264(3):1608-15.

(56) References Cited

OTHER PUBLICATIONS

Leighton, "Pharmacology Review: Kadcyla (ado-trastuzumab emtansine)," Center for Drug Evaluation and Research Application No. 125427Orig1s000. Feb. 1, 2013.
Li et al., "Fluorescent mu selective opioid ligands from a mixture based cyclic peptide library," ACS Comb Sci. 2012;14(12):673-9.
Li et al., "The overexpression membrane type 1 matrix metalloproteinase is associated with the progression and prognosis in breast cancer," Am J Transl Res. Jan. 15, 2015;7(1):120-7.
Li et al., "Up-regulation of EphA2 and down-regulation of EphrinA1 are associated with the aggressive phenotype and poor prognosis of malignant glioma," Tumour Biol. Oct. 2010;31(5):477-88.
Lin et al., "EphA2 overexpression is associated with angiogenesis in ovarian cancer," Cancer. Jan. 15, 2007;109(2):332-40.
Linch et al., "OX40 Agonists and Combination Immunotherapy: Putting the Pedal to the Metal," Frontiers in Oncology, vol. 5, No. 34, Feb. 16, 2015, pp. 1-14.
Linde et al., "Structure-Activity Relationship and Metabolic Stability Studies of Backbone Cyclization and N-Methylation of Melanocortin Peptides," Biopolymers, vol. 90, No. 5, No Month Listed 2008 (pp. 671-682).
Lindstrom et al., "Myasthenia gravis," Advances in Immunology, vol. 42, Dec. 1988 (pp. 233-284).
Loktev et al., "Multicyclic Peptides as Scaffolds for the Development of Tumor Targeting Agents," Current Medicinal Chemistry, 2017, vol. 24, pp. 2141-2155.
Lovering et al., "Escape from flatland: increasing saturation as an approach to improving clinical success," J Med Chem. Nov. 12, 2009;52(21):6752-6.
Lund et al., "CD38 signaling in B lymphocytes is controlled by its ectodomain but occurs independently of enzymatically generated ADP-ribose or cyclic ADP-ribose," J Immunol. Mar. 1, 1999;162(5):2693-702.
M.D. Anderson Cancer Center, "Nivolumab and HPV-16 Vaccination in Patients With HPV-16 Positive Incurable Solid Tumors," ClinicalTrials.gov Identifier NCT02426892. First Posted Apr. 27, 2015; Accessed Feb. 23, 2018: https://clinicaltrials.gov/ct2/show/study/NCT02426892.
Mallone et al., "Signaling through CD38 induces NK cell activation," Int Immunol. Apr. 1, 2001;13(4):397-409.
Mark H. Bilsky; "Gliomas"; Merck Manual (https://merckmanuals.com/professional/neurologic-disorders/intracranial-and-spinal-tumors/gilomas); May 2023.
Marks et al., "By-passing immunization. Human antibodies from V-gene libraries displayed on phage," Journal of Molecular Biology, vol. 222, No. 3, Dec. 1991 (pp. 581-597).
Maron and Cohen, "H-2K mutation controls immune response phenotype of autoimmune thyroiditis. Critical expression of mutant gene product in both thymus and thyroid glands," Journal of Experimental Medicine, vol. 152, No. 4, Oct. 1980 (pp. 1115-1120).
Marme, "VEGFs, angiopoietins, Ephrins and their receptors: putative targets for tumor therapy?" Ann Hematol. 2002;81 Suppl 2:S66.
McFarlin et al., "Experimental Allergic Encephalomyelitis in the Rat: Response to Encephalitogenic Proteins and Peptides," Science, vol. 179, No. 4072, Feb. 1973 (pp. 478-480).
Merck Manual (https://www.merckanuals.com/home/blood-disorders/plasma-cell-disorders/multiple-myeloma?query=pancreaticultiple%20myeloma accessed Apr. 9, 2021).
Merritt et al., "Analysis of EphA2 expression and mutant p53 in ovarian carcinoma," Cancer Biol Ther. Oct. 2006;5(10):1357-60.
Milowsky et al., "Phase 1/2 multiple ascending dose trial of the prostate-specific membrane antigen-targeted antibody drug conjugate MLN2704 in metastatic castration-resistant prostate cancer," Urol Oncol. Dec. 2016;34(12):530.e15-530.e21.
Mitra et al., "Structure-Activity Relationship Analysis of Peptides Targeting the EphA2 Receptor," Biochemistry. 2010;49(31):6687-95.
Moraes et al., "Immune checkpoint inhibitors (anti PD-1 or anti PD-L1) versus chemotherapy for second- or third-line treatment of metastatic non-small cell lung cancer," Cochrane Database Syst Rev. 2017; 2017(4):CD012644.
Morra et al., "CD38 is functionally dependent on the TCR/CD3 complex in human T cells," FASEB J. May 1998; 12(7):581-92.
Morrison, "Chemical Strategies for Bicyclic Peptide Formation," Univ. of Leeds, Sep. 2015, pp. 1-60.
Mudali et al., "Patterns of EphA2 protein expression in primary and metastatic pancreatic carcinoma and correlation with genetic status," Clin Exp Metastasis. 2006;23(7-8):357-65.
Mudd et al., "Identification and Optimization of EphA2-Selective Bicycles for the Delivery of Cytotoxic Payloads," J Med Chem. 2020;63(8):4107-16.
Mugera and Ward, "Acute toxicity of maytansine in F344 rats," Cancer Treat Rep. Oct. 1977;61(7):1333-8.
Mullis and Faloona, "Specific synthesis of DNA in vitro via a polymerase-catalyzed chain reaction," Methods in Enzymology, vol. 155, Jan. 1987 (pp. 335-350).
Mulder et al., "Scaffold Optimization in Discontinuous Epitope Containing Protein Mimics of gp120 Using Smart Libraries," Org. Biomol. Chem. 2013, vol. 11, pp. 2676-2684.
Nakamoto and Bergemann, "Diverse roles for the Eph family of receptor tyrosine kinases in carcinogenesis," Microsc Res Tech. Oct. 1, 2002;59(1):58-67.
Nakamura et al., "EPHA2/EFNA1 expression in human gastric cancer," Cancer Sci. Jan. 2005;96(1):42-7.
Nakamura et al., "Involvement of alpha(v)beta3 integrins in osteoclast function," J Bone Miner Metab. 2007;25(6):337-44.
Nan et al., "Dual function glutamate-related ligands: discovery of a novel, potent inhibitor of glutamate carboxypeptidase II possessing mGluR3 agonist activity," J Med Chem. Mar. 9, 2000;43(5):772-4.
National Cancer Institute, "What is Cancer?" Updated Oct. 11, 2021: https://www.cancer.gov/about-cancer/understanding/what-is-cancer.
Neri and Supuran, "Interfering with pH regulation in tumours as a therapeutic strategy," Nat Rev Drug Discov. Sep. 16, 2011;10(10):767-77.
Nestor, "The medicinal chemistry of peptides," Curr Med Chem. 2009; 16(33):4399-418.
Nguyen, "Pancreatic Cancer," Merck Manual. Revised Mar. 2021; Accessed Oct. 4, 2022: https://www.merckmanuals.com/home/digestive-disorders/tumors-of-the-digestive-system/pancreatic-cancer?query=pancreatic%20cancer.
Nissim et al., "Antibody fragments from a 'single pot' phage display library as immunochemical reagents," EMBO Journal, vol. 13, No. 3, Feb. 1994 (pp. 692-698).
NIH National Human Genome Research Institute, "Animal Model," Genome.gov. Jan. 4, 2022.
Oehlke et al., "Cellular uptake of an alpha-helical amphipathic model peptide with the potential to deliver polar compounds into the cell interior non-endocytically," Biochim Biophys Acta. Nov. 11, 1998;1414(1-2):127-39.
Okazaki et al., "A rheostat for immune responses: the unique properties of PD-1 and their advantages for clinical application," Nat Immunol. Dec. 2013;14(12):1212-8.
Okuyama et al., "Small-molecule mimics of an alpha-helix for efficient transport of proteins into cells," Nat Methods. Feb. 2007;4(2):153-9.
Oliver et al., "Mouse CD38 is down-regulated on germinal center B cells and mature plasma cells," J Immunol. Feb. 1, 1997;158(3):1108-15.
Pahwa et al., "Monitoring and Inhibiting MT1-MMP during Cancer Initiation and Progression," Cancers (Basel). Feb. 17, 2014;6(1):416-35.
Partida-Sánchez et al., "Cyclic ADP-ribose production by CD38 regulates intracellular calcium release, extracellular calcium influx and chemotaxis in neutrophils and is required for bacterial clearance in vivo," Nat Med. Nov. 2001;7(11):1209-16.
Pavlidou et al., "Nanodiscs Allow Phage Display Selection for Ligands to Non-Linear Epitopes on Membrane Proteins," PLoS One, vol. 8, No. 9, Sep. 2013 (8 pages).

(56) References Cited

OTHER PUBLICATIONS

PCT International Preliminary Report on Patentability for PCT/GB2020/052619, dated Apr. 19, 2022.
PCT International Search Report and Written Opinion for PCT Application No. PCTGB2020/051144, mailed by the ISA/EP on Aug. 18, 2020, 16 Pages.
PCT International Search Report and Written Opinion for PCT/GB2020/051140, Aug. 20, 2020.
PCT International Search Report and Written Opinion for PCT/GB2020/052619, dated Apr. 22, 2021.
PCT International Search Report and Written Opinion from PCT/EP2017/083954, dated Apr. 18, 2018.
PCT International Search Report and Written Opinion from PCT/EP2019/065993, dated Sep. 13, 2019.
PCT International Search Report and Written Opinion from PCT/GB2017/051250, dated Jul. 28, 2017.
PCT International Search Report and Written Opinion from PCT/GB2017/053560, dated Jan. 29, 2018.
PCT International Search Report and Written Opinion from PCT/GB2018/050017, dated Mar. 12, 2018.
PCT International Search Report and Written Opinion from PCT/GB2018/051118, dated Jun. 4, 2018.
PCT International Search Report and Written Opinion from PCT/GB2018/051779, dated Aug. 23, 2018.
PCT International Search Report and Written Opinion from PCT/GB2018/053676, dated Mar. 7, 2019.
PCT International Search Report and Written Opinion from PCT/GB2018/053678, dated Mar. 11, 2019.
PCT International Search Report and Written Opinion from PCT/GB2019/053080, dated Jan. 30, 2020.
PCT International Search Report and Written Opinion from PCT/GB2019/053537, dated Mar. 2, 2020.
PCT International Search Report and Written Opinion from PCT/GB2019/053539, dated Mar. 2, 2020.
PCT International Search Report and Written Opinion from PCT/GB2019/053540, dated Mar. 2, 2020.
PCT International Search Report and Written Opinion from PCT/GB2020/050505, dated Apr. 21, 2020.
PCT International Search Report and Written Opinion from PCT/GB2020/050874 dated Jun. 17, 2020.
PCT International Search Report and Written Opinion from PCT/GB2020/051827, dated Oct. 23, 2020.
PCT International Search Report and Written Opinion from PCT/GB2020/051829, dated Oct. 21, 2020.
PCT International Search Report and Written Opinion from PCT/GB2021/051451, dated Sep. 22, 2021.
PCT International Search Report and Written Opinion from PCT/GB2021/052001 dated Nov. 12, 2021.
PCT International Search Report from PCT/GB2019/053020, dated Apr. 6, 2020.
Peng et al., "Combined features based on MT1-MMP expression, CD11b + immunocytes density and LNR predict clinical outcomes of gastric cancer," J Transl Med. Jun. 2013;11(1):153.
Pickens et al., "Practical Considerations, Challenges and Limitations of Bioconjugation via Azide-Alkyne Cycloaddition," Bioconjugate Chem., 2018, vol. 29, pp. 686-701.
Pietraszek et al., "Lumican: a new inhibitor of matrix metalloproteinase-14 activity," FEBS Lett. Nov. 28, 2014;588(23):4319-24.
Pivot et al., "Pooled analyses of eribulin in metastatic breast cancer patients with at least one prior chemotherapy," Ann Oncol. Aug. 2016;27(8):1525-31.
Polakis, "Antibody Drug Conjugates for Cancer Therapy," Pharmacol Rev. Jan. 2016;68(1):3-19.
Poliakov et al., "Diverse roles of eph receptors and ephrins in the regulation of cell migration and tissue assembly," Dev Cell. Oct. 2004;7(4):465-80.
Poon et al., "Preclinical safety profile of trastuzumab emtansine (T-DM1): mechanism of action of its cytotoxic component retained with improved tolerability," Toxicol Appl Pharmacol. Dec. 1, 2013;273(2):298-313.
Poreba, "Protease-activated prodrugs: strategies, challenges, and future directions," Febs J. 2020;287(10):1936-1969.
Purdie and Benoiton, "Piperazinedione formation from esters of dipeptides containing glycine, alanine, and sarcosine: the kinetics in aqueous solution," J Chem Soc Perkin 2. 1973;14:1845-52.
Qi et al., "Serial determination of glomerular filtration rate in conscious mice using FITC-inulin clearance," Am J Physiol Renal Physiol. Mar. 2004;286(3):F590-6.
Ramirez et al., "Defining causative factors contributing in the activation of hedgehog signaling in diffuse large B-cell lymphoma," Leuk Res. Oct. 2012;36(10):1267-73.
Randall et al., "Expression of murine CD38 defines a population of long-term reconstituting hematopoietic stem cells," Blood. May 15, 1996;87(10):4057-67.
Reagan-Shaw et al., "Dose translation from animal to human studies revisited," FASEB J. Mar. 2008;22(3):659-61.
Reinertsen et al., "B-Lymphocyte Alloantigens Associated with Systemic Lupus Erythematosus," New England Journal of Medicine, vol. 299, No. 10, Sep. 1978 (pp. 515-518).
Rhodes and Pei, "Bicyclic Peptides as Next-Generation Therapeutics," Chemistry. Sep. 18, 2017;23(52):12690-12703.
Ridderstad and Tarlinton, "Kinetics of establishing the memory B cell population as revealed by CD38 expression," J Immunol. May 15, 1998;160(10):4688-95.
Rodon et al., "Cantuzumab mertansine in a three-times a week schedule: a phase I and pharmacokinetic study," Cancer Chemother Pharmacol. Oct. 2008; 62(5):911-9.
Ross and Christiano, "Nothing but skin and bone," J Clin Invest. May 2006;116(5):1140-9.
Rostovtsev et al., "A stepwise huisgen cycloaddition process: copper(I)-catalyzed regioselective "ligation" of azides and terminal alkynes," Angew Chem Int Ed Engl. Jul. 15, 2002;41(14):2596-9.
Satoh et al., "Experimental allergic encephalomyelitis mediated by murine encephalitogenic T cell lines specific for myelin proteolipid apoprotein," Journal of Immunology, vol. 138, No. 1, Jan. 1987 (pp. 179-184).
Scagliotti et al., "Phase III study comparing cisplatin plus gemcitabine with cisplatin plus pemetrexed in chemotherapy-naive patients with advanced-stage non-small-cell lung cancer," J Clin Oncol. Jul. 20, 2008;26(21):3543-51.
Schiller et al., "Comparison of four chemotherapy regimens for advanced non-small-cell lung cancer," N Engl J Med. Jan. 10, 2002;346(2):92-8.
Schreiber and Fersht, "Rapid, electrostatically assisted association of proteins," Nat Struct Biol. May 1996;3(5):427-31.
Seely and Frazier, "Regulatory Forum Opinion Piece*: Dispelling Confusing Pathology Terminology: Recognition and Interpretation of Selected Rodent Renal Tubule Lesions," Toxicol Pathol. Jun. 2015;43(4):457-63.
Shah et al., "Phase I study of IMGN901, a CD56-targeting antibody-drug conjugate, in patients with CD56-positive solid tumors," Invest New Drugs. Jun. 2016;34(3):290-9.
Shah, "Update on metastatic gastric and esophageal cancers," J Clin Oncol. Jun. 1, 2015;33(16):1760-9.
Shen et al., "Non-Clinical Disposition and Metabolism of DM1, a Component of Trastuzumab Emtansine (T-DM1), in Sprague Dawley Rats," Drug Metab Lett. 2015;9(2):119-31.
Shi et al., "One-Bead-Two-Compound Thioether Bridged Macrocyclic (gamma)-AApeptide Screening Library Against EphA2," J Med Chem. Nov. 22, 2017;60(22):9290-9298.
Sibaud et al., "Pigmentary disorders induced by anticancer agents. part I: chemotherapy," Ann Dermatol Venereol. Mar. 2013;140(3):183-96.
Smeenk et al., "Reconstructing the discontinuous and conformational (beta)1/(beta)3-loop binding site on hFSH/hCG by using highly constrained multicyclic peptides," Chembiochem. Jan. 2, 2015;16(1):91-9.
Sounni et al., "MT1-MMP expression promotes tumor growth and angiogenesis through an up-regulation of vascular endothelial growth factor expression," FASEB J. Apr. 2002;16(6):555-64.

(56) References Cited

OTHER PUBLICATIONS

Stathis et al., "A Phase I Study of IMGN529, an Antibody-Drug Conjugate (ADC) Targeting CD37, in Adult Patients with Relapsed or Refractory B-Cell Non-Hodgkin's Lymphoma (NHL)," Blood. 2014;124(21):1760.
Steck et al., "Inside-out red cell membrane vesicles: preparation and purification," Science, vol. 168, No. 3928, Apr. 1970 (pp. 255-257).
Stein et al., "Eph receptors discriminate specific ligand oligomers to determine alternative signaling complexes, attachment, and assembly responses," Genes Dev. Mar. 1, 1998;12(5):667-678.
Stevenson et al., "Preliminary studies for an immunotherapeutic approach to the treatment of human myeloma using chimeric anti-CD38 antibody," Blood. Mar. 1, 1991;77(5):1071-9.
Stuart et al., "Collagen Autoimmune Arthritis," Annual Review of Immunology, vol. 2, No Month Listed 1984 (pp. 199-218).
Sun et al., "Carbohydrate and protein immobilization onto solid surfaces by sequential Diels-Alder and azide-alkyne cycloadditions," Bioconjug Chem. Jan.-Feb. 2006;17(1):52-7.
Supuran, "Carbonic anhydrases: novel therapeutic applications for inhibitors and activators," Nat Rev Drug Discov. Feb. 2008;7(2):168-81.
Tandon et al., "Emerging strategies for EphA2 receptor targeting for cancer therapeutics." Expert Opin Ther Targets. 2011;15(1):31-51.
Tasch et al., "A unique folate hydrolase, prostate-specific membrane antigen (PSMA): a target for immunotherapy?" Crit Rev Immunol. 2001;21(1-3):249-61.
Teitelbaum, "Osteoclasts, integrins, and osteoporosis," J Bone Miner Metab. Oct. 2000;18(6):344-9.
Teitelbaum, "Osteoporosis and Integrins," J Clin Endocrinol Metab. Apr. 2005;90(4):2466-8.
Teti et al., "The role of the alphaVbeta3 integrin in the development of osteolytic bone metastases: a pharmacological target for alternative therapy?" Calcif Tissue Int. Oct. 2002;71(4):293-9.
Têtu et al., "The influence of MMP-14, TIMP-2 and MMP-2 expression on breast cancer prognosis," Breast Cancer Res. 2006;8(3):R28.
Teufel et al., "Backbone-driven collapse in unfolded protein chains," J Mol Biol. Jun. 3, 2011;409(2):250-62.
Thake et al., "Toxicity of Maytansine (NSC 153858) in Dogs and Monkeys," PB—U.S. National Technical Information Service. Feb. 1975;244628.
Timmerman et al., "Rapid and quantitative cyclization of multiple peptide loops onto synthetic scaffolds for structural mimicry of protein surfaces," Chembiochem. May 2005;6(5):821-4.
Todisco et al., "CD38 ligation inhibits normal and leukemic myelopoiesis," Blood. Jan. 15, 2000;95(2):535-42.
Tolcher et al., "Cantuzumab mertansine, a maytansinoid immunoconjugate directed to the CanAg antigen: a phase I, pharmacokinetic, and biologic correlative study," J Clin Oncol. Jan. 15, 2003;21(2):211-22.
Trouche et al., "Small multivalent architectures mimicking homotrimers of the TNF superfamily member CD40L: delineating the relationship between structure and effector function," J Am Chem Soc. Nov. 7, 2007;129(44):13480-92.
Tugyi et al., "Partial D-amino acid substitution: Improved enzymatic stability and preserved Ab recognition of a MUC2 epitope peptide," Proc Natl Acad Sci U S A. Jan. 11, 2005;102(2):413-8.
Tutt et al., "Abstract S3-01: The TNT trial: A randomized phase III trial of carboplatin (C) compared with docetaxel (D) for patients with metastatic or recurrent locally advanced triple negative or BRCA1/2 breast cancer (CRUK/07/012)," Cancer Res. 2015;75(9 suppl):S3-01.
U.S. Appl. No. 16/878,367, filed Apr. 2, 2020.
Uckun, "Regulation of human B-cell ontogeny," Blood. Nov. 15, 1990;76(10):1908-23.
Udai et al., "A Cancer research UK Phase I/IIA Trail of BT1718 (a first in class Bicycle Drug Conjugate) Given Intravenously in Patients with Advanced Solid Tumours," Journal of Clinical Oncology 2018;36(15):2610.
Upadhyaya, "Activation of CD137 Using Multivalent and Tumour Targeted Bicyclic Peptides," URL:https://www.bicycletherapeutics.com/wp-content/uploads/PU_2019-Peptide-Congress_publication.pdf, Peptide Congress, Apr. 25, 2019, 25 Pages.
U.S. Appl. No. 15/523,266, filed Apr. 28, 2017.
U.S. Appl. No. 16/472,242, filed Jun. 21, 2019.
U.S. Appl. No. 16/771,186, filed Jun. 9, 2020.
U.S. Appl. No. 17/592,966, filed Feb. 4, 2022.
U.S. Appl. No. 17/630,747, filed Jan. 27, 2022.
U.S. Appl. No. 17/779,226, filed May 24, 2022.
van Eden et al., "Cloning of the mycobacterial epitope recognized by T lymphocytes in adjuvant arthritis," Nature, vol. 331, No. 6152, Jan. 1988 (pp. 171-173).
Van Glabbeke et all., "Progression-free rate as the principal endpoint for phase II trials in soft-tissue sarcomas," Eur J Cancer. Mar. 2002;38(4):543-9.
Vandenbroucke and Libert, "Is there new hope for therapeutic matrix metalloproteinase inhibition?" Nat Rev Drug Discov. Dec. 2014;13(12):904-27.
Walker-Daniels et al., "Overexpression of the EphA2 tyrosine kinase in prostate cancer," Prostate. Dec. 1, 1999;41(4):275-80.
Wallbrecher et al., "Exploration of the design principles of a cell-penetrating bicyclic peptide scaffold," Bioconjug Chem. May 21, 2014;25(5):955-64.
Wang et al., "MMP-14 overexpression correlates with poor prognosis in non-small cell lung cancer," Tumour Biol. Oct. 2014;35(10):9815-21.
Wang et al., "Probing for integrin alpha v beta3 binding of RGD peptides using fluorescence polarization," Bioconjug Chem. May-Jun. 2005;16(3):729-34.
Wang, "An exact mathematical expression for describing competitive binding of two different ligands to a protein molecule," FEBS Lett. Feb. 27, 1995;360(2):111-4.
Wei et al., "Discovery of Peptidomimetic Antibody-Drug Conjugate Linkers with Enhanced Protease Specificity," J Med Chem. 2018;61(3):989-1000.
Wind et al., "Measuring carbonic anhydrase IX as a hypoxia biomarker: differences in concentrations in serum and plasma using a commercial enzyme-linked immunosorbent assay due to influences of metal ions," Ann Clin Biochem. Mar. 2011;48(Pt 2):112-20.
Winter et al., "Making antibodies by phage display technology," Annual Review of Immunology, vol. 12, No Month Listed 1994 (pp. 433-455).
Wu et al., "Design and Characterization of Novel EphA2 Agonists for Targeted Delivery of Chemotherapy to Cancer Cells," Chem. Biol. 2015;22(7):876-887.
Wu et al., "Structures of the CXCR4 chemokine GPCR with small-molecule and cyclic peptide antagonists," Science. Nov. 19, 2010;330(6007):1066-71.
Wykosky et al., "EphA2 as a novel molecular marker and target in glioblastoma multiforme," Mol Cancer Res. Oct. 2005;3(10):541-51.
Xiong et al., "Crystal structure of the extracellular segment of integrin alpha Vbeta3 in complex with an Arg-Gly-Asp ligand," Science. Apr. 5, 2002;296(5565):151-5.
Yang et al., "Overexpression of EphA2, MMP-9, and MVD-CD34 in hepatocellular carcinoma: Implications for tumor progression and prognosis," Hepatol Res. Dec. 2009;39(12):1169-77.
Yardley et al., "Emerge: A Randomized Phase II Study of the Antibody-Drug Conjugate Glembatumumab Vedotin in Advanced Glycoprotein NMB-Expressing Breast Cancer," J Clin Oncol. May 10, 2015;33(14):1609-19.
Yoon et al., "An efficient strategy for cell-based antibody library selection using an integrated vector system," BMC Biotechnology, vol. 12, No. 62, Sep. 2012 (10 pages).
Yoshihara et al., "Tags for labeling protein N-termini with subtiligase for proteomics," Bioorg Med Chem Lett. Nov. 15, 2008;18(22):6000-3.
Yu and Taylor, "A new strategy applied to the synthesis of an alpha-helical bicyclic peptide constrained by two overlapping i, i+7 side-chain bridges of novel design," Tetrahedron Letters. 1996;37(11):1731-1734.

(56) References Cited

OTHER PUBLICATIONS

Yuan et al., "Neuropilin-1 and the development progress of the same as a therapeutic target for malignant tumors," Tumor 2016;36:358-364.
Yuan et al., "Over-expression of EphA2 and EphrinA-1 in human gastric adenocarcinoma and its prognostic value for postoperative patients," Dig Dis Sci. Nov. 2009;54(11):2410-7.
Zelinski et al., "EphA2 overexpression causes tumorigenesis of mammary epithelial cells," Cancer Res. Mar. 1, 2001;61(5):2301-6.
Zhao et al., "Structural basis of specificity of a peptidyl urokinase inhibitor, upain-1," J Struct Biol. Oct. 2007;160(1):1-10.
Zhou et al., "Significance of semaphorin-3A and MMP-14 protein expression in non-small cell lung cancer," Oncol Lett. May 2014;7(5):1395-1400.
Zhu et al., "High-affinity peptide against MT1-MMP for in vivo tumor imaging," J Control Release. Mar. 30, 2011;150(3):248-55.
Zhuang et al., "Elevation of receptor tyrosine kinase EphA2 mediates resistance to trastuzumab therapy," Cancer Res. Jan. 1, 2010;70(1):299-308.
Zilber et al., "CD38 expressed on human monocytes: a coaccessory molecule in the superantigen-induced proliferation," Proc Natl Acad Sci U S A. Mar. 14, 2000;97(6):2840-5.
Zou et al., "PD-L1 (B7-H1) and PD-1 pathway blockage for cancer therapy: Mechanisms, response biomarkers, and combinations," Sci Transl. Med. 2016;8(328):328rv4.
Zubiaur et al., "CD38 ligation results in activation of the Raf-1/ mitogen-activated protein kinase and the CD3-zeta/zeta-associated protein-70 signaling pathways in Jurkat T lymphocytes," J Immunol. Jul. 1, 1997;159(1):193-205.
Zupo et al., "CD38 signaling by agonistic monoclonal antibody prevents apoptosis of human germinal center B cells," Eur J Immunol. May 1994;24(5):1218-22.
Adams, "Molecular control of arterial-venous blood vessel identity," Journal of Anatomy, 2003, 202(1):105-112.
Anonymous, "Bicycle Conjugates", URL:https://web.archive.org/web/20210104063050/https://www.bicycletherapeutics.com/programs , 2021, 4 pages.
Anonymous, "Bicycle Therapeutics to Present New Translational Research for BT5528 and Preclinical Data for Tumor-targeted Immune Cell Agonists at the AACR Virtual Annual Meeting II," May 15, 2020; 2 pages. URL:https://www.businesswire.com/news/home/20200515005111/en/Bicycle-Therapeutics-to-Present-New-Translational-Research-for-BT5528-and-Preelinical-Data-for-Tumor-targeted-Immune-Cell-Aaon ists-at-the-AACR-Virtual-Ann ual-Meetina-II.
Anthony et al., "Recapitulation of IVIG anti-inflammatory activity with a recombinant IgG Fc", Science Apr. 18, 2008;320(5874):373-376.
Arkadash et al., "Development of High Affinity and High Specificity Inhibitors of Matrix Metalloproteinase 14 through Computational Design and Directed Evolution" J. Biol. Chem. 2017, 292(8), 3481-3495.
Arnon et al., "The mechanisms controlling the recognition of tumor- and virus-infected cells by NKp46", Blood, Jan. 15, 2004;103(2):664-672.
Arnould et al., "Trastuzumab-based treatment of HER2-positive breast cancer: an antibody-dependent cellular cytotoxicity mechanism?", Br J Cancer, 2006, 94(2):259-267.
Banerji et al., "A Cancer research UK Phase I/IIA Trail of BT1718 (a first in class Bicycle Drug Conjugate) Given Intravenously in Patients with Advanced Solid Tumours," Journal of Clinical Oncology, Jan. 2018, 36(15):PS2610. (1 Page).
Bennett et al., "Development of BT1718, a Bicycle Drug Conjugate® (BDC) targeting MT1-MMP for treatment of solid tumours," European Journal of Cancer, Nov. 2016, 69(1):S21.
Ben-Shmuel et al., "Unleashing Natural Killer Cells in the Tumor Microenvironment—The Next Generation of Immunotherapy?", Front Immunol., 2020, 11:275.
Berkel et al. "Binding of (5 S)-penicilloic acid to penicillin binding protein 3." ACS chemical biology 8, No. 10 (2013): 2112-2116.

Bernhagen et al., "Design, synthesis and characterization of different bicyclic peptides with enhanced binding and selectiviy for various integrins", Reterived form : https://ec.europa.eu/research/participants/documents/downloadPublic?documentIds=080166e5acfd6757&appId=PPGMS, Oct. 14, 2016, XP55622035:1-6.
Beswick, Paul, "Bicycles—An entirely new class of therapeutics," accessed on https://www.bicycletherapeutics.com/wp-content/uploads/RSC-02-May-2019.pdf, 2019, 21 pages.
Biron et al., "Improving oral bioavailability of peptides by multiple N-methylation: somatostatin analoques," Angewandte Chemie International Edition, 2008, 47(14):2595-2599.
Bolland et al., "Spontaneous autoimmune disease in Fc(gamma)RIIB-deficient mice results from strain-specific epistasis", Immunity, Aug. 2000, 13(2):277-285.
Boruchov et al., "Activating and inhibitory IgG Fc receptors on human DCs mediate opposing functions", The Journal of Clinical Investigation, 2005, 115(10):2914-2923.
Brown et al., "Blockade of programmed death-1 ligands on dendritic cells enhances T cell activation and cytokine production", Journal of Immunolgy, Feb. 2003, 170(3):1257-1266.
Caratelli et al., "FCγChimeric Receptor-Engineered T Cells: Methodology, Advantages, Limitations, and Clinical Relevance", Frontiers in Immunology, Apr. 27, 2017, :8:457, 8 pages.
Challita-Eid et al., "Enfortumab Vedotin Antibody-Drug Conjugate Targeting Nectin-4 Is a Highly Potent Therapeutic Agent in Multiple Preclinical Cancer Models", Cancer Research, 2016, 76(10):3003-3013.
Chemnitz et al., "RNA fingerprints provide direct evidence for the inhibitory role of TGFβ and PD-1 on CD4+ T cells in Hodgkin lymphoma", Blood, 2007, 110(9):3226-3233.
Chen et al., "Association of FCGR3A and FCGR3B copy number variations with systemic lupus erythematosus and rheumatoid arthritis in Taiwanese patients", Arthritis & Rheumatology, 2014, 66(11):3113-3121.
Cheng et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology", J Molecular Diagnostics, 2015, 17(3):251-264.
Chinnery et al., "Viral antigen mediated NKp46 activation of NK cells results in tumor rejection via NK-DC crosstalk", Oncoimmunology, 2012, 1(6):874-883.
Christina Chun, "What are the most curable cancers?", Medical news Today(https://www.medicalnewstoday.com/articles/322700 Accessed May, 8, 2020), 2020, 8 pages.
Clarkson et al., "Treatment of refractory immune thrombocytopeniaurpura with an anti-Fc gamma-receptor antibody", The New England Journal of Medicine, 1986, 314(19):1236-1239.
Claus et al., "Tumor-targeted 4-1BB agonists for combination with T cell bispecific antibodies as off-the-shelf therapy", Sci Transl Med., Jun. 2019, 11(496):eaav5989. (12 Pages).
Clinicaltrials.gov, identifier NCT02426892, "Nivolumab and HPV-16 Vaccination in Patients with HPV-16 Positive Incurable Solid Tumors," https://clinicaltrials.gov/ct2/show/study/NCT02426892, 8 pages.
Clynes et al., "Inhibitory Fc receptors modulate in vivo cytotoxicity against tumor targets", Nature Medicine, Apr. 2000, 6(4):443-446.
Connolly et al., "Complexities of TGF-β Targeted Cancer Therapy", Int'l J. Biological Sciences, 2012, 8(7):964-978.
Costello et al., "Defective expression and function of natural killer cell-triggering receptors in patients with acute myeloid leukemia", Blood, 2002, 99(10):3661-3667.
Crameri et al., "Construction and evolution of antibody-phage libraries by DNA shuffling," Nature Medicine, Jan. 1996, 2(1):100-102.
Cui, J. Jean., "A New Challenging and Promising Era of Tyrosine Kinase Inhibitors", ACS Med Chem Lett., 2014, 5(4):272-274.
Curiel et al., "Blockade of B7-H1 improves myeloid dendritic cell-mediated antitumor immunity", In Nature medicine, 2003, 9(5):562-567.

(56) References Cited

OTHER PUBLICATIONS

Davis et al., "Natural killer cells unleashed: Checkpoint receptor blockade and BiKE/TriKE utilization in NK-mediated anti-tumor immunotherapy", Semin Immunol., 2017, 31:64-75.
Debre et al., "Infusion of Fc gamma fragments for treatment of children with acute immune thrombocytopenia purpura", Lancet, 1993, 342(8877):945-949.
Dharmadhikari, et al., "CD137 and CD137L signals are main drivers of type 1, cell-mediated immune responses." Oncoimmunology, 2016, 5(4):e1113367.
Dong, et al. "Tumor-associated B7-H1 promotes T-cell apoptosis: a potential mechanism of immune evasion", Nature Medicine, 2002, 8(8):793-800.
Dorfman et al., "Programmed death-1 (PD-1) is a marker of germinal center-associated T cells and angioimmunoblastic T-cell lymphoma." The American journal of surgical pathology, Jul. 2006, 30(7):802-810.
Dufort et al, "789: Generation of a Bicycle NK-TICA(TM), a novel NK cell engaging molecule to enhance targeted tumor cytotoxicity", Nov. 10, 2021, 9(Suppl 2):A824-A824. URL:https://jitc.bmj.com/contenl/jitc/9/Suppl_2/A824.full.pdf.
Fauriat et al., "Deficient expression of NCR in NK cells from acute myeloid leukemia: Evolution during leukemia treatment and impact of leukemia cells in NCRdull phenotype induction", Blood, 2007, 109(1):323-330.
Felices et al., "Generation of BiKEs and TriKEs to Improve NK Cell-Mediated Targeting of Tumor Cells", Methods Mol Biol., 2016, 1441:333-346.
Felices et al., "Novel CD19-targeted TriKE restores NK cell function and proliferative capacity in CLL", Blood Adv., 2019, 3(6):897-907.
Flaherty et al., "Nonclinical evaluation of GMA161—an antihuman CD16 (FcγRIII) monoclonal antibody for treatment of autoimmune disorders in CD16 transgenic mice", Toxicological Sciences, 2012, 125(1):299-309.
Forsberg, et al., "CD137 plays both pathogenic and protective roles in type 1 diabetes development in NOD mice." The Journal of Immunology, 2017, 198(10):3857-3868.
Garcia-Iglesias et al., "Low NKp30, NKp46 and NKG2D expression and reduced cytotoxic activity on NK cells in cervical cancer and precursor lesions", BMC Cancer, Jun. 16, 2009, 9:186, 8 pages.
Gauthier et al., "Multifunctional Natural Killer Cell Engagers Targeting NKp46 Trigger Protective Tumor Immunity", Cell, 2019, 177(7):1701-1713.
Gelb et al., "Abstract 391: Molecular-based enrichment strategy for Nectin-4 targeted Bicycle toxin conjugate BT8009," Cancer Res., Jul. 1, 2021, 81(13 suppl):391 (poster).
Gfeller et al., "Current tools for predicting cancer-specific T cell immunity," Oncoimmunology, 2016, 5(7):e1177691.
Gleason et al., "CD16xCD33 bispecific killer cell engager (BiKE) activates NK cells against primary MDS and MDSC CD33+ targets", Blood, 2014, 123(19):3016-3026.
Hamanishi et al. "Programmed cell death 1 ligand 1 and tumor-infiltrating CD8+ T lymphocytes are prognostic factors of human ovarian cancer", Proc. Natl. Acad. Sci. USA, 2007, 104(9):3360-3365.
Han et al., "Altered NKp30, NKp46, NKG2D, and DNAM-1 Expression on Circulating NK Cells Is Associated with Tumor Progression in Human Gastric Cancer", Journal of Immunology Research, Sep. 3, 2018, 2018:6248590, 10 pages.
Hart, et al., "De novo identification of lipid II binding lipopeptides with antibacterial activity against vancomycin-resistant bacteria." Chemical Science, 2017, 8(12):7991-7997.
Hart, et al., "Cell binding and internalization by filamentous phage displaying a cyclic Arg-Gly-Aspcontaining peptide", J. Biol. Chem., 1994, 269:12468-12474.
Hasmim et al., "Critical Role of Tumor Microenvironment in Shaping NK Cell Functions: Implication of Hypoxic Stress", Frontiers in Immunology, Sep. 23, 2015, 6:482, 9 pages.
Henriques et al., "Functional characterization of peripheral blood dendritic cells and monocytes in systemic lupus erythematosus", Rheumatology International, Apr. 2012, 32(4):863-869.
Hill et al: "Constraining Cyclic Peptides To Mimic Protein Structure Motifs", Angewandte Chemie International Edition, Nov. 24, 2014, 53(48):13020-13041.
Hinner et al., "Tumor-Localized Costimulatory T-Cell Engagement by the 4-1BB/HER2 Bispecific Antibody-Anticalin Fusion PRS-343", Clinical Cancer Research , Oct. 2019, 23(19):5878-5889.
Hsu et al., "Efficacy of plasmin-treated intravenous gamma-globulin for therapy of Kawasaki syndrome", The Pediatric Infectious Disease Journal, Jun. 1993, 12(6):509-512.
Inman et al., "PD-L1 (B7-H1) expression by urothelial carcinoma of the bladder and BCG-induced granulomata: associations with localized stage progression", Cancer, 2007, 109(8):1499-1505.
Izawa et al., "$H_2O_2$ production within tumor microenvironment inversely correlated with infiltration of CD56(dim) NK cells in gastric and esophageal cancer: possible mechanisms of NK cell dysfunction", Cancer Immunology, Immunotherapy, 2011, 60(12):1801-1810.
Johnson et al., "Melanoma-specific MHC-II expression represents a tumour-autonomous phenotype and predicts response to anti-PD-1/PD-L1 therapy", Nature Communications, Jan. 29, 2016, 7:10582(10 pages).
Johnson et al., "Relationships between drug activity in NCI preclinical in vitro and in vivo models and early clinical trials," British Journal of Cancer, 2001, 84(10):1424-1431.
Kamijo et al., "Aberrant CD137 ligand expression induced by GATA6 overexpression promotes tumor progression in cutaneous T-cell lymphoma." Blood, The Journal of the American Society of Hematology, 2018, 132(18):1922-1935.
Kang, et al., "Anti-CD137 suppresses tumor growth by blocking reverse signaling by CD137 ligand." Cancer research, 2017, 77(21):5989-6000.
Kell, Douglas B., "The Transporter-Mediated Cellular Uptake and Efflux of Pharmaceutical Drugs and Biotechnology Projects: How and Why Phospholipid Bilayer Transport is Negligible in Real Biomembranes," Molecules, 2021, 26(5629):40 pages.
Kim et al., "Synergistic signals for natural cytotoxicity are required to overcome inhibition by c-Cbl ubiquitin ligase", Immunity, Feb. 26, 2010, 32(2):175-186.
Kim, et al., "Reverse signaling through the costimulatory ligand CD137L in epithelial cells is essential for natural killer cell-mediated acute tissue inflammation." Proceedings of the National Academy of Sciences, 2012, 109(1): E13-E22.
Kleinau et al., "Induction and suppression of collagen-induced arthritis is dependent on distinct fcgamma receptors", J Exp Med., May 2000, 191(9):1611-1616.
Konishi et al., "B7-H1 Expression on Non-Small Cell Lung Cancer Cells and Its Relationship with Tumor-Infiltrating Lymphocytes and Their PD-1 Expression", Clin Cancer Res., 2004, 10(15):5094-5100.
Koo et al., "Reduction of the CD16-CD56bright NK Cell Subset Precedes NK Cell Dysfunction in Prostate Cancer", PLoS One, 2013, 8(11):e78049, 8 pages.
Krishnamoorthy et al., "Breaking the Permeability Barrier of *Escherichia coli* by Controlled Hyperporination of the Outer Membrane." Antimicrob Agents Chemother, 2016, 60(12):7372-7381.
Kylväjä, et al., "Penicillin binding protein 3 of *Staphylococcus aureus* NCTC 8325-4 binds and activates human plasminogen." BMC research notes, 2016, 9:1-10.
Lanman et al, "Analytical and Clinical Validation of a Digital Sequencing Panel for Quantitative, Highly Accurate Evaluation of Cell-Free Circulating Tumor DNA", PLoS One, 2015, 10(10):e0140712.
Lau, et al., "A penicillin-binding protein that can promote advanced-generation cephalosporin resistance and genome adaptation in the opportunistic pathogen Pseudomonas aeruginosa." International journal of antimicrobial agents, 55(3): 105896.
Levi et al., "Characterization of tumor infiltrating Natural Killer cell subset", Oncotarget, May 30, 2015, 6(15):13835-13843.
Levine et al. "Methionine residues as endogenous antioxidants in proteins", PNAS, 1996, 93(26):15036-15040.

(56) References Cited

OTHER PUBLICATIONS

Li et al., "Targeting the Fc receptor in autoimmune disease", Expert Opinion on Therapeutic Targets, 2014, 18(3):335-350.
Li, et al., "A novel strategy for in vitro selection of peptide-drug conjugates." Chemistry & biology, 2003, 10(3):233-239.
Li, et al., "Increasing the antimicrobial activity of nisin-based lantibiotics against Gram-negative pathogens." Applied and environmental microbiology, 2018, 84(12):e00052-18.
Lian et al., "Cell-Permeable Bicyclic Peptide Inhibitors against Intracellular Proteins", Journal of the American Chemical Society, Jul. 2014, 136(28):9830-9833.
Liu et al., "Abstract 3642: Tumor-antigen expression-dependent activation of the CD137 costimulatory pathway by bispecific DART proteins," American Association for Cancer Research, Jul. 2017, 77(supp 13):1-4.
Liu et al., "Plasma cells from multiple myeloma patients express B7-H1 (PD-L1) and increase expression after stimulation with IFN-{gamma} and TLR ligands via a MyD88-, TRAF6-, and MEK-dependent pathway", Blood, 2007, 110(1):296-304.
Lopus, Manu. "Antibody-DM1 conjugates as cancer therapeutics." Cancer letters, 2011, 307(2):113-118.
Lovering, "Escape from Flatland 2: complexity and promiscuity," Meducinal Chemistry Communication, Dec. 2012, 4(3):515-519.
MacFarlane 4th et al., "NK cell dysfunction in chronic lymphocytic leukemia is associated with loss of the mature cells expressing inhibitory killer cell Ig-like receptors", Oncoimmunology, May 19, 2017, 6(7):e1330235.
Mamessier et al., "Human breast tumor cells induce self-tolerance mechanisms to avoid NKG2D-mediated and DNAM-mediated NK cell recognition", Cancer Res., 2011, 71(21):6621-6632.
Manches et al., " In vitro mechanisms of action of rituximab on primary non-Hodgkin lymphomas", Blood, 2003, 101(3):949-954.
Michel, et al., "Expression of soluble CD137 correlates with activation-induced cell death of lymphocytes." Cytokine, 2000, 12(6):742-746.
Mittler, el al., "Anti-CD137 antibodies in the treatment of autoimmune disease and cancer." Immunologic research, 2004, 29:197-208.
Miyoshi and Takai, "Nectin and nectin-like molecules: biology and pathology," Am J Nephrol., 2007, 27(6):590-604.
Moore et al., "A novel bispecific antibody format enables simultaneous bivalent and monovalent co-engagement of distinct target antigens", Mabs, 2011, 3(6):546-557.
Moretta et al., "Surface NK receptors and their ligands on tumor cells", Seminars in Immunology, 2006, 18(3):151-158.
Morgan et al., "FcgammaRIIIA-158V and rheumatoid arthritis: a confirmation study", Rheumatology (Oxford), 2003, 42(4):528-533.
Muta et al., "A 13-amino-acid motif in the cytoplasmic domain of Fc gamma RIIB modulates B-cell receptor signalling", Nature, Mar. 3, 1994, 368(6466):70-73.
Nabbe et al., "Coordinate expression of activating Fc gamma receptors I and III and inhibiting Fc gamma receptor type II in the determination of joint inflammation and cartilage destruction during immune complex-mediated arthritis", Arthritis & Rheumatology, Jan. 2003, 48(1):255-265.
Nair et al., "Mimicry of Native Peptide Antigens by the Corresponding Retro-Inverso Analogs is Dependent on Their Intrinsic Structure and Interaction Propensities," The Journal of Immunology, 2003, 170(3):1362-1373.
Nakanishi et al., "Overexpression of B7-H1 (PD-L1) significantly associates with tumor grade and postoperative prognosis in human urothelial cancers" Cancer Immunology, Immunotherapy, 2007, 56:1173-1182.
Nam et. al., "The therapeutic potential of 4-1BB (CD137) in cancer", Current cancer drug targets, 2005, 5(5):357-363.
National cancer institute, "Cancer prevention overview", (https://www.cancer.gov/about-cancer/causes-prevention/patient-prevention-overview-pdq accessed May 8, 2020), 2020, 12 pages.
Nayyar et al., "Overcoming Resistance to Natural Killer Cell Based Immunotherapies for Solid Tumors", Feb. 11, 2019 ;9:51, 28 pages.
Nomi et al., "Clinical Significance and Therapeutic Potential of the Programmed Death-1 Ligand/Programmed Death-1 Pathway in Human Pancreatic Cancer", Clin Cancer Res., 2007, 13(7): 2151-2157.
Ortiz et al., "Elucidating the interplay between IgG-Fc valency and FcγR activation for the design of immune complex inhibitors", Science Translational Medicine, Nov. 2016, 8(365):365ra158.
Partida-Sanchez et al., "Regulation of dendritic cell trafficking by the ADP-ribosyl cyclase CD38: impact on the development of humoral immunity," Immunity, Mar. 2004, 20(3):279-291.
Pasero et al., "Highly effective NK cells are associated with good prognosis in patients with metastatic prostate cancer", Oncotarget 6(16), Jun. 10, 2015, 14360-14373.
Pavlova et al., "A role for PVRL4-driven cell-cell interactions in tumorigenesis," Elife., Apr. 30, 2013, 2:e00358, 24 pages.
Pearson et al., "High-Level Clonal FGFR Amplification and Response to FGFR Inhibition in a Translational Clinical Trial", Cancer Discovery, 2016, 6(8):838-851.
Phichith, et al., "Novel peptide inhibiting both TEM-1 β-lactamase and penicillin-binding proteins." The FEBS Journal, 2010, 277(23):4965-4972.
Platonova et al., "Profound coordinated alterations of intratumoral NK cell phenotype and function in lung carcinoma", Cancer Res., 2011, 71(16):5412-5422.
Pricop et al., "Differential modulation of stimulatory and inhibitory Fc gamma receptors on human monocytes by Th1 and Th2 cytokines", Journal of Immunology, 2001, 166(1):531-537.
Rataj et al., "High-affinity CD16-polymorphism and Fc-engineered antibodies enable activity of CD16-chimeric antigen receptor-modified T cells for cancer therapy", British Journal of Cancer, 2019, 120(1):79-87.
Ravetch et al., "IgG Fc receptors", Annual Review of Immunology, 2001:19:275-290.
Riddle et al., "Tumor cell surface display of immunoglobulin heavy chain Fc by gene transfer as a means to mimic antibody therapy", Human Gene Therapy, 2005, 16(7):830-844.
Robert Gale, "Cancer treatment principles", Merck Manual consumer version (https://www.merckmanuals.com/home/cancer/prevention-and-treatment-of-cancer/cancer-treatment-principles?query=Cancer%20treatment Accessed May 8, 2020), Jul. 2018, 2 pages.
Robert Gale, "Overview of Cancer therapy", Merck Manual consumer version (https://www.merckmanuals.com/professional/hematology-and-oncology/principles-of-cancer-therapy/overview-of-cancer-therapy?query=Cancer Accessed May 8, 2020), Jul. 2018, 3 pages.
Robinson et al., "Integrative Clinical Genomics of Advanced Prostate Cancer", Cell, 2015, 161(5):1215-1228.
Rocca et al., "Phenotypic and Functional Dysregulated Blood NK Cells in Colorectal Cancer Patients Can Be Activated by Cetuximab Plus IL-2 or IL-15", Frontiers in Immunology, 2016, 7:413.
Rodan, "Integrin function in osteoclasts," J Endocrinol., Sep. 1997, 154(Suppl):S47-S56.
Ross et al., "Bispecific T Cell Enager (BiTE) Antibody Constructs Can Mediate Bystander Tumor Cell Killing", PLoS ONE, Aug. 24, 2017, 12(8):1-24.
Roth et al., "Docetaxel, cisplatin, and fluorouracil; docetaxel and cisplatin; and epirubicin, cisplatin, and fluorouracil as systemic treatment for advanced gastric carcinoma: a randomized phase II trial of the Swiss Group for Clinical Cancer Research", J Clin Oncol. Aug. 1, 2007, 25(22):3217-3023.
Rothwell et al, "Utility of ctDNA to support patient selection for early phase clinical trials: the TARGET study", Nature Medicine, 2019, 25(5):738-743.
Rudgers et al., "Binding properties of a peptide derived from beta-lactamase inhibitory protein." Antimicrob Agents Chemother., 2001, 45(12):3279-3286.
Salmon et al., "Human receptors for immunoglobulin G: key elements in the pathogenesis of rheumatic disease", Arthritis & Rheumatology, 2001, 44(4):739-750.
Sausville and Burger, "Contributions of Human Tumor Xenografts to Anticancer Drug Development," Cancer Res., 2006, 66(7):3351-3354.

(56) References Cited

OTHER PUBLICATIONS

Schulke et al., "The homodimer of prostate-specific membrane antigen is a functional target for cancer therapy," Proc Natl Acad Sci U SA., Oct. 28, 2003, 100(22):12590-12595.
Seiki et al., "Membrane-type 1 matrix metalloproteinase: a key enzyme for tumor invasion." Cancer letters, 2003, 194(1):1-11.
Segal et al., "Results from an Integrated Safety Analysis of Urelumab, an Agonist Anti-CD137 Monoclonal Antibody", clinical Cancer research, 2017, 23(8):1929-1936.
Shao et al., "Copy number variation is highly correlated with differential gene expression: a pan-cancer study," BMC Medical Genetics, Nov. 9, 2019, 20(1):175.
Shao et al., "CD137 ligand, a member of the tumor necrosis factor family, regulates immune responses via reverse signal transduction." Journal of leukocyte biology, 2011, 89(1):21-29.
Sharma et al., "Plasmacytoid dendritic cells from mouse tumor-draining lymph nodes directly activate mature Tregs via indoleamine 2, 3-dioxygenase", The Journal of clinical investigation, 2007, 117(9):2570-2582.
Shaabani et al., "A patent review on PD-1/PD-L 1 antagonists: small molecules, peptides, and macrocycles (2015-2018)," Expert Opinion on Therapeutic Patents, 2018, 28(9):665-678.
Shen, et.al., "Evaluation of phage display discovered peptides as ligands for prostate-specific membrane antigen (PSMA)." PLoS One, 2013, 8(7):e68339.
Shimauchi et al., "Augmented expression of programmed death-1 in both neoplastic and non-neoplastic CD4+ T-cells in adult T-cell leukemia/lymphoma", International journal of cancer, 2007, 121(12):2585-2590.
Siddharth et al., "Nectin-4 is a breast cancer stem cell marker that induces WNT/γ-Catenin signaling via Pi3k/Akt axis," International Journal of Biochemistry and Cell Biology, 2017, 89:85-94.
Silver, "Multi-targeting by monotherapeutic antibacterials." Nat Rev Drug Discov., 2007, 6(1):41-55.
Soderstrom, et al., "CD137: A checkpoint regulator involved in atherosclerosis." Atherosclerosis, 2018, 272:66-72.
Sordo-Bahamonde et al., "Mechanisms of Resistance to NK Cell Immunotherapy", Cancers (Basel). Apr. 7, 2020, 12(4):893.
Sporn et at, "Chemoprevention of cancer." Carcinogenesis, 2000, 21(3):525-530.
Stojanovic et al., "Natural killer cells and solid tumors", Journal of Innate Immunity, 2011, 3(4):355-364.
Stringaris et al., "Leukemia-induced phenotypic and functional defects in natural killer cells predict failure to achieve remission in acute myeloid leukemia", Haematologica, May 2014, 99(5):836-847.
Strome et al., "B7-H1 blockade augments adoptive T-cell immunotherapy for squamous cell carcinoma", Cancer Res., 2003, 63(19):6501-6505.
Sun et al., "NK cell receptor imbalance and NK cell dysfunction in HBV infection and hepatocellular carcinoma", Cellular & Molecular Immunology, May 2015, 12(3):292-302.
Tarazona et al., "Current progress in NK cell biology and NK cell-based cancer immunotherapy", Cancer Immunol Immunother, 2020, 69(5):879-899.
Thompson et al., "Costimulatory B7-H1 in renal cell carcinoma patients: Indicator of tumor aggressiveness and potential therapeutic target", Proceedings of the National Academy of Sciences, 2004, 101(49):17174-17179.
Toogood, "Small Molecule Immuno-oncology Therapeutic Agents," Bioorganic & Medicinal Chemistry Letters, 2018, 28(3):319-329.
Touati et al., "Phage Selection of Bicyclic Peptide Ligands and Development of a New Peptide Cyclisation Method", These No. 5536, Oct. 2012, 117 pages.
Ün, Sanya. Charakterisierung von Peptiden für die Bindung essentieller Penicillin-bindender Proteine und die Variationen der Linkerlänge einzelkettiger TetR Varianten. Friedrich-Alexander-Universitaet Erlangen-Nuernberg (Germany), 2010. 139 pages.

Watanabe et al., "NK cell dysfunction with down-regulated CD16 and up-regulated CD56 molecules in patients with esophageal squamous cell carcinoma", Diseases of the Esophagus, 2010, 23(8):675-681.
Waterhouse et al., "Safety profile of nivolumab administered as 30-min infusion: analysis of data from CheckMate 153," Cancer Chemother Pharmacol., Apr. 2018, 81(4):679-686.
Watts, "TNF/TNFR family members in costimulation of T cell responses", Annu. Rev, Immunol., Apr. 2005, 23:23-68.
Weber, J. "Immune Checkpoint Proteins: A New Therapeutic Paradigm for Cancer—Preclinical Background: CTLA-4 and PD-1 Blockade", Seminars in Oncology, Oct. 2010, 37(5):430-439.
Wu et al., "A novel polymorphism of FcgammaRIIIa (CD16) alters receptor function and predisposes to autoimmune disease", The Journal of Clinical Investigation, 1997, 100(5):1059-1070.
Wu et al., "Natural killer cells in cancer biology and therapy", Molecular Cancer, Aug. 6, 2020, 19(1):120, 26 pages.
Wu et al., "Immunohistochemical localization of programmed death-1 ligand-1 (PD-L1) in gastric carcinoma and its clinical significance" Acta histochemica, 2006, 108(1):19-24.
Zervosen et al., "Development of New Drugs for an Old Target—The Penicillin Binding Proteins." Molecules. 2012:17 (11);12478-12505.
Zhang et al., "A new anti-HER2 antibody that enhances the antitumor efficacy of trastuzumab and pertuzumab with a distinct mechanism of action", Mol Immunol., 2020, 119:48-58.
Zhang et al., "FCGR2A and FCGR3A Polymorphisms Associated With Clinical Outcome of Epidermal Growth Factor Receptor-Expressing Metastatic Colorectal Cancer Patients Treated With Single-Agent Cetuximab", Journal of Clinical Oncology, 2007, 25(24):3712-3718.
Zugazagoitia et al., "Current Challenges in Cancer Treatment," Clinical Therapies, 2016, 38(7):1551-1566.
PCT International Preliminary Report on Patentability from PCT/GB2015/053247, dated May 2, 2017, 8 pages.
PCT International Preliminary Report on Patentability received for PCT/EP2017/083953, dated Jul. 4, 2019, 7 pages.
PCT International Preliminary Report on Patentability received for PCT/EP2017/083954, dated Jul. 4, 2019, 7 pages.
PCT International Preliminary Report on Patentability received for PCT/EP2019/066010, dated Dec. 30, 2020, 9 pages.
PCT International Preliminary Report on Patentability received for PCT/EP2019/066066, dated Dec. 30, 2020, 8 pages.
PCT International Preliminary Report on Patentability received for PCT/EP2019/066273, dated Dec. 30, 2020, 8 pages.
PCT International Preliminary Report on Patentability received for PCT/EP2021/072866, dated Mar. 2, 2023, 13 pages.
PCT International Preliminary Report on Patentability received for PCT/GB2018/050017, dated Jul. 18, 2019, 8 pages.
PCT International Preliminary Report on Patentability received for PCT/GB2018/052222, dated Feb. 13, 2020, 7 pages.
PCT International Preliminary Report on Patentability received for PCT/GB2019/050485, dated Sep. 3, 2020, 8 pages.
PCT International Preliminary Report on Patentability received for PCT/GB2019/053537, dated Jun. 24, 2021, 7 pages.
PCT International Preliminary Report on Patentability received for PCT/GB2019/053679, dated Jul. 1, 2021, 7 pages.
PCT International Preliminary Report on Patentability received for PCT/GB2019/053680, dated Jul. 1, 2021, 7 pages.
PCT International Preliminary Report on Patentability received for PCT/GB2020/050069, dated Jul. 29, 2021, 8 pages.
PCT International Preliminary Report on Patentability received for PCT/GB2020/050070, dated Jul. 29, 2021, 11 pages.
PCT International Preliminary Report on Patentability received for PCT/GB2020/050071, dated Jul. 29, 2021, 7 pages.
PCT International Preliminary Report on Patentability received for PCT/GB2020/050072, dated Jul. 29, 2021, 11 pages.
PCT International Preliminary Report on Patentability received for PCT/GB2020/050073, dated Jul. 29, 2021, 8 pages.
PCT International Preliminary Report on Patentability received for PCT/GB2020/050074, dated Jul. 29, 2021, 14 pages.
PCT International Preliminary Report on Patentability received for PCT/GB2020/052058, dated Mar. 10, 2022, 8 pages.

(56) References Cited

OTHER PUBLICATIONS

PCT International Preliminary Report on Patentability received for PCT/GB2020/052590, dated Apr. 28, 2022, 7 pages.
PCT International Preliminary Report on Patentability received for PCT/GB2021/050490, dated Sep. 9, 2022, 9 pages.
PCT International Preliminary Report on Patentability received for PCT/GB2021/050491, dated Sep. 9, 2022, 10 pages.
PCT International Preliminary Report on Patentability received for PCT/GB2022/050043, dated Jul. 20, 2023, 13 pages.
PCT International Preliminary Report on Patentability received for PCT/EP2018/060498, dated Nov. 7, 2019. 8 Pages.
PCT International Preliminary Report on Patentability received for PCT/EP2019/065993, dated Dec. 30, 2020, 7 pages.
PCT International Preliminary Report on Patentability received for PCT/GB2017/053560, dated Jun. 6, 2019, 7 pages.
PCT International Preliminary Report on Patentability received for PCT/GB2018/051779, dated Jan. 9, 2020, 6 pages.
PCT International Preliminary Report on Patentability received for PCT/GB2018/053676, dated Jul. 2, 2020, 7 pages.
PCT International Preliminary Report on Patentability received for PCT/GB2018/053678, dated Jul. 2, 2020, 9 pages.
PCT International Preliminary Report on Patentability received for PCT/GB2019/051740, dated Dec. 30, 2020, 8 pages.
PCT International Preliminary Report on Patentability received for PCT/GB2019/051741, dated Dec. 30, 2020, 7 pages.
PCT International Preliminary Report on Patentability received for PCT/GB2019/053020, dated May 6, 2021, 12 pages.
PCT International Preliminary Report on Patentability received for PCT/GB2019/053080, dated May 14, 2021, 16 pages.
PCT International Preliminary Report on Patentability received for PCT/GB2019/053536, dated Jun. 24, 2021, 07 pages.
PCT International Preliminary Report on Patentability received for PCT/GB2019/053539, dated Jun. 24, 2021, 7 pages.
PCT International Preliminary Report on Patentability received for PCT/GB2019/053540, dated Jun. 24, 2021, 8 pages.
PCT International Preliminary Report on Patentability received for PCT/GB2020/050505, dated Sep. 16, 2021, 7 pages.
PCT International Preliminary Report on Patentability received for PCT/GB2020/050874, dated Oct. 14, 2021, 11 pages.
PCT International Preliminary Report on Patentability received for PCT/GB2020/051140, dated Nov. 25, 2021, 8 pages.
PCT International Preliminary Report on Patentability received for PCT/GB2020/051144, dated Nov. 18, 2021, 9 pages.
PCT International Preliminary Report on Patentability received for PCT/GB2020/051827, dated Feb. 10, 2022, 8 pages.
PCT International Preliminary Report on Patentability received for PCT/GB2020/051829, dated Feb. 10, 2022 , 8 pages.
PCT International Preliminary Report on Patentability received for PCT/GB2020/051831, dated Feb. 10, 2022, 10 pages.
PCT International Preliminary Report on Patentability received for PCT/GB2020/051923, dated Feb. 24, 2022, 9 pages.
PCT International Preliminary Report on Patentability received for PCT/GB2020/052445, dated Apr. 14, 2022, 26 pages.
PCT International Preliminary Report on Patentability received for PCT/GB2020/053026, dated Jun. 9, 2022, 8 pages.
PCT International Preliminary Report on Patentability received for PCT/GB2021/051220, dated Dec. 1, 2022, 7 pages.
PCT International Preliminary Report on Patentability received for PCT/GB2021/051451, dated Dec. 22, 2022, 09 pages.
PCT International Preliminary Report on Patentability received for PCT/GB2021/052001, dated Feb. 16, 2023, 13 pages.
PCT International Preliminary Report on Patentability received for PCT/GB2022/050044, dated Jul. 20, 2023, 13 pages.
PCT International Preliminary Report on Patentability received for PCT/GB2022/050055, dated Jul. 20, 2023, 17 pages.
PCT International Preliminary Report on Patentability received for PCT/GB2017/051250, dated Nov. 15, 2018, 7 pages.
PCT International Preliminary Report on Patentability received for PCT/GB2018/051118, dated Nov. 7, 2019, 11 pages.
PCT International Search Report and Written Opinion received for PCT/EP2019/066010, dated Sep. 30, 2019, 12 pages.
PCT International Search Report and Written Opinion received for PCT/EP2019/066066, dated Oct. 1, 2019, 11 pages.
PCT International Search Report and Written Opinion received for PCT/EP2019/066273, dated Sep. 27, 2019, 11 pages.
PCT International Search Report and Written Opinion received for PCT/EP2021/072866, dated Dec. 21, 2021, 21 pages.
PCT International Search Report and Written Opinion received for PCT/GB2019/050485, dated Jun. 4, 2019, 12 Pages.
PCT International Search Report and Written Opinion received for PCT/GB2019/050951, dated Jul. 4, 2019, 11 pages.
PCT International Search Report and Written Opinion received for PCT/GB2019/051740, dated Aug. 29, 2019, 11 pages.
PCT International Search Report and Written Opinion received for PCT/GB2019/051741, dated Aug. 5, 2019, 10 pages.
PCT International Search Report and Written Opinion received for PCT/GB2019/053020, dated Jun. 23, 2020, 19 pages.
PCT International Search Report and Written Opinion received for PCT/GB2019/053536, dated Mar. 11, 2020, 11 pages.
PCT International Search Report and Written Opinion received for PCT/GB2019/053679, dated Mar. 11, 2020, 12 pages.
PCT International Search Report and Written Opinion received for PCT/GB2019/053680, dated Mar. 11, 2020, 11 pages.
PCT International Search Report and Written Opinion received for PCT/GB2020/050069, dated Apr. 15, 2020, 10 pages.
PCT International Search Report and Written Opinion received for PCT/GB2020/050070, dated Jun. 23, 2020, 16 pages.
PCT International Search Report and Written Opinion received for PCT/GB2020/050071, dated May 12, 2020, 10 pages.
PCT International Search Report and Written Opinion received for PCT/GB2020/050072, dated Jun. 30, 2020, 16 pages.
PCT International Search Report and Written Opinion received for PCT/GB2020/050073, dated Apr. 7, 2020, 11 pages.
PCT International Search Report and Written Opinion received for PCT/GB2020/050074, dated Jun. 23, 2020, 21 pages.
PCT International Search Report and Written Opinion received for PCT/GB2020/051831, dated Nov. 4, 2020, 13 pages.
PCT International Search Report and Written Opinion received for PCT/GB2020/051923, dated Nov. 17, 2020, 12 pages.
PCT International Search Report and Written Opinion received for PCT/GB2020/052058, dated Nov. 12, 2020, 11 pages.
PCT International Search Report and Written Opinion received for PCT/GB2020/052445, dated Mar. 4, 2021, 34 pages.
PCT International Search Report and Written Opinion received for PCT/GB2020/052590, dated Jan. 28, 2021, 9 pages.
PCT International Search Report and Written Opinion received for PCT/GB2020/053026, dated Mar. 23, 2021, 11 pages.
PCT International Search Report and Written Opinion received for PCT/GB2021/050490, dated May 19, 2021, 12 pages.
PCT International Search Report and Written Opinion received for PCT/GB2021/050491, dated May 14, 2021, 14 pages.
PCT International Search Report and Written Opinion received for PCT/GB2021/051220, dated Aug. 27, 2021, 12 pages.
PCT International Search Report and Written Opinion received for PCT/GB2022/050043, dated Nov. 17, 2022, 18 pages.
PCT International Search Report and Written Opinion received for PCT/GB2022/050044, dated Jun. 28, 2022, 19 pages.
PCT International Search Report and Written Opinion received for PCT/GB2022/050055, dated Apr. 19, 2022, 21 pages.
PCT International Search Report and Written Opinion received for PCT/GB2022/052249, dated Mar. 28, 2023, 14 pages.
PCT International Search Report and Written Opinion received for PCT/GB2022/052903, dated Mar. 13, 2023, 12 pages.
PCT International Search Report and Written Opinion received for PCT/GB2018/052222, dated Oct. 11, 2018, 9 pages.
U.S. Appl. No. 17/769,668, filed Apr. 15, 2022.
U.S. Appl. No. 18/021,748, filed Feb. 16, 2023.
U.S. Appl. No. 18/271,360, filed Jul. 7, 2023.
U.S. Appl. No. 18/271,593, filed Jul. 10, 2023.
U.S. Appl. No. 18/313,983, filed May 8, 2023.
U.S. Appl. No. 18/345,506, filed Jun. 30, 2023.

(56) References Cited

OTHER PUBLICATIONS

Anonymous, "Bicycle Therapeutics 2023 R&D Day Deck", https://investors.bicycletherapeutics.com/static-files/46599fde-67dc-40a8-9dcb-10ed8444f3le, Dec. 14, 2023, 155 pages.

Anonymous, "Bicycle Therapeutics BT8009 Regulatory Update", https://investors.bicycletherapeutics.com/static-files/265210c3-233f-4dd8-af32-d34592398d85, Sep. 11, 2023, 23 pages.

Bader et al., "Abstract 3088: Breaking from the paradigm of antibody-drug conjugates: Evaluation of clinical pharmacokinetics and safety of Bicycle Toxin Conjugates® (BTCs)", American Society of Clinical Oncology Annual Meeting, May 31-Jun. 4, 2024, 1 page.

Baldini et al., "Abstract 498: BT8009-100: A Phase I/II Study of Novel Bicyclic Peptide and MMAE Conjugate BT8009 in Patients (pts) with Advanced Malignancies Associated with Nectin-4 Expression, Including Urothelial Cancer (UC)", ASCO Genitourinary (GU) Cancers Symposium Conference, Feb. 17, 2023, 1 page.

Banerji et al., "A Cancer Research UK phase I/IIa trial of BT1718 (a first in class Bicycle Toxin Conjugate) given intravenously in patients with advanced solid tumours", ASCO, Jun. 5, 2018, 1 page.

Banerji et al., "A Cancer Research UK phase I/IIa trial of BT1718 (a first in class Bicycle Toxin Conjugate) given intravenously in patients with advanced solid tumours", NCRI, Oct. 1, 2018, 1 page.

Battula et al., "Abstract 4613: A novel fully synthetic dual targeted EphA2/CD137 Bicycle® peptide induces tumor localized CD137 agonism", American Association of Cancer Research, Jun. 22, 2020, 1 page.

Battula et al., "Abstract P794: A novel fully synthetic dual targeted EphA2/4-1BB Bicycle® peptide induces tumor localized 4-1BB agonism", SITC, Nov. 9, 2019, 1 page.

Bendell et al., "TPS3655: BT5528-100 Phase I/II Study; Safety, Pharmacokinetics & Preliminary Clinical Activity of BT5528 in Patients with Advanced Malignancies Associated with EphA2 Expression", ASCO, May 29, 2020, 1 page.

Bennett et al., "Abstract 1167/2: Development of BT1718, a novel Bicycle Drug Conjugate for the treatment of lung cancer", American Association of Cancer Research, Apr. 1, 2017, 1 page.

Bennett et al., "Abstract 164: BT5528, an EphA2-targeting Bicycle Toxin Conjugate (BTC): profound efficacy without bleeding and coagulation abnormalities in animal models", EORTC, Nov. 13, 2018, 1 page.

Bennett et al., "Abstract 5854: BT5528, a Bicycle Toxin Conjugate (BTC) targeting EphA2 has potent antitumour activity without bleeding or coagulation abnormalities in animal models", American Association of Cancer Research, Apr. 14, 2018, 1 page.

Bennett et al., "Abstract 5855: Bicycle Toxin Conjugates (BTCs) targeting EphA2 for the treatment of solid tumours: Discovery and selection of BT5528", American Association of Cancer Research, Apr. 14, 2018, 1 page.

Bennett et al., "Abstract C066: BT5528, a Bicycle Toxin Conjugate targeting EphA2: mechanism of action and clinical translation", AACR-NCI-EORTC, Oct. 29, 2019, 1 page.

Bennett, "Abstract 4481: BT5528, an EphA2-targeting Bicycle® Toxin Conjugate (BTC): Profound efficacy without bleeding and coagulation abnormalities in animal models", AACR Annual Meeting, Apr. 4, 2019, 11 pages.

Bennett, "Bicycle Conjugates to Target Solid Tumors", Next Generation Conjugates Summit, Feb. 27, 2023, 23 pages.

Bennett, "BT5528: A Bicycle Toxin Conjugate Targeting EphA2 for the Treatment of Solid Tumours", 9th Annual World ADC Conference, Mar. 6, 2019, 13 pages.

Bournakas et al., "PBP inhibitors discovered using a modified phage display platform (Bicycles)", ESCMID, Oct. 11, 2022, 1 page.

Brandish, "Bicycle Therapeutics: Precision-guided immune agonism for the treatment of cancer", Immuno UK meeting, Sep. 30, 2022, 25 pages.

Campbell et al., "Poster 1197: A multi tumor survey of Nectin-4 expression to guide BT8009 indication selection", American Association of Cancer Research, Apr. 12, 2021, 1 page.

Campbell et al., "Poster 5300: A survey of EphA2 expression by immunohistochemistry (IHC) in tumor tissue microarrays (TMAs) to support BT5528 indication selection", American Association of Cancer Research, Jun. 22, 2020, 1 page.

Carabateas et al., "Strong Analgesics, Some 1-Substituted 4-Phenyl-4-Propionoxypiperidines", Journal of Medicinal and Pharmaceutical Chemistry, Sep. 1962, 5:913-919.

CAS No. 18226-42-1, "1,3,5-Tris(bromomethyl)benzene", Chemical Book, Retrieved from: https://www.chemicalbook.com/ProductChemicalPropertiesCB0500171_EN.htm, 2023, 2 pages.

Chen et al., "Abstract A8: Novel Multimers of Bicyclic Peptides Cluster and Activate CD137 (4-1BB): A Costimulatory T -Cell Checkpoint Receptor", PEGS, Nov. 12, 2018, 1 page.

Cohen et al., "Abstract 2: Quantitation of CD137 and Nectin-4 expression across multiple tumor types to support indication selection for BT7480, a Bicycle tumor-targeted immune cell agonist™M (Bicycle TICA™)", SITC, Nov. 12, 2021, 1 page.

Cohen et al., "Abstract 5555: Development of a CD137 receptor occupancy assay to support the phase I/II study of BT7480,a Bicycle® tumor-targeted immune cell agonist (Bicycle TICA™)", American Association of Cancer Research, Apr. 8, 2022, 1 page.

Cohen et al., "Abstract A65: Development of a CD137 receptor occupancy assay to support the phase I/II study of BT7480, a Bicycle tumor-targeted immune cell agonist® (Bicycle TICA®)", AACR-BC-EORTC, Oct. 26, 2022, 1 page.

Cohen, "Translating preclinical findings into clinical biomarker assays to support the Phase I/II study of BT7480, a Bicycle tumor-targeted immune cell agonist®", World Clinical Biomarkers & CDx Summit, Sep. 28, 2022, 21 pages.

Cohen, "Turning preclinical findings into clinic-ready biomarker assays to support BT7480 development", Markets and Markets Biomarker and Companion Diagnostics Conference, Feb. 15, 2023, 21 pages.

Cook et al., "Abstract 5764: Pharmacokinetic (PK) assessment of BT1718 : A phase 1/2a study of BT1718, a first in class bicycle toxin conjugate (BTC), in patients with advanced solid tumours", EMSO, Sep. 28, 2019, 1 page.

Cooke, "Bicycles as precision guided therapeutics", UK Symposium: Advancing Drug Discovery for Oncology, Mar. 13, 2023, 15 pages.

Drumm et al., "Genetic Variation and Clinical Heterogeneity in Cystic Fibrosis", Annu. Rev. Pathol. Mech. Dis., 2012, 7:267-282.

Dufort et al., "Abstract 1340: Modulation of the natural killer cell immune response to tumor with a synthetic tumor-immune cell agonist, NK-TICA®", American Association for Cancer Research Annual Meeting, Apr. 8, 2024, 1 page.

Dufort et al., "Abstract 15699: Generation of a Bicycle NK-TICA™, a novel NK cell engaging molecule designed to induce targeted tumor cytotoxicity", SITC, Nov. 12, 2022, 1 page.

Dufort et al., Abstract 1806: Modulation of the natural killer (NK) cell immune response to tumor with novel synthetic tumor-immune cell agonist, NK-TICA™, American Association for Cancer Research Annual Meeting, Apr. 17, 2023, 1 page.

Dufort et al., "Abstract 4233: Generation of a Bicycle NK-TICA™, a novel NK cell engaging molecule designed to induce targeted tumor cytotoxicity", American Association for Cancer Research, Apr. 8, 2022, 1 page.

Dufort, "Bicycles: Bispecific, Precision-guided NK Cell Activators for the Treatment of Solid Tumors", Innate Killer Summit, Mar. 29, 2023, 23 pages.

Eder et al., "Bicyclic Peptides as a New Modality for Imaging and Targeting of Proteins Overexpressed by Tumors", Cancer Res., Feb. 15, 2019, 79(4):841-852.

Evans et al., "Abstract CT253: Phase 1/2 study of the safety, pharmacokinetics, and preliminary clinical activity of BT7480 in patients with Nectin-4 associated advanced malignancies", American Association for Cancer Research Annual Meeting, Apr. 18, 2023, 1 page.

Frigerio, "Expanding the Potential of ADCs: Bicyclic Peptide (Bicycle®) Toxin Conjugates May Offer Advancements Over Traditional ADCs", World ADC, Mar. 20, 2023, 28 pages.

Frigerio, "Targeting Tumors with Bicycle Conjugates", PEGS Boston, May 17, 2023, 31 pages.

(56) References Cited

OTHER PUBLICATIONS

Gelb et al., "Abstract A047: MT1-MMP Immunohistochemistry (IHC) analysis of tumor microarrays (TMAs) using a novel scoring system guides patient selection for BT1718 expansion cohorts", AACR-NCI-EORTC, Oct. 27, 2019, 1 page.
GenBank Accession No. CZR33441.1, "uncharacterized protein FPRO_01747 [Fusariurn proliferatum ET1]", National Center for Biotechnology Information, Retrieved from: https://www.ncbi.nlm.nih.gov/protein/1111492376, Dec. 6, 2016, 1 page.
Harrison et al., "Abstract 5144: BT1718, a novel bicyclic peptide-maytansinoid conjugate targeting MT1-MMP for the treatment of solid tumours: Design of bicyclic peptide and linker selection", AACR Annual meeting, Apr. 1, 2017, 1 page.
Harrison et al., "Discovery and development of BT1718, a novel bicyclic peptidemaytansinoid conjugate targeting MT1-MMP for the treatment of solid tumours: In vitro and in vivo activities", PEGS, Apr. 30, 2017, 1 page.
Hu et al., "Lessons Learned from Molecular Scaffold Analysis", Journal of Chemical Information and Modeling, 2011, 51(8):1742-1753.
Hurov et al., "Abstract 1340: BT7455, a fully synthetic Bicycle tumor-targeted immune cell agonist®, leads to potent EphA2-dependent CD137 agonism and robust anti-tumor efficacy", SITC, Nov. 10, 2022, 1 page.
Hurov et al., "Abstract 3257: Activation of 4-1BB using multivalent and tumour targeted bicyclic peptides", American Association of Cancer Research, Apr. 2, 2019, 1 page.
Hurov et al., "Abstract 3257: Activation of CD137 using multivalent and tumor targeted Bicycle peptides", Cancer Res, Jul. 1, 2019, 79(13_Supplement):3257, 3 pages.
Hurov et al., "Abstract 700: EphA2/CD137 Bicycle® tumor-targeted immune cell agonists (TICAs™) induce tumor regressions, immunogenic memory, and reprogramming of the tumor immune microenvironment", SITC, Nov. 9, 2020, 1 page.
Hurov et al., "Abstract P398: Activation of the T cell costimulatory protein CD137 using multivalent bicyclic peptides", SITC, Nov. 6, 2018, 1 page.
Hurov et al., "Abstract P782: A novel fully synthetic dual targeted Nectin-4/4-1BB Bicycle® peptide induces tumor localized 4-1BB agonism", SITC, Nov. 9, 2019, 1 page.
Hurov et al., "BT7480, a novel fully synthetic Bicycle tumor-targeted immune cell agonist™ (Bicycle TICA™) induces tumor localized CD137 agonism", Journal for Immuno Therapy of Cancer, 2021, 9(11):e002883, pp. 1-13.
Hurov et al., "Poster 1728: Nectin-4-dependent immune cell stimulation and anti-tumor efficacy by BT7480, a Nectin-4/CD137 Bicycle® tumor-targeted immune cell agonist (TICA™)", American Association of Cancer Research, Apr. 12, 2021, 1 page.
Hurov, "BT7480, a novel and fully synthetic Bicycle tumor-targeted immune cell agonist®", Festival of Biologics, Nov. 4, 2022, 23 pages.
Kanakia et al., "Development of CD137 (4-1BB) receptor occupancy assay using fluorescently labeled Bicycles®", AACR Tumor Immunology & Immunotherapy, Oct. 19, 2020, 1 page.
Keen, "A novel fully synthetic dual targeted Nectin-4/4-1BB Bicycle® peptide induces tumor localized 4-1BB agonism", SITC, Nov. 6-10, 2019, 19 pages.
Keen, "BT5528, an EphA2-targeting Bicycle® Toxin Conjugate", World ADC congress, Oct. 11, 2019, 24 pages.
Keen, "BT7480, a novel Nectin-4 dependent agonist of the immune cell costimulatory receptor CD137", AACR Annual Meeting, Apr. 10-15 and May 17-21, 2021, 23 pages.
Kristensson et al., "Novel Bicyclic Peptide Multimers Activate T Cell Costimulatory Protein CD137", Elrig Drug Discovery, Oct. 9, 2018, 1 page.
Kristensson et al., "Novel Bicyclic Peptide Multimers Activate T Cell Costimulatory Protein CD137", Promega Biologics, Jul. 18, 2018, 1 page.
Kumara et al., "Fusarium proliferatum, an endophytic fungus from *Dysoxylum binectariferum* Hook.f, produces rohitukine, a chromane alkaloid possessing anti-cancer activity", Antonie van Leeuwenhoek, 2012, 101(2):323-329.
Lahdenranta et al., "Abstract 1356: Transcriptional profiling of Bicycle® tumor-targeted CD137 agonist-treated mouse tumors revealed an early and rapid activation of myeloid cells followed by infiltration of cytotoxic T cells into the tumor", SITC, Nov. 10, 2022, 1 page.
Lahdenranta et al., "Abstract 5301: Tumor-targeted activation of CD137 using Bicycle® molecules: New insights into mechanism of action and discovery of BT7455, a clinical candidate for the treatment of EphA2-expressing cancers", American Association for Cancer Research Annual Meeting, Apr. 9, 2024, 1 page.
Lahdenranta et al., "Abstract A067: BT7480, a synthetic Bicycle tumor-targeted immune cell agonist® (Bicycle TICA®), induces reprogramming of the tumor immune microenvironment through tumor localized CD137 agonism", CICON, Sep. 29, 2022, 1 page.
Lahdenranta et al., "Poster 1319: Rapid accumulation of cytotoxic payload in tumor tissue drives BT5528 activity in tumor models", American Association of Cancer Research, Apr. 12, 2021, 1 page.
Lahdenranta et al., "Poster 1724: Microinjection of Nectin-4/CD137 tumor-targeted immune cell agonist (TICA™) activates the local tumor microenvironment", American Association of Cancer Research, Apr. 12, 2021, 1 page.
Lahdenranta et al., "Poster 706: BT7480, a fully synthetic tumor-targeted immune cell agonist (TICA™) induces tumor localized CD137 agonism and modulation of tumor immune microenvironment", SITC, Nov. 9, 2020, 1 page.
Loriot et al., "Abstract TPS4619: A phase 2/3 study of Bicycle® Toxin Conjugate zelenectide pevedotin (BT8009) targeting Nectin-4 in patients with locally advanced or metastatic urothelial cancer (1a/mUC) (Duravelo-2)", American Society of Clinical Oncology Annual Meeting, May 31-Jun. 4, 2024, 1 page.
Ludbrook, "Bicycle Toxin Conjugates to Target Solid Tumors", 3rd ADC Target Selection Summit, Dec. 6, 2023, 20 pages.
Luus et al., "Abstract 1832: EphA2-dependent CD137 agonism and anti-tumor efficacy by BT7455, a Bicycle tumor-targeted immune cell agonist®", American Association for Cancer Research Annual Meeting, Apr. 17, 2023, 1 page.
McDonnell, "Bicycles for precision guided delivery", Boulder Peptide Symposium, Nov. 9, 2022, 29 pages.
McKean et al., "A Combined Phase I/II Study of BT8009 a Novel Bicycle® Toxin Conjugate with MMAE in Patients with Advanced Malignancies with Nectin-4", ASCO, Jun. 4, 2021, 1 page.
McKean et al., "BT8009-100 Phase I/II Study of Novel Bicyclic Peptide and MMAE Conjugate BT8009 in Patients with Advanced Malignancies Associated with Nectin-4 Expression", American Association for Cancer Research, Apr. 8-13, 2022, 17 pages.
McKean et al., "BT8009-100 Phase I/II Study of the Safety, Pharmacokinetics, & Preliminary Clinical Activity of BT8009 in Patients with Nectin-4 Expressing Advanced Malignancies", ESMO, Sep. 17, 2020, 1 page.
McKean, "A first in class phase I/II study of the novel bicyclic peptide and MMAE conjugate, BT5528, in patients with advanced malignancies associated with EphA2 expression", AACR-NCI-EORTC, Oct. 7-10, 2021, 19 pages.
Mistry et al., "Abstract 15523: Establishing the preclinical/translational PK/PD relationship for BT7480, a Nectin4/CD137 Bicycle tumor-targeted immune cell agonist™ (Bicycle TICA™)", SITC, Nov. 12, 2021, 1 page.
Mistry et al., "Synthesis of Bicycle® Peptides using Gold-mediated Cysteine Arylation", European Peptide Synthesis Conference, Mar. 7, 2023, 1 page.
Mudd et al., "Bicyclic Peptides for Positron Emission Tomography (PET) Imaging of MT1-MMP Expressing tumours", PEGS, Apr. 30, 2017, 1 page.
Mudd et al., "Discovery of BT8009: A Nectin-4 Targeting Bicycle Toxin Conjugate for the Treatment of Cancer", Journal of Medicinal Chemistry, 2022, 65(21): 14261-14970.
Mudd et al., "Gold-Mediated Multiple Cysteine Arylation for the Construction of Highly Constrained Bicycle Peptides", Bioconjugate Chemistry, 2022, 33(8):1441-1445.

(56) References Cited

OTHER PUBLICATIONS

Mudd et al., "Potent anti-tumor activity of a Lead-212 labelled MT1-MMP targeting Bicycle Radionuclide Conjugate™", TIDES USA—Oligonucleotide, May 8, 2023, 1 page.
Newman et al., "Anti-Infectives Drug Discovery at Bicycle Therapeutics", ESCMID, Oct. 11, 2022, 1 page.
Newman, "Characterisation of novel, noncovalent cyclic peptide (Bicycles®) inhibitors of PBP3s from important Gram-negative pathogens", ESCMID, Oct. 11, 2022, 18 pages.
Ngo et al., "Abstract 333: Activity of the erythropoietin-producing hepatocellular A2 receptor (EphA2) targeting Bicycle® Toxin Conjugate (Btctm) BCY6033 in EGFR inhibitor resistant non-small cell lung cancer (NSCLC) patient derived xenografts", American Association for Cancer Research, Apr. 8, 2022, 1 page.
Papadopoulos et al., "Abstract TPS2689: A Combined Phase I/II Study of a Novel Bicycle Tumor-targeted Immune Cell Agonist® BT7480 in Patients with Nectin-4 Associated Advanced Malignancies", ASCO, Jun. 6, 2022, 1 page.
Park et al., "Abstract 3756: Small Synthetic, Multivalent Bicyclic Peptides That Activate T Cell Costimulatory Protein CD137", American Association of Cancer Research, Apr. 14, 2018, 1 page.
Park et al., "Abstract 3756: Small Synthetic, Multivalent Bicyclic Peptides That Activate T Cell Costimulatory Protein CD137", ELRIG Drug Discovery, Oct. 9, 2018, 1 page.
Repash et al., "BT7480, a novel fully synthetic tumor-targeted immune cell agonist (TICA™) induces tumor localized CD137 agonism", AACR Tumor Immunology & Immunotherapy, Oct. 19, 2020, 10 pages.
Rezvaya et al., "Abstract 1207: NKp46 engaging Bicycle NK-TICA® drives tumor targeted cytotoxicity", SITC, Nov. 10, 2022, 1 page.
Rietschoten et al., "Abstract 268: Small Synthetic, Multivalent Bicyclic Peptides That Activate T Cell Costimulatory Protein CD137", 35th European Peptide Symposium, Aug. 1, 2018, 1 page.
Rigby et al., "Abstract 4479: BT8009: A bicyclic peptide toxin conjugate targeting Nectin-4 (PVRL4) displays efficacy in preclinical tumor models", Cancer Res, 2019, 79(13_Supplement):4479, 3 pages.
Rigby et al., "Abstract C061: BT8009, a Bicycle® Toxin Conjugate targeting Nectin-4, shows target selectivity, and efficacy in preclinical large and small tumor models", AACR-NCI-EORTC, Oct. 29, 2019, 1 page.
Rigby et al., "BT8009; A Nectin-4 Targeting Bicycle® Toxin Conjugate for Treatment of Solid Tumors", Molecular Cancer Therapeutics, 2022, 21(12):1-27.
Rigby, "Abstract 4479: BT8009: A bicyclic peptide toxin conjugate targeting Nectin-4 (PVRL4) displays efficacy in preclinical tumour models", AACR Annual Meeting, Apr. 2, 2019, 10 pages.
Santos et al., "Abstract 35472: Characterization of Nectin-4 protein expression in non-small cell lung cancer patients", AACR-BC-EORTC, Oct. 13, 2023, 1 page.
Shah et al., "Abstract A28: Establishment of an ex vivo tissue culture platform as a preclinical model to assess the mechanism of action of Bicycle® tumor-targeted immune cell agonists in NSCLC", AACR-BC-EORTC, Oct. 26, 2022, 1 page.
Singh et al., "Protein Engineering Approaches in the Post-Genomic Era", Current Protein and Peptide Science, 2017, 18(4):1-11.
Skynner et al., "BT1718, a novel Bicycle Drug Conjugate® shows potent anti-tumor activity in diverse cell-derived and patient-derived tumor xenograft models", PEGS, Apr. 30, 2017, 1 page.
Stanczuk et al., "Abstract 1388: Utility of humanized animal models for in vivo evaluation of NK-TICA®, novel Bicycle® tumor-targeted immune cell agonist® (Bicycle TICA®) designed to engage NK cells", SITC, Nov. 10, 2022, 1 page.
Stanczuk et al., "Abstract 1826: Development of in vivo models for evaluation of NK-TICA™, novel Bicycle® tumortargeted immune cell agonist® designed to engage NK cells", American Association for Cancer Research Annual Meeting, Apr. 17, 2023, 1 page.
Su, "Key DMPK Attributes of BT7480, a Bicycle Tumor-targeted Immune Cell Agonist™ Targeting Nectin-4 and Agonizing CD137", NEDMDG symposium, May 31, 2023, 20 pages.
Teufel et al., "Abstract 4920: Bicyclic Peptides for Positron Emission Tomography (PET) Imaging of MT1-MMP Expressing Tumors", American Association of Cancer Research, Apr. 1, 2017, 1 page.
Tiberghien, "Highlighting the Potential of Bicycle Conjugates to Target Solid Tumours", World ADC, Mar. 20, 2023, 24 pages.
Uhlenbroich et al., "Abstract 0000: NKp46 engaging Bicycle NK-TICA™ drives tumor targeted cytotoxicity", PEGS Boston, May 17, 2023, 1 page.
Uhlenbroich, "Bicycles—a modality for Tumor-Targeted Immune Cell Agonism", Antibody Engineering & Therapeutics, Jun. 12, 2023, 23 pages.
Upadhyaya et al., "Abstract 888: An integrative approach to optimize a synthetic EphA2-dependent CD137 agonist: Balancing potency, physiochemical properties, and pharmacokinetics to achieve robust anti-tumor activity", SITC, Nov. 12, 2021, 1 page.
Upadhyaya et al., "Anticancer immunity induced by a synthetic tumor-targeted CD137 agonist", 2021, 9(1):e001762, pp. 1-10.
Upadhyaya et al., "Discovery and Optimization of a Synthetic Class of Nectin-4-Targeted CD137 Agonists for Immuno-oncology", Molecular Cancer Therapeutics, 2022, 65:9858-9872.
Valko et al., "Application of biomimetic HPLC to estimate lipophilicity, protein and phospholipid binding of potential peptide therapeutics", ADMET and DMPK, 2018, 6(2):162-175.
Wagstaff et al., "An Assay for Periplasm Entry Advances the Development of Chimeric Peptide Antibiotics", ACS Infectious Diseases, 2020, 6(9):2355-2361.
Wallack et al., "Abstract P05: Investigating soluble Nectin-4 and EphA2 as cancer biomarkers in plasma", Bio-IT World, May 23, 2023, 1 page.
Walsh et al., "Abstract 5807: Bicycle Toxin Conjugates® for the treatment of solid tumors", American Association for Cancer Research Annual Meeting, Apr. 9, 2024, 1 page.
Wang et al., "Comprehensive Surfaceome Profiling to Identify and Validate Novel Cell-Surface Targets in Osteosarcoma", Molecular Cancer Therapeutics, Jun. 2022, 21(6):903-913.
Wang et al., "Integrative surfaceome profiling identifies immunotherapeutic targets in osteosarcoma and preclinical testing of BT1769, an MT1-MMP-targeted Bicycle® toxin conjugate, in osteosarcoma by the Pediatric Preclinical Testing Consortium (PPTC)", AACE Annual Meeting, Apr. 10-15 and May 17-21, 2021, 15 pages.
Xu et al., "The application of PK/PD modelling in the clinical development of BT5528—a novel toxin delivery platform", ACoP, Oct. 30-Nov. 2, 2022, 21 pages.
Zhang et al., "Characterization and application of three novel monoclonal antibodies against human 4-1BB: distinct epitopes of human 4-1BB on lung tumor cells and immune cells", Tissue Antigens, 2007, 70(6):470-479.
Zhang et al., "Propagated Perturbations from a Peripheral Mutation Show Interactions Supporting WW Domain Thermostability", Structure, Nov. 6, 2018, 26(11):1474-1485.
U.S. Appl. No. 18/424,386, Mudd et al., filed on Jan. 26, 2024.
U.S. Appl. No. 18/427,414, Beswick et al., filed on Jan. 30, 2024.
U.S. Appl. No. 18/742,691, Chen, filed on Jun. 13, 2024.
"Bicycle Therapeutics Investor Presentation", Retrieved from: https://investors.bicycletherapeutics.com/static-files/f456c054-95c8-4e19-a62a-fcf5feb0650b, Aug. 2024, 61 pages.
Hadjicharalambous et al., "Investigating Penetration and Antimicrobial Activity of Vector Bicycle Conjugates", ACS Infectious Diseases, Jun. 12, 2024, 10(7):2381-2389.
Park et al., "Abstract 3756: Small Synthetic, Multivalent Bicyclic Peptides That Activate T Cell Costimulatory Protein CD137", Cancer Res., Jul. 1, 2018, 78(13_Supplement):3756, 2 pages.
Zapun et al., "Penicillin-binding proteins and Beta-lactam resistance", FEMS Microbiology Reviews, 2008, 32 (2):361-385.
U.S. Appl. No. 18/906,616, Beswick et al., filed on Oct. 4, 2024.

A

B

BICYCLIC PEPTIDE LIGANDS SPECIFIC FOR MT1-MMP

CROSS REFERENCE TO RELATED APPLICATIONS

This application is a continuation of U.S. application Ser. No. 17/443,222, filed Jul. 22, 2021, which is a continuation of U.S. application Ser. No. 16/705,446, filed Dec. 6, 2019, now U.S. Pat. No. 11,103,591, which is a divisional application of U.S. application Ser. No. 15/523,266, filed Apr. 28, 2017, now U.S. Pat. No. 10,532,106, which is a U.S. national stage application under 35 U.S. C. § 371 of International Application No. PCT/GB2015/053247, filed Oct. 29, 2015, which claims priority to United Kingdom Application No. 1515245.7, filed Aug. 27, 2015, and United Kingdom Application No. 1419237.1, filed Oct. 29, 2014, the entire contents of each of which are hereby incorporated herein by reference in their entirety.

SEQUENCE LISTING

The instant application contains a Sequence Listing which has been submitted electronically in XML format and is hereby incorporated by reference in its entirety. Said XML copy, created on Jul. 6, 2023, is named 392664-022USD1C2_199833_SL.xml and is 92,674 bytes in size.

FIELD OF THE INVENTION

The present invention relates to polypeptides which are covalently bound to molecular scaffolds such that two or more peptide loops are subtended between attachment points to the scaffold. In particular, the invention describes peptides which are high affinity binders of membrane type 1 metalloprotease (MT1-MMP). The invention also describes drug conjugates comprising said peptides, conjugated to one or more effector and/or functional groups which have utility in imaging and targeted cancer therapy.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^{2-}$; Wu et al. (2007), Science 330, 1066-71), a cyclic peptide with the Arg-Gly-Asp motif binding to integrin αVb3 (355 Å$^2$) (Xiong et al. (2002), Science 296 (5565), 151-5) or the cyclic peptide inhibitor upain-1 binding to urokinase-type plasminogen activator (603 Å$^{2-}$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), Chem-BioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and W02009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule (tris-(bromomethyl)benzene).

SUMMARY OF THE INVENTION

According to a first aspect of the invention, there is provided a peptide ligand specific for MT1-MMP comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein the peptide ligand comprises an amino acid sequence of formula (I):

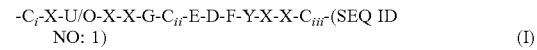

(I)

or a modified derivative, or pharmaceutically acceptable salt, thereof;

wherein:

$C_i$, $C_{ii}$ and $C_{iii}$ represent first, second and third cysteine residues, respectively;

X represents any amino acid residue;

U represents a polar, uncharged amino acid residue selected from N, C, Q, M, S and T; and O represents a non-polar aliphatic amino acid residue selected from G, A, I, L, P and V.

According to a further aspect of the invention, there is provided a drug conjugate comprising a peptide ligand as defined herein conjugated to one or more effector and/or functional groups, such as a cytotoxic agent, in particular DM1 and MMAE.

According to a further aspect of the invention, there is provided a conjugate comprising a peptide ligand as defined herein conjugated to one or more effector and/or functional groups, such as a radionuclide bearing chelator group, in particular DOTA.

According to a further aspect of the invention, there is provided a pharmaceutical composition comprising a peptide ligand or a drug conjugate as defined herein in combination with one or more pharmaceutically acceptable excipients.

According to a further aspect of the invention, there is provided a peptide ligand as defined herein for use in preventing, suppressing or treating cancer, in particular solid tumours such as non-small cell lung carcinomas.

DETAILED DESCRIPTION OF THE INVENTION

Figure 1:
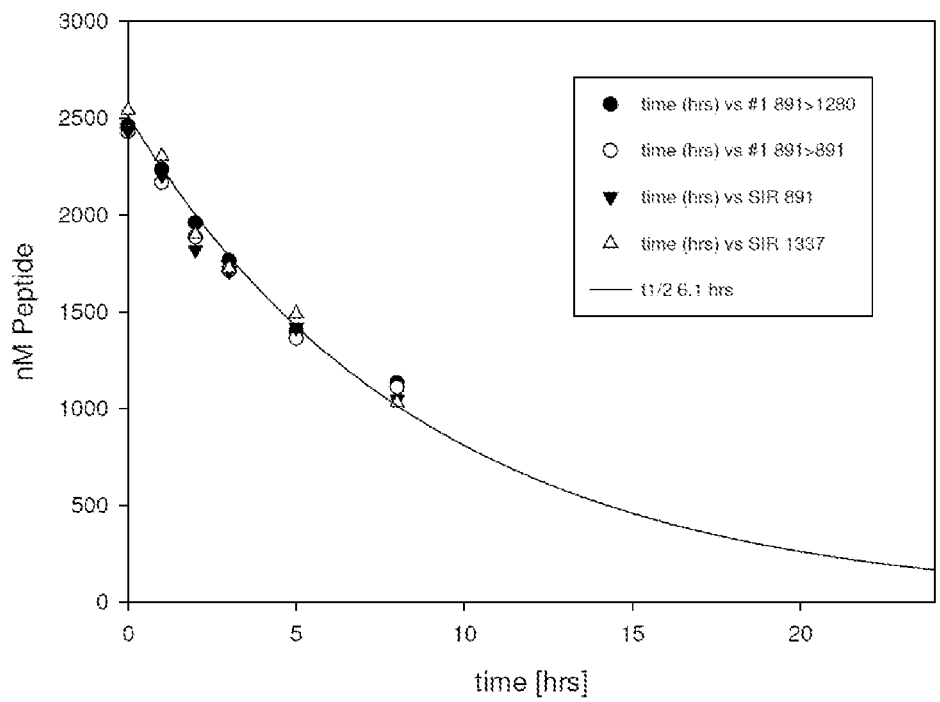
FIG. 1: Mouse Plasma Stability of 17-69-07-N219. Several ions were monitored as indicated in the legend, as well as two transitions in MRM mode. There is an excellent correlation between the ions. The half-life of the peptide in mouse plasma at 37° C. is 6 hours.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) 4$^{th}$ ed., John Wiley & Sons, Inc.), which are incorporated herein by reference.

Nomenclature

Numbering

When referring to amino acid residue positions within compounds of formula (I), cysteine residues ($C_i$, $C_{ii}$ and $C_{iii}$) are omitted from the numbering as they are invariant, therefore, the numbering of amino acid residues within the compound of formula (I) is referred to as below:

(SEQ ID NO: 1)
-$C_i$-$X_1$-U/$O_2$-$X_3$-$X_4$-$G_5$-$C_{ii}$-$E_6$-$D_7$-$F_8$-$Y_9$-$X_{10}$-$X_{11}$-$C_{iii}$-.

For the purpose of this description, all bicyclic peptides are assumed to be cyclised with TBMB (1,3,5-tris(bromomethyl)benzene) yielding a tri-substituted 1,3,5-trismethylbenzene structure. Cyclisation with TBMB occurs on $C_i$, $C_{ii}$, and $C_{iii}$.

Bicyclic Peptide Core Sequence

Each bicyclic peptide disclosed herein has been assigned a unique core sequence number which is defined as the amino acid sequence between the first N-terminal Cysteine ($C_i$) and the last C-terminal Cysteine ($C_{iii}$). In the example of the identifier 17-69-07, the core sequence is $C_i$YNEFG$C_{ii}$-iEDFYDI$C_{iii}$ (SEQ ID NO: 2), and is referred to as "17-69-07" or "(17-69-07)".

Peptide Code

Certain bicyclic peptides disclosed herein have also been assigned a unique identifier using a peptide code, such as 17-69-07-N241, wherein N241 denotes a particular derivative of the 17-69-07 bicycle core sequence. Different derivatives of 17-69-07 have different N-numbers, i.e. N001, N002, Nxxx.

Molecular Format

N- or C-terminal extensions to the bicycle core sequence are added to the left or right side of the core sequence, separated by a hyphen. For example, an N-terminal βAla-Sar10-Ala tail would be denoted as:

βAla-Sar10-A-(17-69-07)

and has the full sequence of βAla-Sar10-A-CYNEFGCEDFYDIC (SEQ ID NO: 3).

Modifications

Non-natural amino acid substitutions within the bicycle core sequence are indicated after the Molecular Format description. For example, if Tyrosine 1 in 17-69-07 is substituted with D-Alanine, the description is (17-69-07) D-Ala1, and the full sequence would be described as (SEQ ID NO: 4)
C(D-Ala1)NEFGCEDFYDIC.

If an N-terminal or C-terminal tail is attached to a bicyclic peptide that also contains modifications to the core sequence, then, by using 17-69-07-N241 as an example, the Molecular Format description is:

βAla-Sar10-A-(17-69-07) DAla1 1NAl4 DAla5 tBu-Gly11.

The full amino acid sequence of 17-69-07-N241 is therefore:

(SEQ ID NO: 5)
βAla-Sar10-A-C(D-Ala)NE(1Nal)(D-Ala)CEDFYD(tBuGly)
C.

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as $C_i$, $C_{ii}$ and $C_{iii}$), and form at least two loops on the scaffold.

Figure 8:
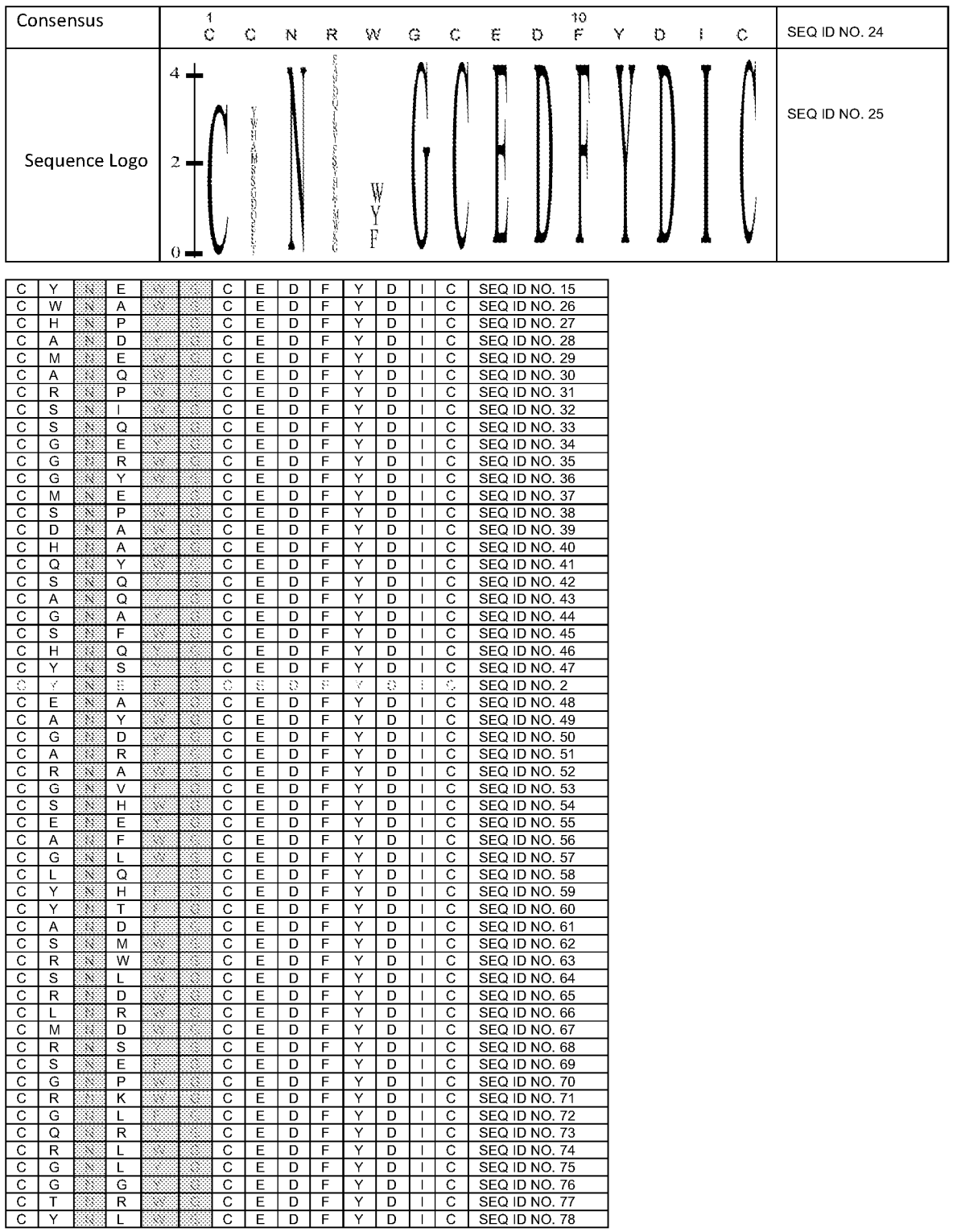
FIG. 8: List of sequence outputs derived from affinity maturations using libraries with fixed loop 2 residues of 17-69. The sequence logo plot on the right shows the overall preference of the residues in loop1 residues 1, 2, 3, 4 and 5.

It will be appreciated by the skilled person that the X at positions 1, 3, 4, 10 and 11 of formula (I) may represent any amino acid following the results of the alanine scan (see Table 5) and selection outputs (FIG. 8) which permits well tolerated substitutions at these positions.

In one embodiment, the X at position 1 of formula (I) is selected from any one of the following amino acids: Y, M, F or V. In a further embodiment, the X at position 1 of formula (I) is selected from Y, M or F. In a yet further embodiment, the X at position 1 of formula (I) is selected from Y or M. In a still yet further embodiment, the X at position 1 of formula (I) is selected from Y.

In one embodiment, the U/O at position 2 of formula (I) is selected from a U, such as an N. In an alternative embodiment, the U/O at position 2 of formula (I) is selected from an O, such as a G.

In one embodiment, the X at position 3 of formula (I) is selected from U or Z, wherein U represents a polar, uncharged amino acid residue selected from N, C, Q, M, S and T and Z represents a polar, negatively charged amino acid residue selected from D or E. In a further embodiment, the U at position 3 of formula (I) is selected from Q. In an alternative embodiment, the Z at position 3 of formula (I) is selected from E.

In one embodiment, the X at position 4 of formula (I) is selected from J, wherein J represents a non-polar aromatic amino acid residue selected from F, W and Y. In a further embodiment, the J at position 4 of formula (I) is selected from F. In alternative embodiment, the J at position 4 of formula (I) is selected from Y. In alternative embodiment, the J at position 4 of formula (I) is selected from W.

In one embodiment, the X at position 10 of formula (I) is selected from Z, wherein Z represents a polar, negatively charged amino acid residue selected from D or E. In one embodiment, the Z at position 10 of formula (I) is selected from D.

In one embodiment, the X at position 11 of formula (I) is selected from O, wherein O represents a non-polar aliphatic amino acid residue selected from G, A, I, L, P and V. In one embodiment, the O at position 11 of formula (I) is selected from I.

In one embodiment, the compound of formula (I) is a compound of formula (Ia):

(Ia)

(SEQ ID NO: 6)
-$C_i$-Y/M/F/V-U/O-U/Z-J-G-$C_{ii}$-E-D-F-Y-Z-O-$C_{iii}$-;

wherein U, O, J and Z are as defined hereinbefore.

In one embodiment, the compound of formula (I) is a compound of formula (Ib):

(Ib)

(SEQ ID NO: 7)
-$C_i$-Y/M/F/V-N/G-E/Q-F-G-$C_{ii}$-E-D-F-Y-D-I-$C_{iii}$-.

In one embodiment, the compound of formula (I) is a compound of formula (Ic):

(Ic)

(SEQ ID NO: 8)
-$C_i$-Y/M/F-N/G-E/Q-F-G-$C_{ii}$-E-D-F-Y-D-I-$C_{iii}$-.

In one embodiment, the compound of formula (I) is a compound of formula (Id):

(Id)

(SEQ ID NO: 9)
-$C_i$-Y/M-N-E/Q-F-G-$C_{ii}$-E-D-F-Y-D-I-$C_{iii}$-.

In one embodiment, the compound of formula (I) is a compound of formula (Ie):

(Ie)

(SEQ ID NO: 2)
-$C_i$-Y-N-E-F-G-$C_{ii}$-E-D-F-Y-D-I-$C_{iii}$- (17-69-07).

In a yet further embodiment, the peptide of formula (I) comprises a sequence selected from:

(SEQ ID NO: 2)
-$C_i$-Y-N-E-F-G-$C_{ii}$-E-D-F-Y-D-I-$C_{iii}$- (17-69-07);

(SEQ ID NO: 10)
-$C_i$-M-N-Q-F-G-$C_{ii}$-E-D-F-Y-D-I-$C_{iii}$- (17-69-12);

(SEQ ID NO: 11)
-$C_i$-F-G-E-F-G-$C_{ii}$-E-D-F-Y-D-I-$C_{iii}$- (17-69-02);

(SEQ ID NO: 12)
-$C_i$-V-N-E-F-G-$C_{ii}$-E-D-F-Y-D-I-$C_{iii}$- (17-69-03);

(SEQ ID NO: 13)
-$C_i$-F-N-E-F-G-$C_{ii}$-E-D-F-Y-D-I-$C_{iii}$- (17-69-04);

-$C_i$-Y-N-E-Y-G-$C_{ii}$-E-D-F-Y-D-I-$C_{iii}$- (17-69-07-N057); (SEQ ID NO: 14)
and -$C_i$-Y-N-E-W-G-$C_{ii}$-E-D-F-Y-D-I-$C_{iii}$- (17-69-44-N002). (SEQ ID NO: 15)

The peptides of this embodiment were identified to be potent candidates following affinity maturation against the hemopexin domain of MT1-MMP (see Example 1 and Tables 1 and 8).

In a still yet further embodiment, the peptide of formula (I) comprises a sequence selected from:

-$C_i$-Y-N-E-F-G-$C_{ii}$-E-D-F-Y-D-I-$C_{iii}$- (17-69-07); (SEQ ID NO: 2)

-$C_i$-M-N-Q-F-G-$C_{ii}$-E-D-F-Y-D-I-$C_{iii}$- (17-69-12). (SEQ ID NO: 10)

The peptides of this embodiment were identified to be the highest affinity candidates following affinity maturation against the hemopexin domain of MT1-MMP, synthesis of the core bicycle sequences, and quantitative measurement of affinities using competition experiments (see Example 1 and Tables 1-3).

In a still yet further embodiment, the peptide of formula (I) comprises a sequence selected from -$C_i$-Y-N-E-F-G-$C_{ii}$-E-D-F-Y-D-I-$C_{iii}$- (17-69-07) (SEQ ID NO: 2). The peptide of this embodiment was identified to be the most potent, and stable member of the family of peptide ligands within formula (I) (see Examples 1 to 4).

In one embodiment, certain peptide ligands of the invention are fully cross-reactive with murine, dog, cynomolgus and human MT1-MMP. In a further embodiment, the specifically exemplified peptide ligands of the invention are fully cross-reactive with murine, dog, cynomolgus and human MT1-MMP. For example, data is presented herein which demonstrates that both non-stabilised and stabilised derivatives of 17-69-07 (i.e. 17-69-07-N219 and 17-69-07-N241) are fully cross reactive (see Table 13).

In a yet further embodiment, the peptide ligand of the invention is selective for MT1-MMP, but does not cross-react with MMP-1, MMP-2, MMP-15 and MMP-16. Data is presented herein which demonstrates that the 17-69-07 core sequence, and the stabilised variant 17-69-07-N258, are uniquely selective for MT1-MMP (see Table 14).

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:
  Species cross-reactivity. This is a typical requirement for preclinical pharmacodynamics and pharmacokinetic evaluation;
  Protease stability. Bicyclic peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;
  Desirable solubility profile. This is a function of the proportion of charged and hydrophilic versus hydrophobic residues and intra/inter-molecular H-bonding, which is important for formulation and absorption purposes; and
  An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent.

Pharmaceutically Acceptable Salts

It will be appreciated that salt forms are within the scope of this invention, and references to compounds of formula (I) include the salt forms of said compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and Mg$^{2+}$, and other cations such as Al$^{3+}$ or Zn$^+$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the compounds of formula (I) contain an amine function, these may form quaternary ammonium salts, for example by reaction with an alkylating agent according to methods well known to the skilled person. Such quaternary ammonium compounds are within the scope of formula (I).

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyn-group bearing amino acids that allow functionalisation with alkyn or azide-bearing moieties, respectively.

In one embodiment, the modified derivative comprises a modification at amino acid position 1 and/or 9. Data is presented herein which shows that these positions, especially where tyrosine is present, are most susceptible to proteolytic degradation.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group, such as 17-69-07-N004 disclosed herein. In this embodiment, the N-terminal cysteine group (the group referred to herein as C$_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target, such as an Ala, G-Sar10-A or bAla-Sar10-A group. Data is presented herein which shows that addition of these groups to the bicyclic peptide 17-69-07 does not alter potency to the target protein (Tables 11-12).

In a further embodiment, the modified derivative comprises a C-terminal modification. In a further embodiment, the C-terminal modification comprises an amide group. In this embodiment, the C-terminal cysteine group (the group referred to herein as C$_{iii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the non-natural amino acid residue is substituted at position 4. Data is presented herein which shows that a number of non-natural amino acid residues are well tolerated at this position (see Table 8). In a further embodiment, the non-natural amino acid residues, such as those present at position 4, are selected from: 1-naphthylalanine; 2-naphthylalanine; cyclohexylglycine, phenylglycine; tert-butylglycine; 3,4-dichlorophenylalanine; cyclohexylalanine; and homophenylalanine.

In a yet further embodiment, the non-natural amino acid residues, such as those present at position 4, are selected from: 1-naphthylalanine; 2-naphthylalanine; and 3,4-dichlorophenylalanine. Data is presented herein which shows that these substitutions enhanced the affinity compared to the unmodified wildtype sequence (see Table 8).

In a yet further embodiment, the non-natural amino acid residues, such as those present at position 4, are selected from: 1-naphthylalanine. Data is presented herein which shows that this substitution provided the greatest level of enhancement of affinity (greater than 7 fold) compared to wildtype (see Table 8).

In one embodiment, the non-natural amino acid residue is introduced at position 9 and/or 11. Data is presented herein which shows that a number of non-natural amino acid residues are well tolerated at these positions (see Table 9).

In a further embodiment, the non-natural amino acid residues, such as those present at positions 9, are selected from: 4-bromophenylalanine, pentafluoro-phenylalanine.

In a further embodiment, the non-natural amino acid residues, such as those present at positions 11, are selected from: tert-butylglycine.

In a yet further embodiment, the non-natural amino acid residues, such as those present at position 9, is selected from: 4-bromophenylalanine. Data is presented herein which shows alteration of the Tyr 9 proteolytic recognition point (see Table 9).

In a yet further embodiment, the non-natural amino acid residues, such as those present at position 11, is selected from: tert-butylglycine. Data is presented herein which shows enhancement of activity and strongly protects the vicinal amino acid backbone from proteolytic hydrolysis by steric obstruction (see Table 9).

In one embodiment, the modified derivative comprises a plurality of the above mentioned modifications, such as 2, 3, 4 or 5 or more modifications. In a further embodiment, the modified derivative comprises 2, 3, 4 or 5 or more of the following modifications, such as all of the following 5 modifications: D-alanine at position 1 and 5, a 1-naphthyl-alanine at position 4, a 4-bromophenylalanine at position 9 and a tert-butylglycine at position 11. Data is presented herein which shows that this multi-substitution (17-69-07-N252; 17-69-07-N244 and 17-69-07-N255) is tolerated in concert with potency which is superior to wildtype (see Tables 10-12). In a yet further embodiment, the modified derivative comprises the following modifications: D-alanine at position 1 and 5, a 1-naphthylalanine at position 4 and a tert-butylglycine at position 11. Data is presented herein which shows that this multi-substitution (17-69-07-N239) is tolerated in concert with potency which is superior to wildtype (see Table 11).

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naph-thylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In a further embodiment, the amino acid residue at position 1 is substituted for a D-amino acid, such as D-alanine. Data is presented herein which demonstrates retention of potency without the consequent degradation (see Table 6).

In a further embodiment, the amino acid residue at position 5 is substituted for a D-amino acid, such as D-alanine or D-arginine. Data is presented herein which demonstrates retention of potency without the consequent degradation (see Table 7).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons. (for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled compounds of the invention, i.e. compounds of formula (I), wherein one or more atoms are replaced by atoms having the same atomic number, but an atomic mass or mass number different from the atomic mass or mass number usually found in nature, and compounds of formula (I), wherein metal chelating groups are attached (termed "effector") that are capable of holding relevant (radio)isotopes, and compounds of formula (I), wherein certain functional groups are covalently replaced with relevant (radio)isotopes or isotopically labelled functional groups.

Examples of isotopes suitable for inclusion in the compounds of the invention comprise isotopes of hydrogen, such as $^{2}H$ (D) and $^{3}H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, sulfur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled compounds of formula (I), for example, those incorporating a radioactive isotope, are useful in drug and/or substrate tissue distribution studies, and to clinically assess the presence and/or absence of the MT1-MMP target on diseased tissues such as tumours and elsewhere. The compounds of formula (I) can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}$H (T), and carbon-14, i.e. $^{14}$C, are particularly useful for this purpose in view of their ease of incorporation and ready means of detection.

Substitution with heavier isotopes such as deuterium, i.e. $^{2}$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Incorporation of isotopes into metal chelating effector groups, such as $^{64}$Cu, $^{67}$Ga, $^{68}$Ga, and $^{177}$Lu can be useful for visualizing tumour specific antigens employing PET or SPECT imaging. In particular, such biodistribution data is presented herein in Example 3.

Incorporation of isotopes into metal chelating effector groups, such as, but not limited to $^{90}$Y, $^{177}$Lu, and $^{213}$Bi, can present the option of targeted radiotherapy, whereby metal-chelator—bearing compounds of formula (I) carry the therapeutic radionuclide towards the target protein and site of action.

Isotopically-labeled compounds of formula (I) can generally be prepared by conventional techniques known to those skilled in the art or by processes analogous to those described in the accompanying Examples using an appropriate isotopically-labeled reagent in place of the non-labeled reagent previously employed.

Binding Activity

Specificity, in the context herein, refers to the ability of a ligand to bind or otherwise interact with its cognate target to the exclusion of entities which are similar to the target. For example, specificity can refer to the ability of a ligand to inhibit the interaction of a human enzyme, but not a homologous enzyme from a different species. Using the approach described herein, specificity can be modulated, that is increased or decreased, so as to make the ligands more or less able to interact with homologues or paralogues of the intended target. Specificity is not intended to be synonymous with activity, affinity or avidity, and the potency of the action of a ligand on its target (such as, for example, binding affinity or level of inhibition) are not necessarily related to its specificity.

Binding activity, as used herein, refers to quantitative binding measurements taken from binding assays, for example as described herein. Therefore, binding activity refers to the amount of peptide ligand which is bound at a given target concentration.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example, as known in the art as referred to above. In the present invention, the peptide ligands can be capable of binding to two or more targets and are therefore multispecific. Suitably, they bind to two targets, and are dual specific. The binding may be independent, which would mean that the binding sites for the targets on the peptide are not structurally hindered by the binding of one or other of the targets. In this case, both targets can be bound independently. More generally, it is expected that the binding of one target will at least partially impede the binding of the other.

There is a fundamental difference between a dual specific ligand and a ligand with specificity which encompasses two related targets. In the first case, the ligand is specific for both targets individually, and interacts with each in a specific manner. For example, a first loop in the ligand may bind to a first target, and a second loop to a second target. In the second case, the ligand is non-specific because it does not differentiate between the two targets, for example by interacting with an epitope of the targets which is common to both.

In the context of the present invention, it is possible that a ligand which has activity in respect of, for example, a target and an orthologue, could be a bispecific ligand. However, in one embodiment the ligand is not bispecific, but has a less precise specificity such that it binds both the target and one or more orthologues. In general, a ligand which has not been selected against both a target and its orthologue is less likely to be bispecific due to the absence of selective pressure towards bispecificity. The loop length in the bicyclic peptide may be decisive in providing a tailored binding surface such that good target and orthologue cross-reactivity can be obtained, while maintaining high selectivity towards less related homologues.

If the ligands are truly bispecific, in one embodiment at least one of the target specificities of the ligands will be common amongst the ligands selected, and the level of that specificity can be modulated by the methods disclosed herein. Second or further specificities need not be shared, and need not be the subject of the procedures set forth herein.

A target is a molecule or part thereof to which the peptide ligands bind or otherwise interact with. Although binding is seen as a prerequisite to activity of most kinds, and may be an activity in itself, other activities are envisaged. Thus, the present invention does not require the measurement of binding directly or indirectly.

The molecular scaffold is any molecule which is able to connect the peptide at multiple points to impart one or more structural features to the peptide. Preferably, the molecular scaffold comprises at least three attachment points for the peptide, referred to as scaffold reactive groups. These groups are capable of reacting with the cysteine residues ($C_i$, $C_{ii}$ and $C_{iii}$) on the peptide to form a covalent bond. They do not merely form a disulphide bond, which is subject to reductive cleavage and concomitant disintegration of the molecule, but form stable, covalent thioether linkages. Preferred structures for molecular scaffolds are described below.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment the molecular scaffold may be, or may be based on, natural monomers such as nucleosides, sugars, or steroids. For example the molecular scaffold may comprise a short polymer of such entities, such as a dimer or a trimer.

In one embodiment the molecular scaffold is a compound of known toxicity, for example of low toxicity. Examples of suitable compounds include cholesterols, nucleotides, steroids, or existing drugs such as tamazepam.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of tris(bromomethyl)benzene, especially 1,3,5-tris(bromomethyl)benzene ('TBMB'), or a derivative thereof.

In one embodiment, the molecular scaffold is 2,4,6-tris (bromomethyl)mesitylene. This molecule is similar to 1,3, 5-tris(bromomethyl)benzene but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene (the scaffold reactive group exemplified by TBMB) or iodoacetamide. Other scaffold reactive groups that are used to selectively couple compounds to cysteines in proteins are maleimides. Examples of maleimides which may be used as molecular scaffolds in the invention include: tris-(2-maleimidoethyl) amine, tris-(2-maleimidoethyl)benzene, tris-(maleimido) benzene. Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Effector and Functional Groups

According to a further aspect of the invention, there is provided a drug conjugate comprising a peptide ligand as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains.

An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of Drosophila (Antennapedia), e.g. as described in Chen and Harrison, Biochemical Society Transactions (2007) Volume 35, part 4, p821; Gupta et al. in Advanced Drug Discovery Reviews (2004) Volume 57 9637. Examples of short peptides which have been shown to be efficient at translocation through plasma membranes include the 16 amino acid penetratin peptide from Drosophila Antennapedia protein (Derossi et al (1994) J Biol. Chem. Volume 269 p10444), the 18 amino acid 'model amphipathic peptide' (Oehlke et al (1998) Biochim Biophys Acts Volume 1414 p127) and arginine rich regions of the HIV TAT protein. Non peptidic approaches include the use of small molecule mimics or SMOCs that can be easily attached to biomolecules (Okuyama et al (2007) Nature Methods Volume 4 p153). Other chemical strategies to add guanidinium groups to molecules also enhance cell penetration (Elson-Scwab et al (2007) J Biol Chem Volume 282 p13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

RGD peptides, which bind to integrins which are present on many cells, may also be incorporated.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half life in the range 12 to 60 hours. In a further embodiment, it will have a tβ half-life of a day or more. In a further embodiment still, it will be in the range 12 to 26 hours.

In one particular embodiment of the invention, the functional group is selected from a metal chelator, which is suitable for complexing metal radioisotopes of medicinal relevance. Such effectors, when complexed with said radioisotopes, can present useful agents for cancer therapy. Suitable examples include DOTA, NOTA, EDTA, DTPA, HEHA, SarAr and others (Targeted Radionuclide therapy, Tod Speer, Wolters/Kluver Lippincott Williams & Wilkins, 2011).

Possible effector groups also include enzymes, for instance such as carboxypeptidase G2 for use in enzyme/prodrug therapy, where the peptide ligand replaces antibodies in ADEPT.

In one particular embodiment of the invention, the functional group is selected from a drug, such as a cytotoxic agent for cancer therapy. Suitable examples include: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin, calicheamycins, and others.

In one further particular embodiment of the invention, the cytotoxic agent is selected from maytansinoids (such as DM1) or monomethyl auristatins (such as MMAE).

DM1 is a cytotoxic agent which is a thiol-containing derivative of maytansine and has the following structure:

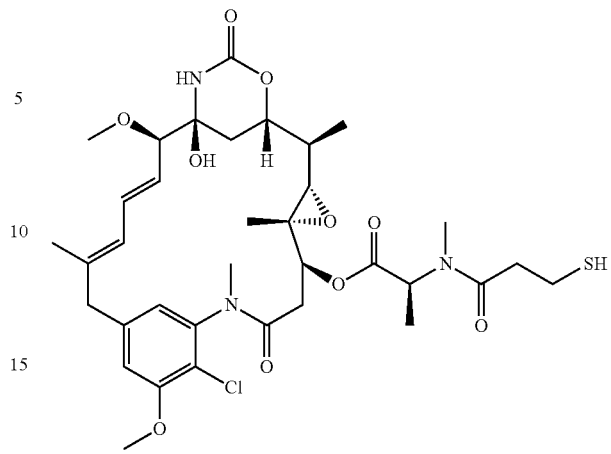

Monomethyl auristatin E (MMAE) is a synthetic antineoplastic agent and has the following structure:

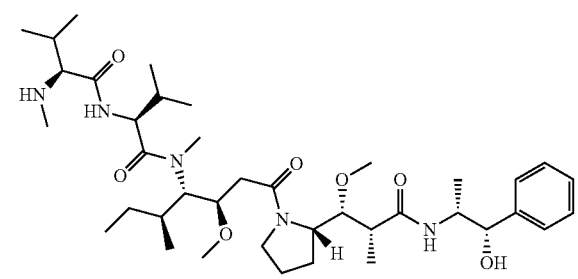 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

Data is presented herein in Examples 4 and 5 which demonstrates the effects of peptide ligands conjugated to toxins containing DM1 or MMAE.

In one embodiment, the cytotoxic agent is linked to the bicyclic peptide by a cleavable bond, such as a disulphide bond or a protease sensitive bond. In a further embodiment, the groups adjacent to the disulphide bond are modified to control the hindrance of the disulphide bond, and by this the rate of cleavage and concomitant release of cytotoxic agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on either the targeting entity (here, the bicyclic peptide) or toxin side of the molecular construct.

Thus, in one embodiment, the cytotoxic agent is a maytansinoid selected from a compound of formula (II):

(II)

wherein n represents an integer selected from 1 to 10; and $R_1$ and $R_2$ independently represent hydrogen, $C_{1-6}$ alkyl or a carbocyclyl or heterocyclyl group.

The term $C_{1-6}$ alkyl as used herein refers to a linear or branched saturated hydrocarbon group containing from 1 to 6 carbon atoms, respectively. Examples of such groups include methyl, ethyl, n-propyl, isopropyl, n-butyl, isobutyl, sec-butyl, tert butyl, n-pentyl, isopentyl, neopentyl or hexyl and the like.

The term "heterocyclyl" and "carbocyclyl" as used herein shall, unless the context indicates otherwise, include both aromatic and non-aromatic ring systems. Thus, for example, the term "heterocyclyl group" and "carbocyclyl group" include within their scope aromatic, non-aromatic, unsaturated, partially saturated and fully saturated carbocyclyl or heterocyclyl ring systems. In general, unless the context indicates otherwise, such groups may be monocyclic or bicyclic (including fused and bridged bicyclic groups) and may contain, for example, 3 to 12 ring members, more usually 5 to 10 ring members.

In one embodiment of the compound of formula (II), $R_1$ and $R_2$ independently represent hydrogen or methyl.

In one embodiment of the compound of formula (II), n represents 1 and $R_1$ and $R_2$ both represent hydrogen (i.e. the maytansine derivative DM1).

In an alternative embodiment of the compound of formula (II), n represents 2, $R_1$ represents hydrogen and $R_2$ represents a methyl group (i.e. the maytansine derivative DM3).

In one embodiment of the compound of formula (II), n represents 2 and $R_1$ and $R_2$ both represent methyl groups (i.e. the maytansine derivative DM4).

It will be appreciated that the cytotoxic agent of formula (II) can form a disulphide bond, and in a conjugate structure with a bicyclic peptide of formula (I), the disulphide connectivity between the thiol-toxin (II) and thiol-bicycle peptide (III) is introduced through several possible synthetic schemes, two being described in Scheme II or Scheme III.

In one embodiment, the bicyclic peptide component of the conjugate has the structure shown in formula (III):

(III)

wherein m represents an integer selected from 0 to 10, and $R_3$ and $R_4$ independently represent hydrogen, $C_{1-6}$ alkyl or a carbocyclyl or heterocyclyl group.

In one embodiment of the compound of formula (III), $R_3$ and $R_4$ independently represent hydrogen or methyl.

Compounds of formula (III) where $R_3$ and $R_4$ are both hydrogen are considered unhindered and compounds of formula (III) where one or all of $R_3$ and $R_4$ represent methyl are considered hindered.

It will be appreciated that the bicyclic peptide of formula (III) can form a disulphide bond, and in a conjugate structure with a cytotoxic agent of formula (II), the disulphide connectivity between the thiol-toxin (II) and thiol-bicycle peptide (III) is introduced through several possible synthetic schemes, one being described in Scheme II.

In one embodiment, the cytotoxic agent is linked to the bicyclic peptide by a linker defined in formula (IV):

(IV)

wherein $R_1$, $R_2$, $R_3$ and $R_4$ represent hydrogen, $C_{1-6}$ alkyl or a carbocyclyl or heterocyclyl group;

Toxin refers to any suitable cytotoxic agent defined herein;

Bicycle represents any suitable bicyclic peptide defined herein;

n represents an integer selected from 1 to 10; and m represents an integer selected from 0 to 10.

In one embodiment, $R_1$, $R_2$, $R_3$ and $R_4$ represent hydrogen or methyl.

When $R_1$, $R_2$, $R_3$ and $R_4$ are each hydrogen, the disulphide bond is least hindered and most susceptible to reduction. When $R_1$, $R_2$, $R_3$ and $R_4$ are each methyl, the disulphide bond is most hindered and least susceptible to reduction. Partial substitutions of hydrogen and methyl yield a gradual increase in resistance to reduction, and concomitant cleavage and release of toxin.

In one embodiment, the toxin of compound (IV) is a maytansine and the conjugate comprises a compound of formula (V):

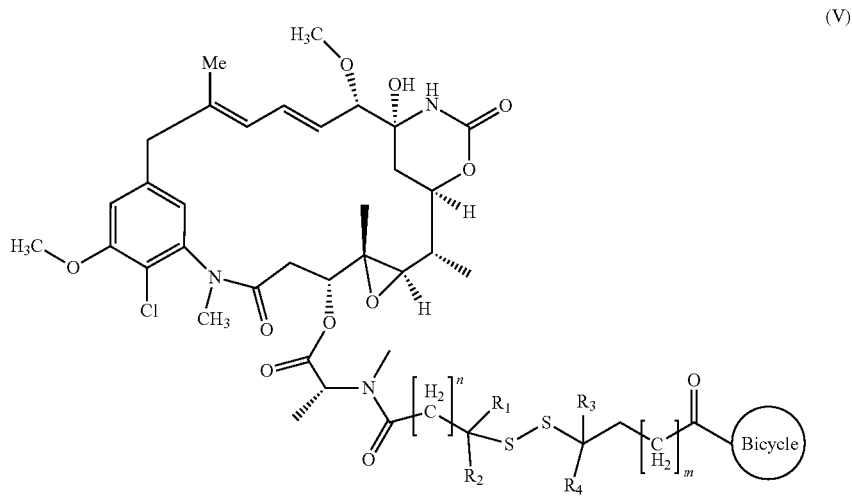

(V)

wherein $R_1$, $R_2$, $R_3$ and $R_4$ represent hydrogen, $C_{1-6}$ alkyl or a carbocyclyl or heterocyclyl group;
Bicycle represents any suitable bicyclic peptide as defined herein;
n represents an integer selected from 1 to 10; and
m represents an integer selected from 0 to 10.

In a further embodiment of the compound of formula (V), n represents 1 and $R_1$, $R_2$, $R_3$ and $R_4$ each represent hydrogen, i.e. a compound of formula (V)$^a$:

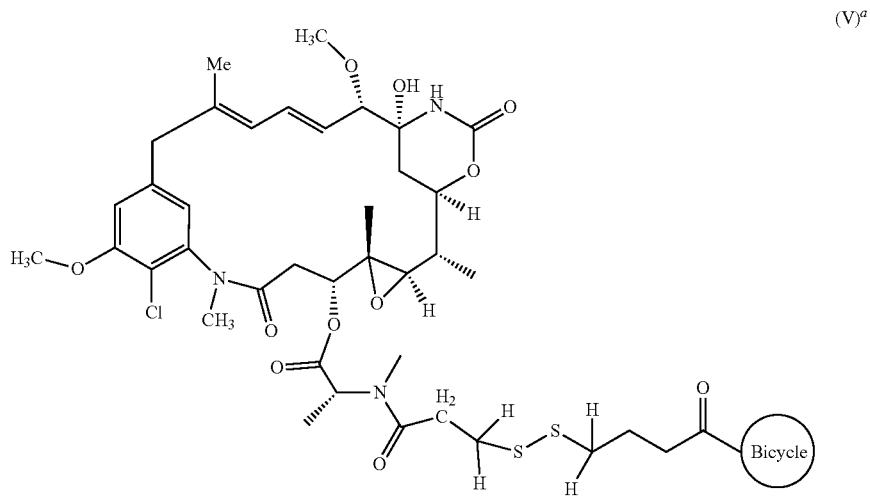 [SMILES: COc1cc2cc(c1Cl)N(C)C(=O)C[C@@H](OC(=O)[C@@H](C)N(C)C(=O)CCSSCCCC(C)=O)[C@@]1(C)O[C@@H]1[C@@H](C)[C@H]1C[C@](O)(NC(=O)O1)[C@@H](OC)/C=C/C=C(\C)C2]

(V)$^a$

The BDC of formula (V)$^a$ is known as BT17BDC-17. The unhindered disulphide in the BDC BT17BDC-17 is the equivalent of BT17BDC-9, whereby the difference resides in the bicyclic peptide portion: BT17BDC-9 employs the non-stabilised sequence (17-69-07-N219), while BT17BDC-17 employs the stabilised bicyclic peptide counterpart (17-69-07-N241) which is amide-bonded to the toxin-disulphide construct. This non-hindered derivative of the maytansine with n=1 is termed DM1.

In a further embodiment of the compound of formula (V), n represents 1, $R_1$ represents methyl and $R_2$, $R_3$ and $R_4$ each represent hydrogen, i.e. a compound of formula $(V)^b$:

$(V)^b$

The BDC of formula $(V)^b$ is known as BT17BDC-18 and contains a single hindering methyl group on the bicyclic peptide side, and in the antibody drug conjugate context produces a 7-fold reduction in its sensitivity to a reducing agent such as dithiothreitol (compared to the non-hindered disulphide) (Kellogg et al (2011) Bioconjugate Chemistry, 22, 717). The reduced sensitivity to reduction is correlated with a lower toxin release rate. This non-hindered derivative of the maytansine with n=1 is termed DM1. BT17BDC-18 employs the stabilised bicyclic peptide counterpart (17-69-07-N241) which is amide-bonded to the toxin-disulphide construct.

In a further embodiment of the compound of formula (V), n represents 2, $R_1$ and $R_2$ both represent hydrogen and $R_3$ and $R_4$ both represent methyl, i.e. a compound of formula $(V)^c$:

$(V)^c$

The BDC of formula (V)$^c$ is known as BT17BDC-19 and contains two hindering methyl groups on the maytansine side, and in the antibody drug conjugate context produces a 14-fold reduction in its sensitivity to a reducing agent such as dithiothreitol. The reduced sensitivity to reduction is correlated with a lower toxin release rate. This hindered derivative of the maytansine with n=2 is termed DM4. BT17BDC-19 employs the stabilised bicyclic peptide counterpart (17-69-07-N241) which is amide-bonded to the toxin-disulphide construct.

In a further embodiment of the compound of formula (V), n represents 2, $R_1$ and $R_3$ both represent methyl and $R_2$ and $R_4$ both represent hydrogen, i.e. a compound of formula (V)$^d$:

Example 5 and Tables 16 and 17 which demonstrates that these conjugates were considered suitable molecules for use in targeted cancer therapy.

In a further embodiment, the conjugate is selected from BT17BDC-17 (Compound of formula (V)$^a$), BT17BDC-18 (Compound of formula (V)$^b$) and BT17BDC-19 (Compound of formula (V)$^c$). Data is presented in Example 5 and Tables 16 and 17 which demonstrates that these conjugates are considered suitable molecules for use in targeted cancer therapy and are well tolerated at efficacious doses.

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

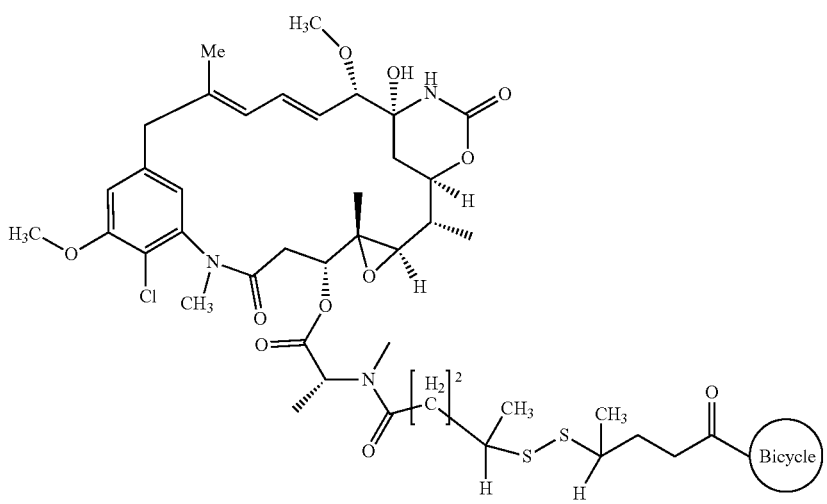

(V)$^d$

The BDC of formula (V)$^d$ is known as BT17BDC-20 and contains one hindering methyl group on the maytansine side, and one hindering methyl group on the bicycle peptide side, and in the antibody drug conjugate context produces a 170-fold reduction in its sensitivity to a reducing agent such as dithiothreitol. The reduced sensitivity to reduction is correlated with a lower toxin release rate. This hindered derivative of the maytansine with n=2 is termed DM3. BT17BDC-20 employs the stabilised bicyclic peptide counterpart (17-69-07-N241) which is amide-bonded to the toxin-disulphide construct.

Indeed, in the context of antibody drug conjugates, the balance of efficacy versus tolerability in the animal model showed that its optimum is associated with some level of hindrance, i.e. that of DM4 (Kellogg et al (2011) Bioconjugate Chemistry, 22, 717) which is present as such also in BT17BDC-19.

In one embodiment, the conjugate is selected from BT17BDC-9, BT17BDC-17 (Compound of formula (V)$^a$), BT17BDC-18 (Compound of formula (V)$^b$), BT17BDC-19 (Compound of formula (V)$^c$) and BT17BDC-20 (Compound of formula (V)$^d$). Data is presented in Example 5 and Tables 16 and 17 which demonstrate the beneficial properties of BT17BDC-9, BT17BDC-17, BT17BDC-18, BT17BDC-19 and BT17BDC-20.

In a further embodiment, the conjugate is selected from BT17BDC-9, BT17BDC-17 (Compound of formula (V)$^a$), BT17BDC-18 (Compound of formula (V)$^b$) and BT17BDC-19 (Compound of formula (V)$^c$). Data is presented in Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec 20; 91 (26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TBMB) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulfide—linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

According to a further aspect of the invention, there is provided a process for preparing a drug conjugate as defined herein which comprises the synthetic route described in any one of Schemes I, II or III.

Pharmaceutical Compositions

According to a further aspect of the invention, there is provided a pharmaceutical composition comprising a peptide ligand or a drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as high affinity binders of membrane type 1 metalloprotease (MT1-MMP, also known as MMP14). MT1-MMP is a transmembrane metalloprotease that plays a major role in the extracellular matrix remodeling, directly by degrading several of its components and indirectly by activating pro-MMP2. MT1-MMP is crucial for tumor angiogenesis (Sounni et al (2002) FASEB J. 16 (6), 555-564) and is over-expressed on a variety of solid tumours, therefore the MT1-MMP—binding bicycle peptides of the present invention have particular utility in the targeted treatment of cancer, in particular solid tumours such as non-small cell lung carcinomas. In one embodiment, the bicyclic peptide of the invention is specific for human MT1-MMP. In a further embodiment, the bicyclic peptide of the invention is specific for mouse MT1-MMP. In a yet further embodiment, the bicyclic peptide of the invention is specific for human and mouse MT1-MMP. In a yet further embodiment, the bicyclic peptide of the invention is specific for human, mouse and dog MT1-MMP.

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The effector group and conjugates of the peptide ligands of the present invention will typically find use in preventing, suppressing or treating cancer, in particular solid tumours such as non-small cell lung carcinomas.

Thus, according to a further aspect of the invention, there are provided effector groups and drug conjugates of the peptide ligand as defined herein for use in preventing, suppressing or treating cancer, in particular solid tumours such as non-small cell lung carcinomas.

According to a further aspect of the invention, there is provided a method of preventing, suppressing or treating cancer, in particular solid tumours such as non-small cell lung carcinomas which comprises administering to a patient in need thereof an effector group and drug conjugate of the peptide ligand as defined herein.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and pre-malignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas,leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Materials and Methods

Phage Selections

6×6 bicycle phage libraries were generated as described in Heinis et al (2009), Nat Chem Biol 5 (7), 502-507, WO 2009/098450, WO 2013/050615 and WO 2013/050616. Phage display selections were performed using said 6×6 phage library against the biotinylated human MT1-MMP hemopexin domain.

Protein Expression

The MT1-MMP hemopexin-like repeats (also known as the MT1-MMP hemopexin domain), residues Cys319—Gly511 from the human gene, were transiently expressed in HEK293 cells as secreted N-terminally His6-tagged (SEQ ID NO: 79) soluble protein, using the pEXPR-IBA42 (IBA)

expression vector. Following expression, the protein was purified by Nickel-NTA affinity chromatography followed by gel filtration, and purity was checked by SDS-PAGE. Batch to batch variability was also monitored by fluorescence thermal shift experiments in the presence/absence of a hemopexin domain binding bicycle.

Peptide Synthesis

Peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with the following side chain protecting groups: Arg(Pbf); Asn(Trt); Asp(OtBu); Cys(Trt); Glu(OtBu); Gln (Trt); His(Trt); Lys(Boc); Ser(tBu); Thr(tBu); Trp(Boc); and Tyr(tBu) (Sigma). The coupling reagent was HCTU (Pepceuticals), diisopropylethylamine (DIPEA, Sigma) was employed as a base, and deprotection was achieved with 20% piperidine in DMF (AGTC). Syntheses were performed using 0.37 mmol/gr Fmoc-Rink amide AM resin (AGTC), Fmoc-amino acids were utilised at a four-fold excess, and base was at a four-fold excess with respect to the amino acids. Amino acids were dissolved at 0.2M in DMSO, HCTU at 0.4M in DMF, and DIPEA at 1.6M in N-methylpyrrolidone (Alfa Aesar). Conditions were such that coupling reactions contained between 20 to 50% DMSO in DMF, which reduced aggregation and deletions during the solid phase synthesis and enhanced yields. Coupling times were generally 30 minutes, and deprotection times 2×5 minutes. Fmoc-N-methylglycine (Fmoc-Sar-OH, Merck) was coupled for 1 hr, and deprotection and coupling times for the following residue were 20 min and 1 hr, respectively. After synthesis, the resin was washed with dichloromethane, and dried. Cleavage of side-chain protecting groups and from the support was effected using 10 mL of 95:2.5:2.5:2.5 v/v/v/w TFA/H$_2$O/iPr 3 SiH/dithiothreitol for 3 hours. Following cleavage, the spent resin was removed by filtration, and the filtrate was added to 35 mL of diethylether that had been cooled at −80° C. Peptide pellet was centrifuged, the etheric supernatant discarded, and the peptide pellet washed with cold ether two more times. Peptides were then resolubilised in 5-10 mL acetonitrile-water and lyophilised. A small sample was removed for analysis of purity of the crude product by mass spectrometry (MALDI-TOF, Voyager DE from Applied Biosystems). Following lyophilisation, peptide powders were taken up in 10 mL 6 M guanidinium hydrochloride in H$_2$O, supplemented with 0.5 mL of 1 M dithiothreitol, and loaded onto a C8 Luna preparative HPLC column (Phenomenex). Solvents (H$_2$O, acetonitrile) were acidified with 0.1% heptafluorobutyric acid. The gradient ranged from 30-70% acetonitrile in 15 minutes, at a flowrate of 15-20 mL/min, using a Gilson preparative HPLC system. Fractions containing pure linear peptide material (as identified by MALDI) were combined, and modified with 1,3, 5-tris(bromomethyl)benzene (TBMB, Sigma). For this, linear peptide was diluted with H$_2$O up to ~35 mL, ~500 μL of 100 mM TBMB in acetonitrile was added, and the reaction was initiated with 5 mL of 1 M NH$_4$HCO$_3$ in H$_2$O. The reaction was allowed to proceed for ~30 –60 min at RT, and lyophilised once the reaction had completed (judged by MALDI). Following lyophilisation, the modified peptide was purified as above, while replacing the Luna C8 with a Gemini C18 column (Phenomenex), and changing the acid to 0.1% trifluoroacetic acid. Pure fractions containing the correct TMB-modified material were pooled, lyophilised and kept at −20° C. for storage.

All amino acids, unless noted otherwise, were used in the L-configurations.

DOTA was coupled to the peptide chain during solid phase peptide synthesis using the protected precursor DOTA (tBu)$_3$ (TCI, CAS 137076-54-1).

Non-natural amino acids were incorporated into peptide sequence using the general methods described above.

The list of non-natural amino acid precursors employed herein are summarised in the table below:

| Supplier | Short name | Full chemical name |
|---|---|---|
| AGTC | D-Asp | Fmoc-D-Asp(tBu)-OH |
| Iris Biotech | HPhe | Fmoc-L-Homophenylalanine |
| Alfa Aesar | 5FPhe | Fmoc-pentafluoro-L-phenylalanine |
| PolyPeptide Gropu | 4BrPhe | Fmoc-4-bromo-L-phenylalanine |
| Iris Biotech | B-Ala | Fmoc-beta-Ala-OH |
| Iris Biotech | 3Pal | Fmoc-L-3Pal-OH |
| Iris Biotech | 4Pal | Fmoc-L-4Pal-OH |
| Iris Biotech | D-Pro | Fmoc-D-Pro-OH |
| Merck Novabiochem | Aib | Fmoc-Aib-OH |
| Merck Novabiochem | D-Ala | Fmoc-D-Ala-OH |
| Merck Novabiochem | D-Arg | Fmoc-D-Arg(Pbf)-OH |
| Merck Novabiochem | D-Gln | Fmoc-D-Gln(Trt)-OH |
| Merck Novabiochem | D-His | Fmoc-D-His(Trt)-OH |
| Merck Novabiochem | Hyp | Fmoc-Hyp(tBu)-OH |
| Merck Novabiochem | D-Leu | Fmoc-D-Leu-OH |
| Merck Novabiochem | HArg | Fmoc-L-HArg(Boc)2-OH |
| Peptec Corporation | 4,4-BPAl | Fmoc-L-4,4'-Biphenylalanine |
| Peptech Corporation | 3,3-DPA | Fmoc-L-3,3-Diphenylalanine |
| Peptech Corporation | Dpg | Fmoc-Dipropylglycine |
| Peptech Corporation | 1NAl | Fmoc-L-1-Naphthylalanine |
| Peptech Corporation | 2NAl | Fmoc-L-2-Naphthylalanine |
| Peptech Corporation | Pip | Fmoc-L-Pipecolic acid |
| Polypeptide Group | Aze | Fmoc-L-azetidine-2-carboxylic acid |
| Polypeptide Group | Cha | Fmoc-beta-cyclohexyl-L-alanine |
| Polypeptide Group | 4FluoPro | (2S,4R)-Fmoc-4-fluoro-pyrrolidine-2-carboxylic acid |
| AGTC | D-Asp | Fmoc-D-Asp(tBu)-OH |
| Merck | tBuGly | Fmoc-α-tert-butylglycine |
| Iris Biotech | Chg | Fmoc-L-cyclohexylglycine |
| Fluorochem | Phg | Fmoc-Phenylglycine-OH |
| Iris Biotech | 3Pal | Fmoc-L-3Pal-OH |
| Iris Biotech | 4Pal | Fmoc-L-4Pal-OH |
| Merck Novabiochem | D-Leu | Fmoc-D-Leu-OH |
| Merck Novabiochem | HArg | Fmoc-L-HArg(Boc)2-OH |
| Polypeptide Group | 3,4 DCPhe | Fmoc-3,4-dichloro-L-phenylalanine |
| Polypeptide Group | Cha | Fmoc-beta-cyclohexyl-L-alanine |

Peptides used for the pharmacokinetic studies were lyophilised from 0.1% TFA in water to afford the TFA salts or free acids of the compounds.

Synthesis of BDCs Using 17-69-07-N219 as a Precursor Bicyclic Peptide

Two Bicycle Drug Conjugates (BDC) were synthesised, using 17-69-07-N219 as a precursor peptide. The activated vcMMAE or disulphide-DM1 constructs (dissolved in DMSO) were directly conjugated at 1.4× excess with 17-69-07-N219 in aqueous conditions (100 sodium phosphate pH8) (see Schemes I and II). Concentrations were at 9 mg/mL peptide or higher. The reaction was followed by LC/MS and judged complete after 3.5 hours. This was followed by standard reverse phase purification using a C18 semi-preparative column. Fractions at purity greater than 95% were isolated and lyophilised. The materials did not contain measurable quantities of free toxin. For the in vitro and in vivo studies, lyophilised powders were taken up as concentrated DMSO stocks (100 mg/mL), and diluted in the appropriate buffer for further use.

Synthesis of BDCs Using 17-69-07-N241 as a Precursor Bicyclic Peptide

For synthesis of BT17BDC-17, BT17BDC-18, BT17BDC-19 and BT17BDC-20, the following N-hydroxy succinimide esters (NHS esters) of disulphide maytansinoids were used:

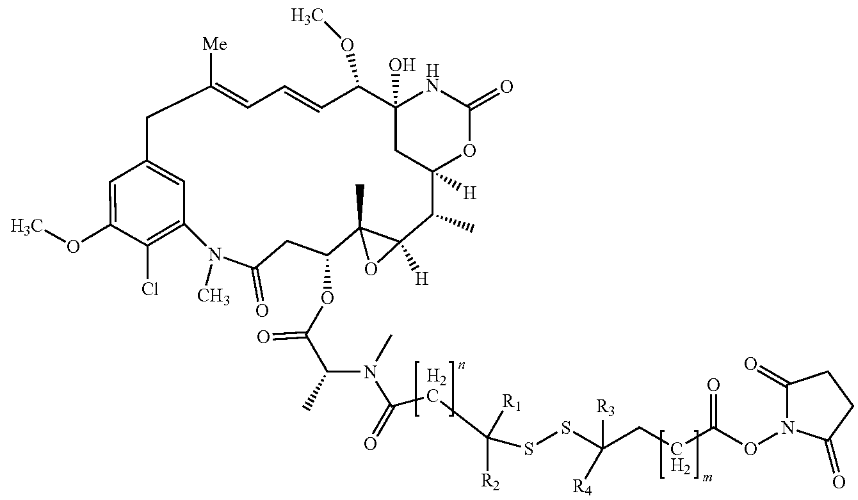

wherein $R_1$, $R_2$, $R_3$, $R_4$, m and n are as described hereinbefore for compounds of formula $(V)^a$, $(V)^b$, $(V)^c$, $(V)^d$ for BT17BDC-17, BT17BDC-18, BT17BDC-19 and BT17BDC-20, respectively.

BT17BDC-18 was further synthesised through an alternative route, as described below and in Scheme Ill. Here, 17-69-07-N277 was synthesised by reacting 17-69-07-N241 with SPP (N-succinimidyl 4-(2-pyridyldithio)pentanoate) in DMSO. Concentrations of 17-69-07-N241 were 10 mM or higher, with a 1.3 fold excess of SPP, and a 20-fold excess of diisopropylethylamine, at room temperature. The reaction was judged complete after 1 hour, as judged by LCMS. Purification was performed by reverse phase as described above. Appropriate fractions were lyophilised.

17-69-07-N277 was disulphide exchanged with 1.15 equivalents of DM1 (as the free thiol), in semi aqueous conditions (50% dimethylacetamide and 50% 100 mM sodium acetate pH 5.0 supplemented with 2 mM EDTA) for 21 hours at room temperature under a nitrogen gas blanket. Concentrations of 17-69-07-N277 in the reaction were at 10 mM or higher. This was followed by standard reverse phase purification using a C18 semi-preparative column. Fractions at purity greater than 95% were isolated and lyophilised. The materials did not contain measurable quantities of free toxin. For the in vitro and in vivo studies, lyophilised powders were solubilised in aqueous formulation as described above, or taken up directly in the appropriate buffer.

Dissociation Rate Constant Determination of Bicyclic Binders to MT1-MMP

Direct Binding Fluorescence Polarisation (Anisotropy) Assays

Direct Binding Fluorescence Polarisation or Anisotropy Assays are performed by titrating a constant concentration of fluorescent tracer (here, the fluoresceinated bicyclic peptide to be studied) with its binding partner (here, the MT1-MMP hemopexin domain). As the concentration of binding partner increases during the titration, the polarisation signal changes in proportion to the fraction of bound and unbound material. This allows determination of dissociation rates (Kd) quantitatively. Assay data can be fit using standard ligand binding equations.

Typically, concentrations of the tracer are ideally well below the Kd of the tracer:titrant pair, and concentrations chosen are usually at ~1 nM or less. The titrant (binding partner) concentration is varied from 0.1 nM up to typically 5 μM. The range is chosen such that the maximum change in fluorescent polarisation can be observed. Buffers employed are phosphate buffered saline in the presence of 0.01% Tween. Experiments were run in black 384 well low-bind/low volume plates (Corning 3820), and the fluorescent polarisation signal was measured using a BMG Pherastar FS plate reader.

Fluorescent tracers referred to in the text are bicyclic peptides that have been fluoresceinated using 5,6-carboxyfluorescein. Fluoresceination may be performed on the N-terminal amino group of the peptide, which is separated from the bicycle core sequence by a sarcosine spacer (usually Sar5). This can be done during Fmoc solid phase synthesis or post-synthetically (after cyclisation with TBMB and purification) if the N-terminal amino group is unique to the peptide. Fluoresceination can also be performed on the C-terminus, usually on a Lysine introduced as the first C-terminal residue, which is then separated from the bicycle core sequence by a sarcosine spacer (usually Sar6). Thus, N-terminal tracers can have a molecular format described as Fluo-Gly-Sar5-A(BicycleCoreSequence), and (BicycleCoreSequence)-A-Sar6-K(Fluo) for a C-terminally fluoresceinated construct. Fluorescent tracers used in the Examples are A-(17-69)-A-Sar6-K(Fluo), A-(17-69-07)-A-Sar6-K(Fluo), and A-(17-69-12)-A-Sar6-K(Fluo). Due to the acidic nature of the 17-69 fluorescent peptides, they were typically prepared as concentrated DMSO stocks, from which dilution were prepared in 100 mM Tris pH 8 buffer.

Competition Assays Using Fluorescence Polarisation (Anisotropy)

Due to their high affinities to the MT1-MMP Hemopexin domain (PEX), the fluoresceinated derivatives of 17-69-07 and 17-69-12 (denoted as 17-69-07-N040 and 17-69-12-N005, respectively) can be used for competition experiments (using FP for detection). Here, a pre-formed complex of PEX with the fluorescent PEX-binding tracer is titrated with free, non-fluoresceinated bicyclic peptide. Since all 17-69-based peptides are expected to bind at the same site, the titrant will displace the fluorescent tracer from PEX. Dissociation of the complex can be measured quantitatively, and the Kd of the competitor (titrant) to the target protein determined. The advantage of the competition method is that the affinities of non-fluoresceinated bicyclic peptides can be determined accurately and rapidly.

Concentrations of tracer are usually at the Kd or below (here, 1 nM), and the binding protein (here, hemopexin of MT1-MMP) is at a 15-fold excess such that >90% of the tracer is bound. Subsequently, the non-fluorescent competitor bicyclic peptide (usually just the bicycle core sequence) is titrated, such that it displaces the fluorescent tracer from the target protein. The displacement of the tracer is measured and associated with a drop in fluorescence polarisation. The drop in fluorescence polarisation is proportional to the fraction of target protein bound with the non-fluorescent titrant, and thus is a measure of the affinity of titrant to target protein.

The raw data is fit to the analytical solution of the cubic equation that describes the equilibria between fluorescent tracer, titrant, and binding protein. The fit requires the value of the affinity of fluorescent tracer to the target protein, which can be determined separately by direct binding FP experiments (see previous section). The curve fitting was performed using Sigmaplot 12.0 and used an adapted version of the equation described by Zhi-Xin Wang (FEBS Letters 360 (1995) 111-114).

Plasma Stability Profiling
Method #1

A rapid plasma stability profiling assay was developed that employed mass spectrometric detection (MALDI-TOF, Voyager DE, Applied Biosystems) of the parent mass as well as plasma-protease induced fragments thereof. By assessing the nature of the fragments, preferred cleavage sites can be determined. Here, a 1-1.5 mM peptide stock (in DMSO) was directly diluted into mouse/rat/human plasma (Sera labs, using citrate as anticoagulant), giving a final concentration of 50 μM peptide, and incubated for up to 48 hrs at 37° C. 5 μL samples were taken at appropriate time points and frozen at −80° C. For analysis, the samples were defrosted, mixed with 25 μL of 3:3:1 acetonitrile:methanol:water, and centrifuged at 13k for 5 min. 5 μL of the peptide-containing supernatant was aspirated and mixed with 30 mM ammonium bicarbonate in a 1:1 mixture of acetonitrile:$H_2O$. 1 μL of this was then spotted on the MALDI plate, dried, and Matrix (alpha-cyanocinnamic acid, Sigma, prepared as a saturated solution in 1:1 acetonitrile:water containing 0.1% trifluoroacetic acid) was layered over the sample (1 μL), dried and analysed using the MALDI TOF. It should be noted that this is a qualitative assay serves to detect comparative changes in plasma stability between different bicycle peptide sequences, and functions as an excellent tool to determine preferred cleavage sites.

Method #2

To obtain plasma stability of bicyclic peptides quantitatively, peptide stock solutions (200 μM in DMSO) were mixed with plasma (human or mouse), such that final concentrations were 10 μM. 40 μL samples were taken periodically up to 8 hrs and frozen at −80° C. Prior to LC-MS analysis, samples were defrosted, and mixed with 3 volumes (here, 120 μL) of 1:1 acetonitrile/MeOH water. The milky suspensions were centrifuged for 30 min at 13000 rpm, and peptide-containing supernatants were quantitated for doubly/triply charged species and MS/MS fragments thereof using a Waters Xevo TQ-D instrument, while using a plasma extracted standard curve of the same peptides as a reference. The half-life of degradation in plasma was used to assess the comparative stability of the molecules.

Pharmacokinetics of 17-69-07 in Mouse, Identification of Metabolites
Pharmacokinetics of 17-69-07-N004

Mouse pharmacokinetics were acquired using bicyclic peptide 17-69-04-N004, which was dosed to one group of 12 male CD1 mice as a single intravenous, 5.925 mg/kg doses as a 5 mL/kg bolus of a 1.19 mg/mL solution. Formulated solutions were prepared from 100 μL of a 23.7 mg/mL DMSO stock, which was diluted with 1.9 mL of phosphate buffered saline immediately prior to dosing, resulting in a vehicle consisting of 5% DMSO in PBS at pH 7.4. Blood samples were taken from two animals per time-point, via cardiac puncture under terminal anaesthesia, at 0.08, 0.5, 1, 2 and 4 hours post-dose, and transferred to EDTA tubes for plasma generation. Plasma samples were immediately frozen at −20 C. For analysis, samples were thawed rapidly and 50 μL aliquots were treated with 3 volumes of extraction solvent (2:9:9 mixture of 10 mM ammonium bicarbonate, pH 8, acetonitrile and methanol, containing an analytical internal standard). Precipitated proteins were removed by centrifugation and the supernatant was analysed by LC-MS/MS. Quantification of the samples was by reference to a calibration line prepared in control mouse plasma. Pharmacokinetic parameters were determined by non-compartmental analysis using the software package PK Solutions 2.0 from Summit Research Services.

Definition of Terms

Cmax: Maximum measured concentration;
Tmax: Time at which maximum concentration was measured;
AUC 0-t: Area under the plasma drug concentration/time curve from 0 minutes to last quantifiable data point; and
AUC 0-∞: Area under the plasma drug concentration/time curve from 0 minutes extrapolated beyond the final data point based on the terminal half-life.

Identification of Bicyclic Peptide Metabolites in Mouse Plasma

Three plasma samples were available to be used (0.5, 1 and 2 hrs) for analysis of potential mouse in vivo metabolites of 17-69-07-N004. Analysis was performed by HPLC-MS and HPLC-MS/MS with a LTQ Orbitrap XL Mass Spectrometer. The approach to look for peptidic metabolites in the blood circulation was to calculate the exact mass (10 ppm window) of assumed metabolites (addition of 1 or 2 water (+18, +36) for cleavage of loop 1 and/or loop 2, respectively; thereafter loss of single amino acids or loss of amino acid stretches from loop 1 and/or loop 2). Secondly a manual search was performed by comparing the total ion chromatograms with blank mouse plasma.

Efficacy of BT17BDC-1 and BT17BDC-9 in HT-1080 Xenograft Mice

Balb/c nude mice bearing subcutaneous HT-1080 xenograft tumours were treated with BDCs or vehicle (PBS). BDCs were dosed 3 times weekly for 2 weeks, dosing initiated when tumours measured approx. 150-200 $mm^3$. Mice were monitored, and measurements of tumour volume and body weight recorded 3 times a week.

Example 1

Identification of Bicyclic Peptides With High Affinity Using MT1-MMP Hemopexin Domain Employing previously established methods for generating bicyclic peptide phage libraries, selections were performed against the human hemopexin domain of MT1-MMP. Following three rounds of selections from a naïve library employing successively reduced concentrations of target, sequencing was performed on the outputs. Bicyclic peptide 17-69 (CKNRGFGCEDFYDIC) (SEQ ID NO: 16) was identified as one the most abundant sequence outputs, and qualitative binding to the target was verified by Alphascreen.

Three small phage libraries were generated providing full sequence coverage of each of 3 portions of the 17-69 sequence. These three libraries were subjected to two rounds of selections against hemopexin protein. Interestingly, the most promising sequencing outputs were 5×6 bicyclic peptides, while the starting libraries were of the 6×6 format. It is likely that the shorter loop length was selected due to a higher affinity of the bicyclic peptide to the target protein. Shorter loop lengths result from incorrectly synthesised primers that are incorporated during the construction of the phage libraries.

The main sequencing output was the peptide 17-69-07, which has the sequence

```
                                         (SEQ ID NO: 2)
CYNEFGCEDFYDIC.
```

Based on the observation that a 5×6 format appeared most fruitful, and that distinction between the 5×6 binders was required, two more libraries were generated testing deliberate truncations of the first loop which generated bicyclic peptides 17-69-02, 17-69-03, 17-69-04 and 17-69-12. These are contained within sequences disclosed in FIG. 8.

A trend for certain residues was visible, although the binding assay was not able to distinguish between the best binders as they had reached the assay ceiling.

The most frequently occurring sequences were assayed for Hemopexin binding using the alpha screen, where all signals were high compared to the original 17-69 sequence (see Table 1 and FIG. 14):

TABLE 1

Hemopexin binding assay using the bicyclic peptides of the invention

| Name | Format | Sequence |
|---|---|---|
| 17-69 | 6x6 | CKNRGFGCEDFYDIC (SEQ ID NO: 16) |
| 17-69-02 | 5x6 | CFGEFGCEDFYDIC (SEQ ID NO: 11) |
| 17-69-03 | 5x6 | CVNEFGCEDFYDIC (SEQ ID NO: 12) |
| 17-69-04 | 5x6 | CFNEFGCEDFYDIC (SEQ ID NO: 13) |
| 17-69-07 | 5x6 | CYNEFGCEDFYDIC (SEQ ID NO: 2) |
| 17-69-12 | 5x6 | CMNQFGCEDFYDIC (SEQ ID NO: 10) |

Figure 14:
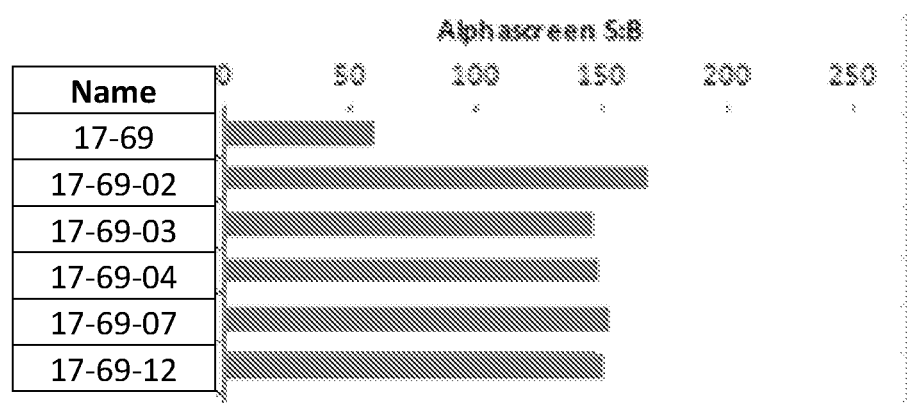
FIG. 14: An illustration of signals in an assay for Hemopexin binding using the alpha screen.

As all of the 17-69-based affinity-mature clones produced signals that were near the assay ceiling, the plot shown in FIG. 14 does not allow unequivocal identification of the best clones.

Some of the peptides were therefore synthesised as the fluoresceinated derivatives (17-69, 17-69-07 and 17-69-12), and used for direct binding fluorescent polarisation (FP) experiments. Here, the fluorescein is separated by a linker (usually Sar6) from the bicyclic sequence, either N or C-terminal to the core sequence (Table 2).

TABLE 2

Results of Direct Binding Fluorescent Polarisation (FP) Experiments

| Peptide Code | Molecular Format | FP Method | Tracer | Kd (nM) |
|---|---|---|---|---|
| 17-69-N004 | A-(17-69)-A-Sar6-K(Fl) | Direct Binding | A-(17-69)-A-Sar6-K(Fluorescein) | 692 |
| 17-69-02-N001 | A-(17-69-02)-A | Competition | A-(17-69-07)-A-Sar6-K(Fluorescein) | 191 |
| 17-69-03-N001 | A-(17-69-03)-A | Competition | A-(17-69-07)-A-Sar6-K(Fluorescein) | 16.7 |
| 17-69-12-N005 | A-(17-69-12)-A-Sar6-K(Fl) | Direct Binding | A-(17-69-07)-A-Sar6-K(Fluorescein) | 3.1 |
| 17-69-07-N040 | A-(17-69-07)-A-Sar6-K(Fl) | Direct Binding | A-(17-69-07)-A-Sar6-K(Fluorescein) | 0.52 |

The fluoresceinated derivatives of 17-69-07 and 17-69-12 (denoted as 17-69-07-N040 and 17-69-12-N005) showed strong binding with 0.52 and 3.1 nM dissociation rates, respectively. They are markedly improved over the original non-matured 17-69 sequence (17-69-N004). It appears that sequences that contain the 5×6 format induce high affinities within the context of the affinity maturation library.

Due to their high affinities to the MT1-MMP Hemopexin domain (PEX), the fluoresceinated derivatives of 17-69-07 and 17-69-12 (denoted as 17-69-07-N040 and 17-69-12-N005, respectively) were used for subsequent competition experiments (using FP for detection). Here, a pre-formed complex of PEX with the fluorescent PEX-binding tracer is titrated with free, non-fluoresceinated bicyclic peptide. Since all 17-69-based peptides (containing the conserved second loop motif CEDFYDIC; SEQ ID NO: 17) are expected to bind at the same site, the titrant will displace the fluorescent tracer from PEX. Dissociation of the complex can be measured quantitatively, and the Kd of the competitor (titrant) determined. The advantage of the competition method is that the affinities of non-fluoresceinated bicyclic peptides can be determined accurately and rapidly.

In this context, it was important to verify that the 17-69-07 and 17-69-12 core sequences are solely responsible for the high affinity to PEX. Peptides were thus synthesised as variants with N and C-terminal Alanines, thereby closely mimicking the sequence expressed on the phage particle, but lacking the Sar5/6 molecular spacer that was used with the fluoresceinated constructs.

Affinities as determined by competition experiments were almost identical to those obtained with the fluoresceinated derivatives, demonstrating unequivocally that the core bicyclic sequences are responsible for the high affinity binding to PEX (Table 3). Furthermore, the fluoresceinated constructs show that C-terminal linkages of molecular spacers and effector groups (here, as —A-Sar6-K(Fluorescein) are tolerated.

TABLE 3

Results of Direct Binding Fluorescent Polarisation (FP) Experiments

| Peptide Code | Molecular Format | Sequence | FP Method | Tracer | Kd (nM) |
|---|---|---|---|---|---|
| 17-69-07-N001 | A-(17-69-07)-A | ACYNEFGCEDFYDICA (SEQ ID NO: 18) | Competition | A-(17-69-12)-A-Sar6-K(Fluorescein) | 1.65 ± 0.29 |
| 17-69-12-N003 | A-(17-69-12)-A | ACMNQFGCEDFYDICA (SEQ ID NO: 19) | Competition | A-(17-69-07)-A-Sar6-K(Fluorescein) | 3.7 ± 2.52 |

Example 2

Proteolytic Stabilisation of the 17-69-07 Core Sequence

Mouse Plasma Stability of 17-69-07

For therapeutic applications in man, and for pre-clinical assessment in animal species, it is pertinent that a lead bicycle peptide is sufficiently stable in the circulation following intravenous administration. Adequate stability is required such that sufficient levels of bicycle peptide can bind to its target and exert its biological function.

Preclinical models often employ species such as mouse, rat, rabbit and cynomolgus monkey. In the first instance, the bicyclic peptide 17-69-07-N219 was assessed for stability in the presence of mouse plasma using methods described hereinbefore (Method #2). The bicycle core sequence retains the original natural proteinogenic amino acids of the 17-69-07 sequence, and additionally contains an N-terminal molecular spacer that is used for conjugation of effector groups (sequence: G-Sar10-ACYNEFGCEDFYDIC; SEQ ID NO: 20). The affinity of 17-69-07-N219 to PEX was retained in spite of the presence of the molecular spacer (Kd=0.82 nM).

This compound displayed a modest stability in ex vivo mouse plasma, with a half-life of 6 hours (see FIG. 1).

Identification of ex/in vivo Proteolytic Cleavage Sites in 17-69-07

In an effort to understand the chemical nature of the degradation of 17-69-07-N219 in mouse plasma, samples were analysed using MALDI-TOF for any potential degradation products. Mass spectra indicated a possible loss of tyrosine, which implicates loop opening (hydrolysis) and removal of Tyr1 in loop 1 and/or Tyr9 in loop2.

A mouse pharmacokinetic (PK) study using the minimal bicyclic peptide 17-69-07-N004 (Ac-CYNEFGCEDFYDIC (SEQ ID NO: 80), which constitutes the minimal core bicyclic peptide of 17-69-07), was conducted in order to establish clearance and elimination rates from the in vivo circulation. Resulting blood samples were further analysed, and to analyse plasma samples for any potential proteolytic degradation products of 17-69-07-N004.

Figure 2:
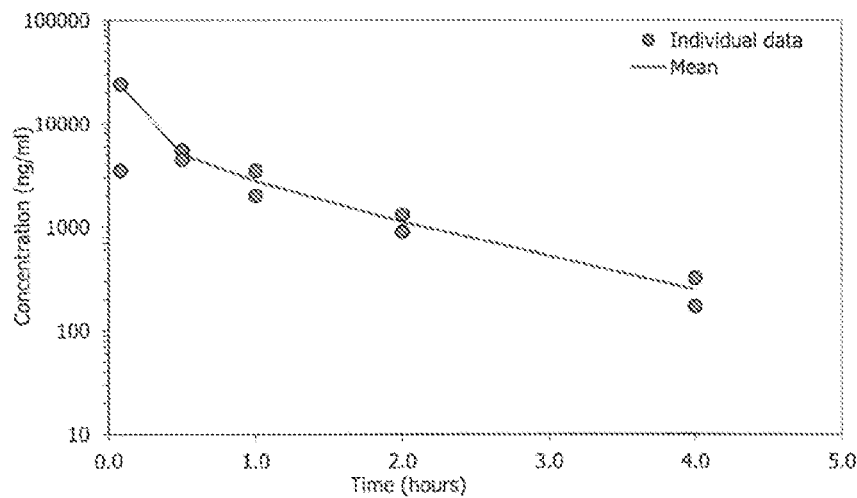
FIG. 2: PK profile of Bicyclic Peptide 17-69-07-N004 in mouse. 2 animals per time point.

The PK profile is indicated in FIG. 2.

TABLE 4

Pharmacokinetic Parameters for 17-69-07-N004

| PK Parameter | Mean |
|---|---|
| Cmax (ng/ml) | 15789 |
| Tmax (min) | 5.0 |

TABLE 4-continued

Pharmacokinetic Parameters for 17-69-07-N004

| PK Parameter | Mean |
|---|---|
| Distribution Half-life (min) | NC |
| Elimination Half-life (min) | 14 |
| AUC 0-t (µg/ml · min) | 286 |
| AUC 0-∞ (µg/ml · min) | 286 |
| Volume of Distribution based on AUC 0-∞ (L/kg) | 0.4 |
| Clearance based on AUC 0-∞ (ml/min/kg) | 20.7 |
| Time-points for Elim. Half-life regression (min) | 5-60 |

NC: not calculated due to limited data

Table 4 shows that the peptide has an elimination half-life of 14 min, and is cleared at 20.7 mL/min/kg. The clearance rate is greater than the glomerular filtration rate observed in mice (summarised in Qi et al, American Journal of Physiology—Renal Physiology (2004) Vol. 286 no. 3, F590-F596), indicating that the peptide is cleared by additional means, for example proteolysis driven by plasma and endothelial proteases.

To address whether in vivo proteolysis contributes significantly to clearance, plasma samples taken at t=0.5, 1 and 2 hrs were subjected to targeted analysis for bicycle fragments using LC-MS/MS techniques.

Multiple proteolytic metabolites could be identified, and fragments with the most intense signals are listed below in descending order:

(SEQ ID NO: 80)
Ac-CiYNEFGCiiEDFYDICiii:

excision of YNE in loop 1;
excision of YNEF in loop 1 (SEQ ID NO: 21);
excision of YNEFG (SEQ ID NO: 22) in loop 1 (the entire loop is removed);
excision of Y in loop 1 and/or 2;
excision of YD in loop 2;
excision of FYD in loop 2;
excision of YDI in loop 2; and
excision of EDFYDI (SEQ ID NO: 23) in loop 2 (the entire loop is removed).

The top three metabolites were present at medium signal level, while the remaining fragments were only detectable at trace quantities.

Taken together, both ex and in vivo metabolites appear to centre on initial cleavage at or near Tyr 1/9, followed by successive removal of residues in the vicinity. This ultimately leads to removal of either or both loops in their entirety.

Proteolytic Stability and Potency Enhancement of the 17-69-07 Sequence

Approaches to stabilising peptide sequences from proteolytic degradation are numerous (for reviews see Gentilucci et al, Curr. Pharmaceutical Design, (2010), 16, 3185-203, and Nestor et al, Curr. Medicinal Chem (2009), 16, 4399-418), and WO 2009/098450, WO 2013/050615 and WO 2013/050616). Briefly, they comprise substitution of the amino acid that provides a recognition point to the protease(s), alteration of amino acid backbone at the cleavage site (i.e. N-methylation, pseudo peptide bonds etc), steric obstruction of bonds nearby (i.e. β-substituted amino acids), and inclusion of D-enantiomeric amino acids. Some of these modifications (i.e. N-methylation, D-amino acids) may protect/shield a proteolytic cleavage site from hydrolysis even if they are located up to two residues away from the cleavage site. While it is relatively straight-forward to protect a sequence from proteolytic attack, it is much more challenging to incorporate stabilising changes that do not dramatically alter the potency (and specificity) to the target protein.

From the ex/in vivo proteolytic degradation data of 17-69-07 shown in the previous section, it is clear that Tyr1/9 and residues in the vicinity are potential sites for stabilisation of the bicyclic peptide. A quantitative means to assess successful stabilisation of the peptide is through an increase of its half-life in mouse and human plasma.

In the first instance, eleven derivatives of 17-69-07 were generated where each position was replaced by an alanine (termed "alanine scan"). This type of information advises on the energetic contribution and role of certain residues, and potentially removes proteolytic recognition points.

TABLE 5

Alanine Scan Results

| Peptide code | Molecular Description | Kd (nM) |
|---|---|---|
| 17-69-07-N004 | Ac-(17-69-07) (wildtype) $C_iYNEFGC_{ii}EDFYDIC_{iii}$ (SEQ ID NO: 2) | 2.47 ± 0.25 |
| 17-69-07-N014 | Ac-(17-69-07) Ala1 | 3.8 |
| 17-69-07-N015 | Ac-(17-69-07) Ala2 | >5000 |
| 17-69-07-N016 | Ac-(17-69-07) Ala3 | 5.1 |
| 17-69-07-N017 | Ac-(17-69-07) Ala4 | 34 |
| 17-69-07-N018 | Ac-(17-69-07) Ala5 | >5000 |
| 17-69-07-N019 | Ac-(17-69-07) Ala6 | >5000 |
| 17-69-07-N020 | Ac-(17-69-07) Ala7 | >5000 |
| 17-69-07-N021 | Ac-(17-69-07) Ala8 | >5000 |
| 17-69-07-N022 | Ac-(17-69-07) Ala9 | >5000 |
| 17-69-07-N023 | Ac-(17-69-07) Ala10 | 11.1 |
| 17-69-07-N024 | Ac-(17-69-07) Ala11 | 8 |

17-69-07-N004 is the wild-type, unmodified peptide containing a capped N-terminus (N-terminally acetylation, termed "Ac"). Some of the Ala substitutions are well-tolerated, especially at positions 1, 3, 4, 10 and 11 within the sequence. As the side chains of these residues are not required for high affinity binding to the target, compounds of formula (I) at these particular sequence positions are defined broadly.

This makes substitution at residue 1 (Tyr 1) a very attractive possibility, as it may remove one of the proteolytic recognition points. The substitution of Gly5 with Ala5 is of interest as the chemical change is minor (addition of methyl group), yet produces a dramatic reduction in potency. It is possible that Gly5 adopts unusual phi/psi angles outside the general Ramachandron chart, and these angles could be potentially induced by D-amino acids. The additional benefit would be stabilisation of the peptide bonds adjacent to this site.

For this reason, a partial D-alanine scan was performed to assess whether they are tolerated with respect to maintenance of potency: Inclusion of D-amino acids in the sequence is highly desirable due to their proteolytically stabilising effect.

TABLE 6

Effect of substituting residues in the first loop with D-Alanines

| Peptide code | Molecular Description | Kd (nM) |
|---|---|---|
| 17-69-07-N004 | Ac-(17-69-07) (wildtype) | 2.47 ± 0.25 |
| 17-69-07-N061 | Ac-(17-69-07) D-Ala1 | 23.6 |
| 17-69-07-N062 | Ac-(17-69-07) D-Ala2 | >5000 |
| 17-69-07-N063 | Ac-(17-69-07) D-Ala3 | 105 n = 1 |
| 17-69-07-N056 | Ac-(17-69-07) D-Ala4 | >5000 |
| 17-69-07-N058 | Ac-(17-69-07) D-Ala5 | 2.37 ± 0.86 |
| 17-69-07-N059 | Ac-(17-69-07) D-Pro5 | >5000 |

D-Ala1 in place of Tyr1 binds at an affinity 10-fold less than wildtype. Nonetheless it is of interest as the proteolytic recognition point Tyr1 is removed and replaced by a stabilising amino acid, without inducing a major loss in potency.

Remarkably, substitution of Gly5 with D-Ala5 is well-tolerated, as the affinity compared to wildtype remains unchanged.

In this context, D-Arg5 is also tolerated (and likely therefore all D-amino acids except D-Pro, see Table 6), which could be of interest if the physico-chemical properties need altering during further development of the molecule (Table 7).

TABLE 7

Effect of substituting residues at position 5

| Peptide code | Molecular Description | Kd (nM) |
|---|---|---|
| 17-69-07-N004 | Ac-(17-69-07) (wildtype) | 2.47 ± 0.25 |
| 17-69-07-N018 | Ac-(17-69-07) Ala5 | >5000 |
| 17-69-07-N058 | Ac-(17-69-07) D-Ala5 | 2.37 ± 0.86 |
| 17-69-07-N120 | Ac-(17-69-07) D-Arg5 | 4.24 ± 1.48 |

Next, due to the phage selection outputs indicating a certain preference for hydrophobic and aromatic amino acids at position 4 of the sequence, a series of derivatives were synthesised incorporating select aromatic amino acids, including the natural tyrosine and tryptophan (Table 8).

TABLE 8

Effect of substituting residues at position 4

| Peptide code | Molecular Description | Kd (nM) |
|---|---|---|
| 17-69-07-N004 | Ac-(17-69-07) (wildtype) | 2.47 ± 0.25 |
| 17-69-07-N057 | Ac-(17-69-07) Tyr4 | 1.78 ± 0.45 |
| 17-69-44-N002 | Ac-(17-69-07) Trp4 | 0.75 ± 0.23 |
| 17-69-07-N067 | Ac-(17-69-07) 1Al4 | 0.36 ± 0.12 |
| 17-69-07-N068 | Ac-(17-69-07) 2Al4 | 0.7 ± 0.19 |

TABLE 8-continued

Effect of substituting residues at position 4

| Peptide code | Molecular Description | Kd (nM) |
|---|---|---|
| 17-69-07-N065 | Ac-(17-69-07) Chg4 | >5000 |
| 17-69-07-N071 | Ac-(17-69-07) Phg4 | 628 |
| 17-69-07-N072 | Ac-(17-69-07) tBuGly4 | >5000 |
| 17-69-07-N137 | Ac-(17-69-07) 3,4-DCPhe4 | 1.85 ± 2.45 |
| 17-69-07-N139 | Ac-(17-69-07) Cha4 | 362 |
| 17-69-07-N140 | Ac-(17-69-07) HPhe4 | 43.3 |

1Nal: 1-naphthylalanine; 2NAI: 2-naphthylalanine; Chg: cyclohexylglycine, Phg: phenylglycine; tBuGly: tert-butylglycine; 3,4-DCPhe4: 3,4-dichlorophenylalanine; Cha: cyclohexylalanine; and HPhe: homophenylalanine.

Several substitutions at position 4 enhance the affinity compared to wildtype, these include Tyrosine, Tryphophan, 1 and 2-naphthylalanine (1/2 Nal) and 3,4 dichlorophenylalanine (3,4-DCPhe). The most potent substitution is 1-naphtylalanine, which enhances the affinity 7-fold.

Certain residues in loop 2 of 17-69-07 were examined for the purpose of enhancing stability of the molecule. These include residue 9, which contains the potential Tyr9 recognition point. Residue 11 is also attractive as it is permissive to substitution (Table 5) and vicinal to the Tyr9 recognition point.

TABLE 9

Summary of the tolerated amino acid substitutions

| Peptide code | Molecular Description | Kd (nM) |
|---|---|---|
| 17-69-07-N004 | Ac-(17-69-07) (wildtype) | 2.47 ± 0.25 |
| 17-69-07-N130 | Ac-(17-69-07) 4BrPhe9 | 2.45 ± 1.08 |
| 17-69-07-N182 | Ac-(17-69-07) 5FPhe9 | 13.1 |
| 17-69-07-N100 | Ac-(17-69-07) tBuGly11 | 1.56 ± 1.14 |

Of interest is 4-bromophenylalanine (4BrPhe), which alters the Tyr9 proteolytic recognition point, and tert-butylglycine (tBuGly), which slightly enhances the affinity and importantly, strongly protects the vicinal amino acid backbone from proteolytic hydrolysis by steric obstruction.

Multi-Site Substitutions to Achieve Global Proteolytic Protection of 17-69-07

The previous section disclosed multiple positions within the 17-69-07 sequence that permit inclusion of proteolytically stabilising and/or affinity enhancing amino acids.

In an effort to combine these modifications in a single molecule, a molecule was synthesised that incorporated a Tyr1→D-Ala1, Phe4→1Naphthylalanine4, Gly5→D-Ala5, Tyr9→BrPhe9 and Ile11→tBuGly11 substitution. Remarkably, all modifications are tolerated in concert, and the potency is superior to that of the wild-type molecule (Tables 10 and 11).

TABLE 10

Results from a specific multi-substitution

| Peptide code | Molecular Description | Kd (nM) |
|---|---|---|
| 17-69-07-N004 | Ac-(17-69-07) (wildtype) | 2.47 ± 0.25 |
| 17-69-07-N252 | Ac-(17-69-07) D-Ala1 1Nal4 D-Ala5 4BrPhe9 tBuGly11 | 0.8 ± 0.39 |

In anticipation of attaching effector groups to such a bicyclic peptide during the further development of the molecule, versions were generated with an N-terminal sarcosine molecular spacer (10 consecutive Sar, denoted as Sar10) initiated with an N-terminal glycine and terminated with a C-terminal alanine. For the purpose of this experiment, the N-terminal Gly was capped with an acetyl group so as to remove the positive charge.

TABLE 11

Comparative data following G-Sar10-A addition

| Peptide code | Molecular Description | Kd (nM) |
|---|---|---|
| 17-69-07-N004 | Ac-(17-69-07) (wildtype) | 2.47 ± 0.25 |
| 17-69-07-N225 | Ac-G-Sar10-A-(17-69-07) | 0.95 ± 0.1 |
| 17-69-07-N239 | Ac-G-Sar10-A-(17-69-07) D-Ala1 1Nal4 D-Ala5 tBuGly11 | 0.94 ± 0.08 |
| 17-69-07-N255 | Ac-G-Sar10-A-(17-69-07) D-Ala1 1Nal4 D-Ala5 4BrPhe9 tBuGly11 | 0.3 |

The data indicate that both molecular spacer (attached to the N-terminus as indicated) and the amino acid substitutions within the bicycle core sequence are well-tolerated, as potencies are retained or improved.

Table 12 shows the non-acetylated (non-)stabilised derivatives of the molecules shown in Table 11. Their stabilities were assessed quantitatively in mouse and human plasma in order to demonstrate an improvement compared to the non-stabilised 17-69-07-N219 (FIG. 1).

TABLE 12

Molecules selected for plasma stability assessment, associated potencies

| Peptide code | Molecular Description | Kd (nM) |
|---|---|---|
| 17-69-07-N219 | G-Sar10-A-(17-69-07 ) (non-stabilised with spacer) | 0.82 ± 0.09 |
| 17-69-07-N244 | G-Sar10-A-(17-69-07) D-Ala1 1Nal4 D-Ala5 4BrPhe9 tBuGly11 | 0.45 ± 0.19 |
| 17-69-07-N231 | G-Sar10-A-(17-69-07) D-Ala1 1Nal4 D-Ala5 tBuGly11 | 1.07 ± 0.28 |
| 17-69-07-N241 | bAla-Sar10-A-(17-69-07) D-Ala1 1Nal4 D-Ala5 tBuGly11 | 1.21 ± 0.24 |

Figure 3:
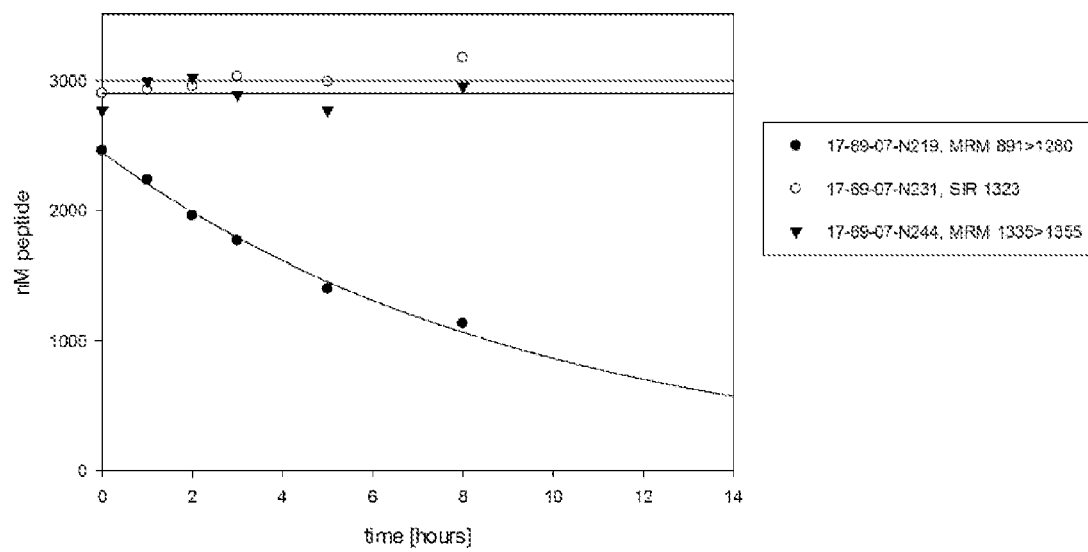
FIG. 3: (A) Mouse and (B) Human Plasma Stability of two stabilised 17-69-07 molecules (with 4-bromophenylalanine at position 9: 17-69-07-N244, without 4-bromophenylalanine at position 9: 17-69-07-N231) compared to the non-stabilised 17-69-07-N219. Several MRM transitions for a given analyte were monitored which correlated well between each other. For the purpose of this graph, only one transition is displayed.
Figure 3:
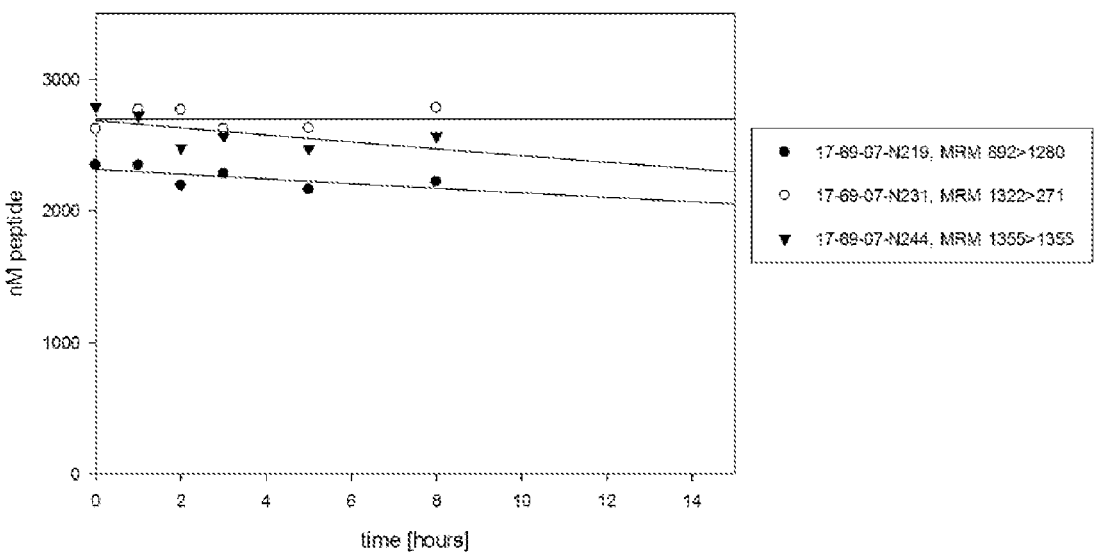

FIG. 3A shows the mouse plasma stability of the penta and tetra-substituted molecules 17-69-07-N244 and 17-69-07-N231, respectively, in comparison to the original non-stabilised wildtype molecule 17-69-07-N219. The half-life of the peptide in mouse plasma at 37° C. is >>20 hours, compared to 6 hours for the non-enhanced wildtype molecule.

FIG. 3B shows the human plasma stability of the penta and tetra-substituted molecules 17-69-07-N244 and 17-69-07-N231, respectively, in comparison to the original non-stabilised wildtype molecule 17-69-07-N219. The half-life of the peptide in mouse plasma at 37° C. is >>20 hours, compared to 6 hours for the non-enhanced wildtype molecule.

In summary, targeted substitutions at up to 5 positions in the 17-69-07 bicyclic core sequence (Tyr1→D-Ala1, Phe4→1Naphthylalanine4, Gly5→D-Ala5, Tyr9→4BrPhe9 and Ile11→tBuGly11) generated superior molecules with enhanced potency and significant improvement in plasma stability.

Selectivity of a Stabilised 17-69-07 Derivative (17-69-07-N241)

The stabilised, molecular spacer containing derivative 17-69-07-N241 was tested by FP competition for affinity to MT1-MMP hemopexin domain derived from other species. The data is summarised in Table 13:

TABLE 13

Species cross-reactivity of 17-69-07 and derivatives

|  | Human/cyno (Kd, nM) | Dog (Kd, nM) | Mouse (Kd, nM) |
| --- | --- | --- | --- |
| 17-69-07-N219 | 0.82 | 0.9 | nd |
| 17-69-07-N241 | 1.21 | 1.4 | 0.63 |

Both non-stabilised and stabilised derivatives of 17-69-07 are fully cross reactive.

The N-terminally fluoresceinated derivative of 17-69-07-N241 (termed 17-69-07-N258, of the sequence: Fluorescein-(bAla)-Sar10-A-(17-69-07) D-Ala1 1Nal4 D-Ala5 tBuGly11) was tested against related human metalloproteinases. The data demonstrate that the 17-69-07 core sequence, and this stabilised variant, are uniquely selective for MT1-MMP (Table 14).

TABLE 14

Selectivity of 17-69-07 and derivatives to related metalloproteinases

|  | MT1-MMP (=MMP-14) (Kd, in nM) | MMP-1 (Kd, in nM) | MMP-2 (Kd, in nM) | MMP-15 (Kd, in nM) | MMP-16 (Kd, in nM) |
| --- | --- | --- | --- | --- | --- |
| 17-69-07-N258 | 2.2 | >1000 | >1000 | >1000 | >1000 |

Example 3

In vivo Analysis of Proteolytically Stabilised Variants of 17-69-07 Conjugated to a Chelator Peptides linked to metal chelators have multiple applications in diagnostics and therapeutics. Certain imaging or therapeutic radioisotopes can be "loaded" onto the chelator while the peptide carries said isotopes to the target. In this manner, tumour specific antigens can be visualised using, for example, PET and SPECT scanners. For targeted radiotherapy, therapeutic radionuclides (such as $^{90}$Y and $^{177}$Lu) are loaded onto the chelator-peptide and selectively carried to the tumour by binding the tumour-associated antigen. There they exert their anti-tumour activity by the high energy radiation they emit.

Synthesis of Chelator-Linked 17-69-07 Bicyclic Peptides

Five derivatives were synthesised where the metal chelator DOTA (1,4,7,10-tetraazacyclododecane-1,4,7,10-tetraacetic acid) was linked to the N-terminal Alanine of the 17-69-07 bicyclic peptide.

TABLE 15

Summary of the molecules and structure

| Peptide code | Molecular Description | Kd (nM) |
| --- | --- | --- |
| 17-69-07-N144 | DOTA-A-(17-69-07) | 0.5 |
| 17-69-07-N147 | DOTA[Lu]-A-(17-69-07) | 0.95 ± 0.5 |

TABLE 15-continued

Summary of the molecules and structure

| Peptide code | Molecular Description | Kd (nM) |
| --- | --- | --- |
| 17-69-07-N248 | DOTA-A-(17-69-07) D-Ala1 1Nal4 D-Ala5 4BrPhe9 tBuGly11 | 0.5 |
| 17-69-07-N246 | DOTA-A-(17-69-07) All D Amino Acids | >5000 |

17-69-07-N144 is the wildtype sequence of 17-69-07 where DOTA is directly linked to an N-terminal Alanine that serves as a one amino acid spacer. This molecule retains full potency to MT1-MMP. To demonstrate that potency is retained when loaded with a therapeutic/imaging radionuclide, the chelator was loaded with the natural (cold) $^{175}$Lutetium as a safe substitute. Potency was retained.

The fully stabilised variant, 17-69-07-N248, also retained potency in the context of the DOTA conjugate.

A control molecule was prepared, 17-69-07-N246, which is the full D-amino acid equivalent of 17-69-07-N144. This molecule is completely resistant to proteolytic degradation as amide bonds adjacent to D amino acids are protected from proteases, and lacks any activity toward MT1-MMP. Importantly, this peptide retains the exact same sequence and chemical composition.

Biodistribution of $^{177}$Lu-Loaded 17-69-07-N144 in HT1080 Xenograft Mice

HT-1080 cells (which are known to abundantly express MT1-MMP) were subcutaneously inoculated into the right trunk of male 6-week-old BALB/c nu/nu mice. The tumours were allowed to grow for approx. 1 week.

150 pmole of 17-69-07-N144 peptide was loaded with 1 MBq of the γ- and β-emitter $^{177}$Lu using standard complexation techniques. Per tumour-bearing mouse, 150 pmole of the loaded 17-69-07-N144 was then injected (the equivalent of 17 µg/kg). 3 animals were euthanized per time point, various organs and tumour excised and weighed, and followed by determination of the gamma-radiation count per gram of tumour/organ tissue. The resulting plot gives a quantitative indication of the localisation of the peptide in the in vivo mouse. In particular, selective accumulation in the HT1080 tumour indicates MT1-MMP binding in vivo.

Figure 4:
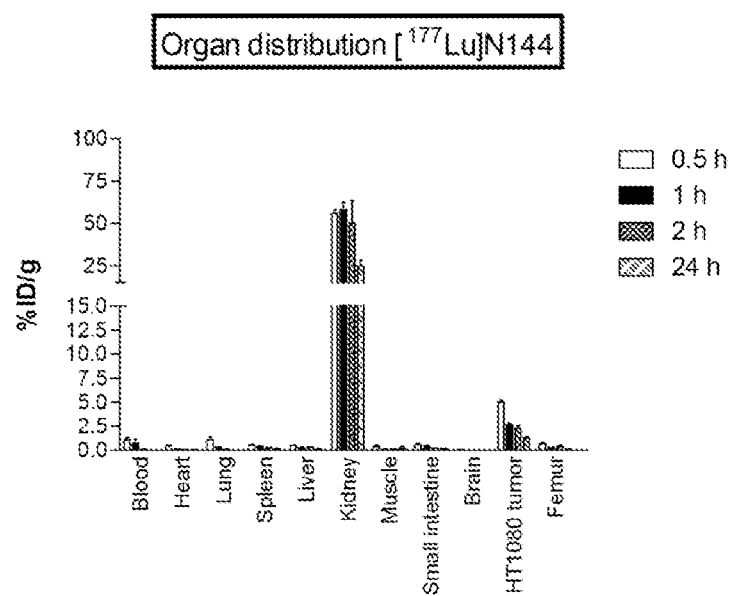
FIG. 4: Biodistribution of $^{177}$Lu 17-69-07-N144 in HT-1080 xenograft mice.

FIG. 4 summarises the biodistribution data. Remarkably, the bicyclic peptide is specific for the tumour and appears to persist up to 24 hours, despite an estimated half-life in the circulation of 14 min. This likely indicates uptake into the tumour cells. Significant localisation is visible at the kidneys, and it is likely that this is due to kidney amino acid transporters transiently binding the peptide. All other organs do not show significant uptake of the molecule. Of note, the mouse hemopexin domain shares full homology with the human counterpart, indicating that if mouse PEX were expressed elsewhere, corresponding signals would be observed.

Figure 5:
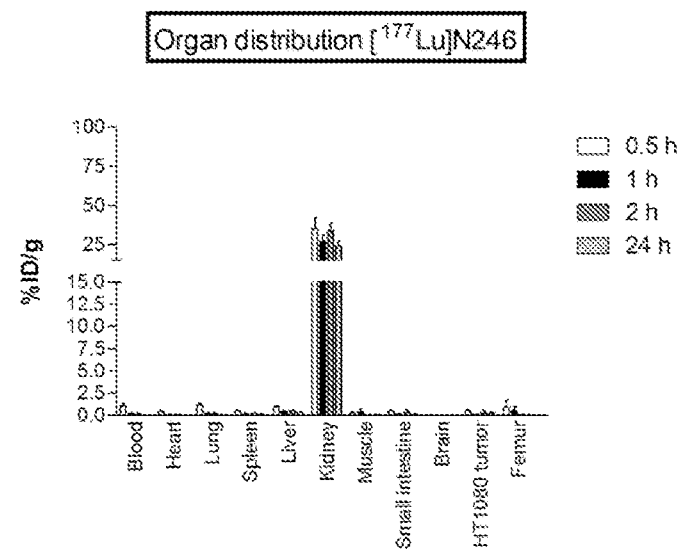
FIG. 5: Biodistribution of $^{177}$Lu 17-69-07-N246 in HT-1080 xenograft mice.

To assess whether tumour uptake in the xenograft model is selective and due to PEX binding, an additional study was performed using the peptide 17-69-07-N246, which is the D-amino acid counter-part of 17-69-07-N144 (FIG. 5).

Comparing the biodistribution pattern to the one obtained with the active bicyclic peptide 17-69-07-N144, it is clear that the MT1-MMP non-binding 17-69-07-N246 bicyclic peptide does not target the tumour, confirming that the tumour signal of 17-69-07-N144 is driven by MT1-MMP target binding in vivo.

Figure 6:
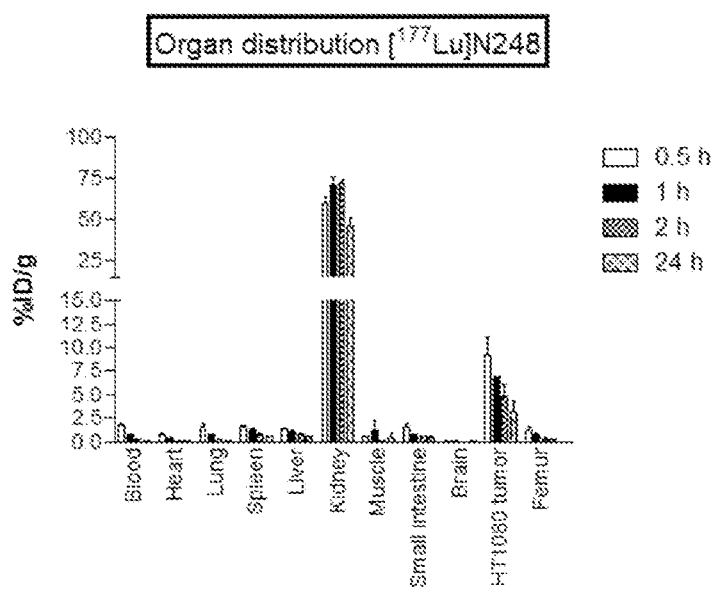
FIG. 6: Biodistribution of $^{177}$Lu 17-69-07-N248 in HT-1080 xenograft mice.

Finally, to assess the effect of proteolytic stabilisation of the 17-69-07 sequence on biodistribution, bicyclic peptide 17-69-07-N248 (DOTA-A-(17-69-07) D-Ala1 1Nal4 D-Ala5 4BrPhe9 tBuGlyl1) was employed in an identical biodistribution study (FIG. 6).

Strikingly, the enhanced proteolytic stability of the peptide leads to an overall doubling of the tumour uptake at any given time point compared to 17-69-07-N144, exemplifying the superior properties of the molecule compared to the original, non-stabilised 17-69-07 sequence.

It is anticipated that this effect could result in an advantageous therapeutic index, both for radionuclide targeted therapy using the conjugates described in this example and in the context of toxin-conjugated bicyclic peptides (Example 4).

Example 4

Conjugation of Non-Stabilised Bicyclic Peptides With Cytotoxic Agents

For targeted cancer therapy, highly potent cytotoxic drugs are attached through a cleavable linker to a targeting entity (here, a bicyclic peptide), which binds to tumour-associated cell surface-expressed proteins. The overexpressed tumour associated cell surface protein target is selected for its ability to internalise into the interior of the cell. Upon binding of the cytotoxic agent -conjugated targeting entity to the tumour-associated cell surface protein, the entire molecular complex internalises to the inside of the cell. Following the transition from the systemic circulation into the distinct intracellular environment, the cytotoxic drug is cleaved from the targeting entity by intracellular conditions, and the cleaved drug then exerts its anti-tumour activity by inducing targeted cell-death through cell-cycle arrest followed by apoptosis.

Bicyclic peptide 17-69-07-N219 (see Examples 2 and 3) is composed of the wildtype bicyclic core sequence linked on the N-terminal side to a Gly-Sar10-Ala molecular spacer (G-Sar10-A-(17-69-07), where the full sequence description is G-Sar10-A-CYNEFGCEDFYDIC; SEQ ID NO: 20). This derivative of (17-69-07) retains full potency (Table 12) to MT1-MMP at a Kd of 0.8 nM. The free, unique amino group at N-terminal side of the molecular spacer is ideally placed for conjugation with effector groups such as highly potent cytotoxic substances. The long intramolecular distance imparted by the Sar10 linker between the conjugation site on the N-terminal Gly and the bicycle core sequence is employed so as to guarantee full retention of target binding potency following conjugation with effector groups of significant molecular size. Shorter molecular spacers may be selected at will so long as the potency of the bicycle core sequence to the target protein is retained.

To generate proof of concept data with a Bicyclic peptide Drug Conjugate (termed BDC) targeting MT1-MMP, two conjugates of 17-69-07-N219 were prepared, which either employed the microtubule polymerisation-inhibiting toxins DM1 (a maytansine, also known as N2'-Deacetyl-N2'-(3-Mercapto-1-Oxopropyl)-Maytansine) or MMAE (Monomethylauristatin E, also known as (S)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide).

The MMAE conjugate is termed BT17BDC-1 and is separated from the 17-69-07-N219 precursor by a Valine-Citrulline (Val-Cit) linker including the self-immolating para-aminobenzyl-carbonyl group (PABC). The Val-Cit linker is selectively cleaved (hydrolysed) by the Cathepsin B-rich environment encountered in the intracellular lysosomes, and following hydrolysis, PABC immolates to release MMAE as the active toxic species. The Val-Cit-PABC linker is stable in the circulation, and thus releases the toxin only upon cell internalisation.

The structure of the conjugate, and the synthetic scheme for the preparation of BT17BDC-1, is shown in Scheme I:

Scheme I

Structure BT17BDC-1

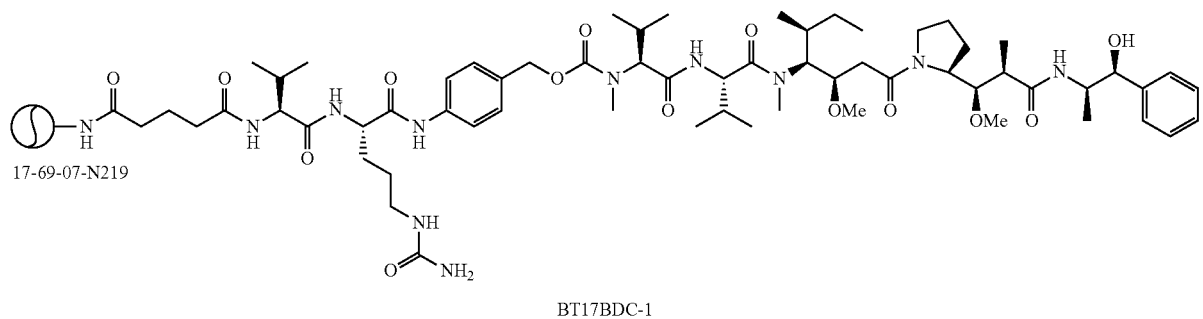

BT17BDC-1

Reaction Scheme

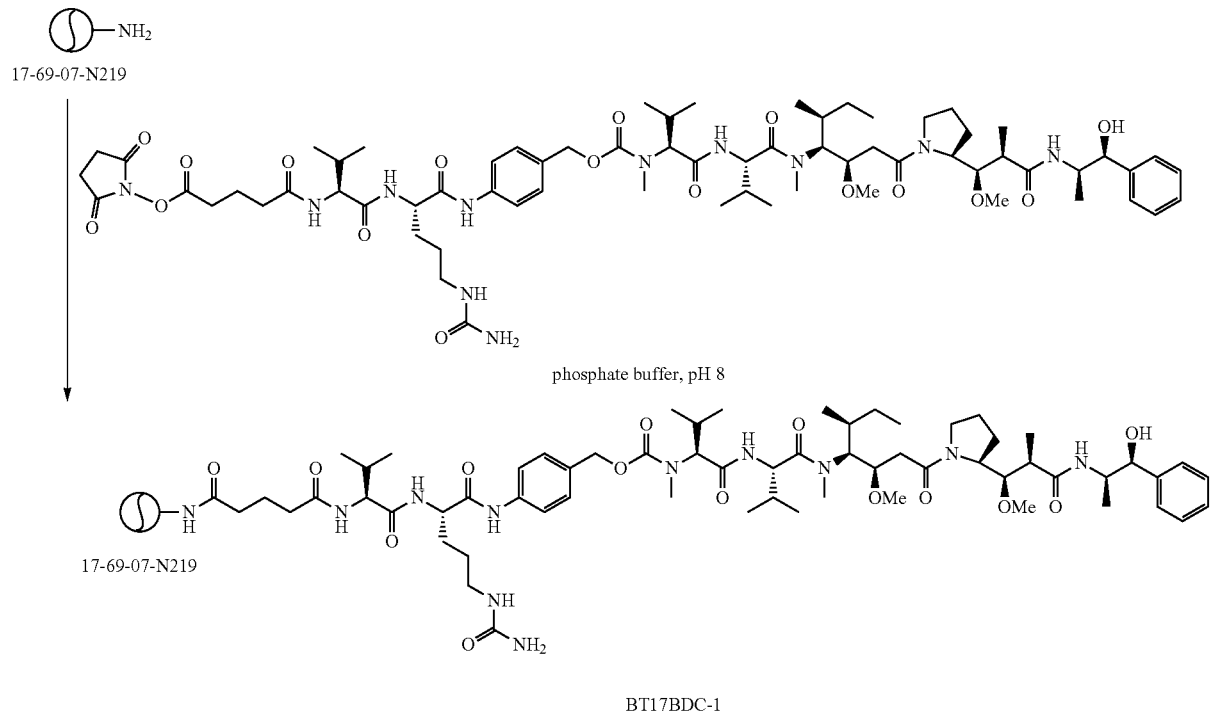

BT17BDC-1

Synthetic strategy for preparation of BDC17BDC-1: The fully purified, TMB cyclised 17-69-07-N219 bicycle precursor is reacted with the succinimide ester of glutaryl-Valine-citrulline-p-aminobenzylcarbonyl-MMAE (commonly abbreviated as vc-MMAE or Val-Cit-PABC-MMAE), yielding the conjugate BDC17BDC-1.

The DM1 conjugate of 17-69-07-N219 is termed BT17BDC-9 and is separated from the 17-69-07-N219 precursor by a disulphide bond, which can be cleaved by the reducing environment encountered in the intracellular milieu. The reduction is believed to take place through intracellular glutathione, which is present at ~10 mM concentrations inside the cell. By contrast, the concentration of glutathione and free reducing agents in the blood circulation is much lower (<10 μM); thus the toxin is released predominantly in the intracellular environment, where it can unfold its cell killing activity.

The structure of the conjugate, and the synthetic scheme for the preparation of BT17BDC-9, is shown in Scheme II:

Scheme II

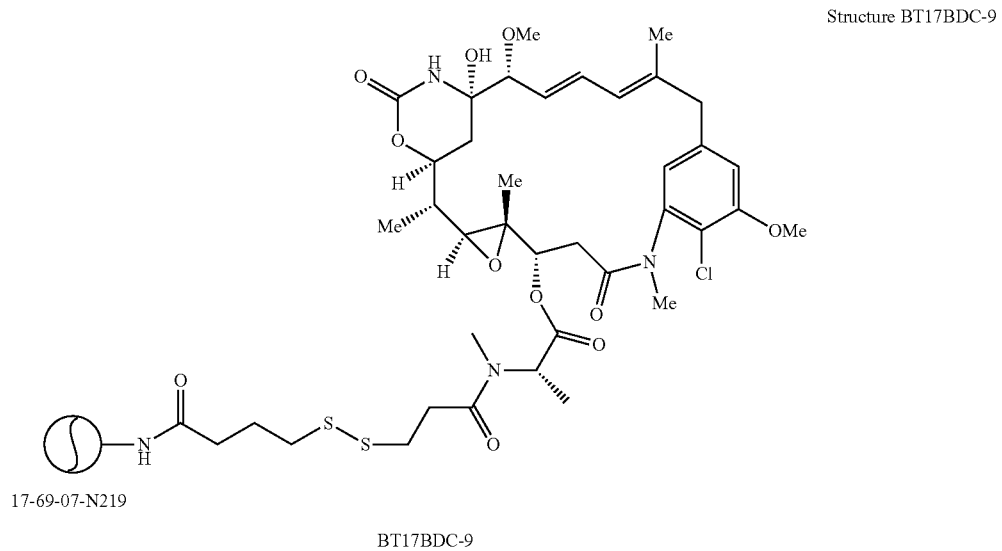

BT17BDC-9

-continued
Reaction Scheme

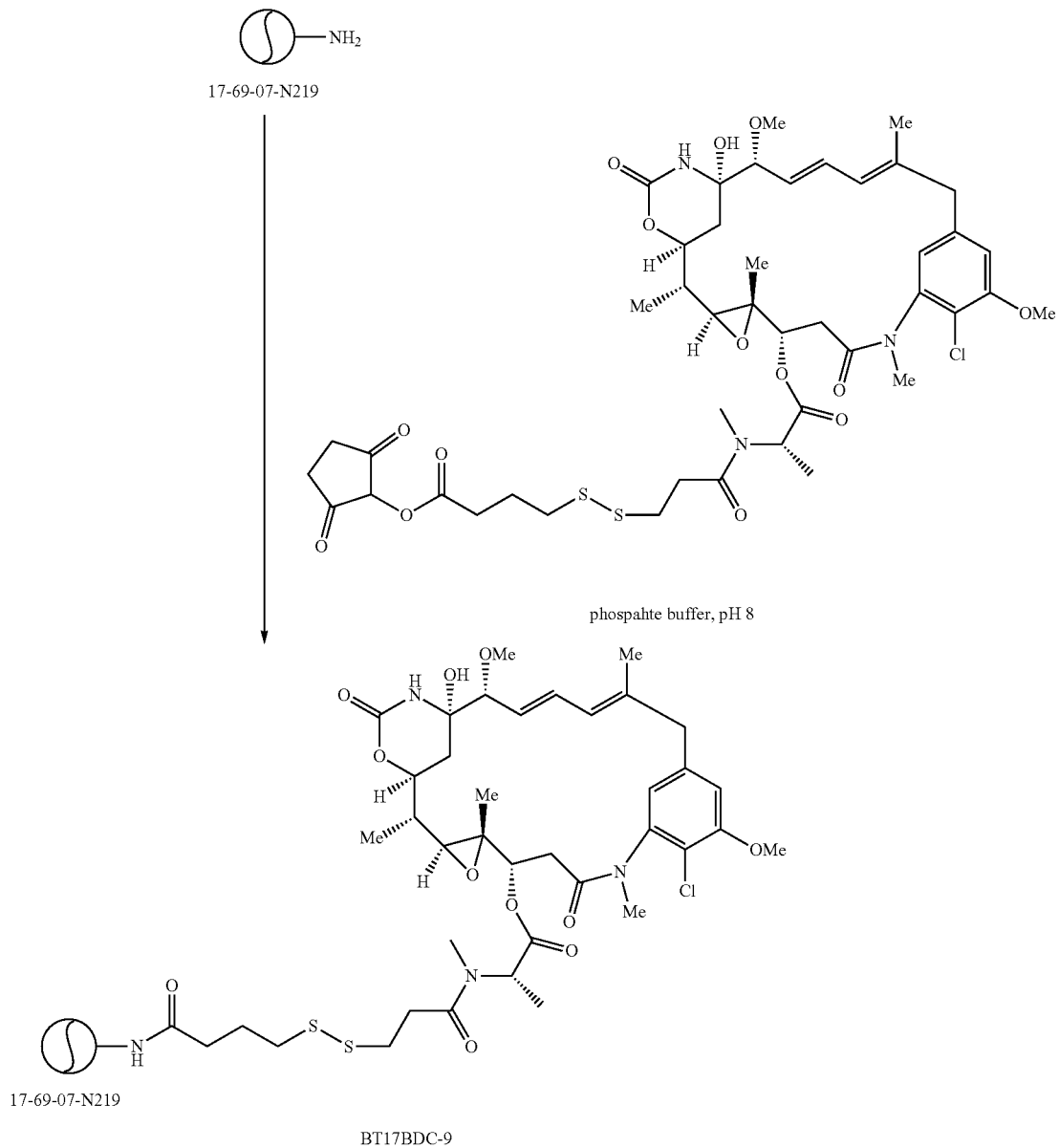

BT17BDC-9

Synthetic strategy for preparation of BDC17BDC-9: The fully purified, TMB cyclised 17-69-07-N219 bicycle precursor containing the free, N-terminal amine, is reacted with the succinimide ester of disulphide -DM1 (structure as shown), yielding the conjugate BDC17BDC-9.

The release of the toxins in BDC17BDC-1 and BDC17BDC-9 is therefore mechanistically distinct, i.e. the former through intracellular proteolytic conditions, and the latter by intracellular reducing conditions.

The two BDCs were employed in in vitro cytotoxicity studies and showed low nanomolar/picomolar potency on cell cultures such as HT1080 (data not shown).

Figure 7:
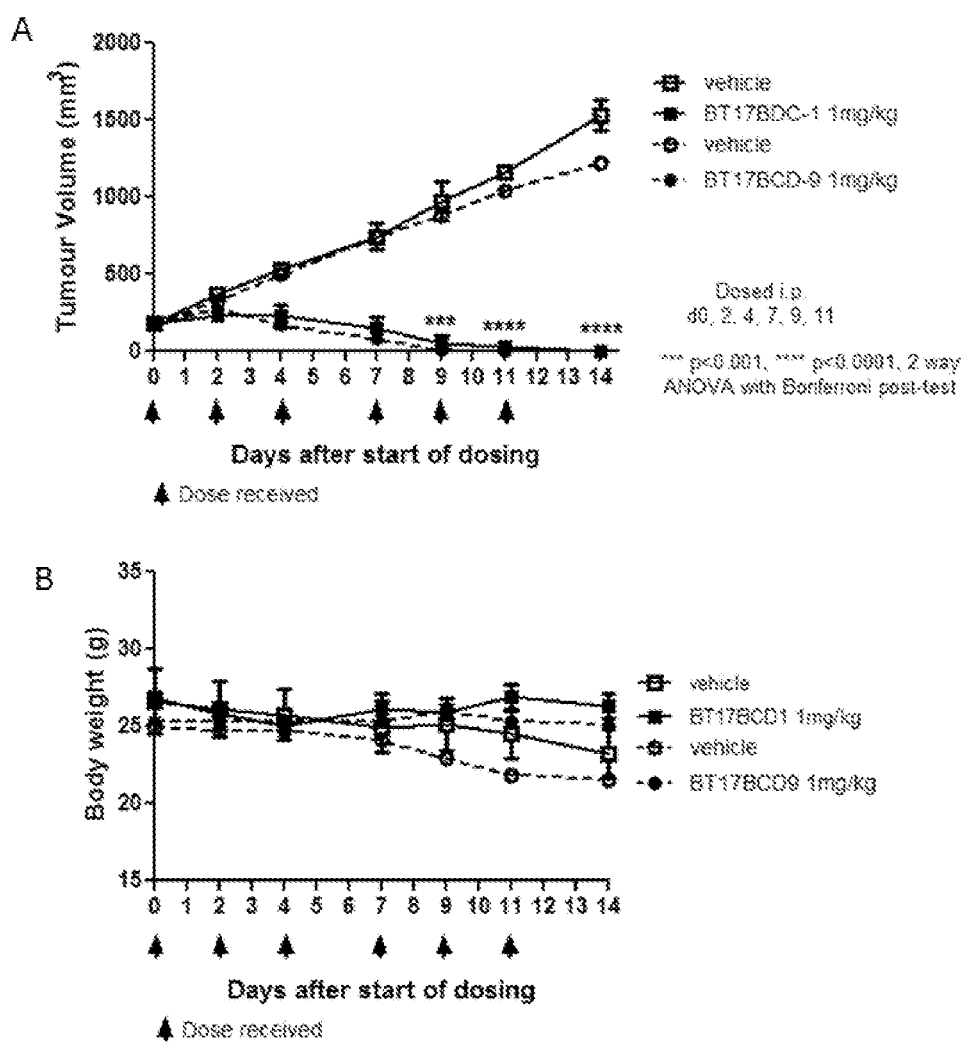
FIG. 7: (A): Plot of mean tumour volume versus time for BT17BDC-1 and 9. Doses were administered on day 0, 2, 4, 7, 9, and 11. (B): Body weight during treatment, which is indicative of drug-associated toxicology and overall animal health.

In an in vivo mouse xenograft model (harbouring HT1080 tumours), both BDCs caused significant reduction in tumour volume after 9 days post injection compared to vehicle control. The dosage regime is indicated in FIG. 7 (arrows). Tumours were completely cleared by day 14 for both BDCs, as judged by palpation (FIG. 7). Notably, the weight of the animals for both BDC17BDC-1 and BDC17BDC-9 were largely stable, indicating a therapeutic window that could be sufficient for therapeutic purposes.

Example 5

Conjugation of Proteolytically Stabilised Bicyclic Peptides With Cytotoxic Agents The bicyclic core sequence 17-69-07 containing the modifications of D-alanine at position 1,1-naphthylalanine at position 4, D-alanine at position 5, and α-tert-butylglycine at position 11 with or without 4-bromophenylalanine at position 9, had enhanced proteolytic stability in ex vivo plasma and in vivo (Examples 2, 3).

In the context of bicycle drug conjugates, it is likely that a more stable bicycle core sequence could lead to greater tumour exposure due to reduced systemic clearance and greater stability in the proteolytically aggressive tumour microenvironment. Both can result in increased MT1-MMP driven uptake of BDC to inside the cell, leading to an increase in therapeutic efficacy.

The stabilised bicyclic peptide 17-69-07-N241 was designed with an overall similar molecular layout to the non-stabilised 17-69-07-N219 (described in Examples 3 and 4). It has the following sequence:

(B-Ala)-Sar10-AC(D-Ala)NE(1Nal)(D-Ala)CEDFYD (tBuGly)C (SEQ ID NO: 5)

which is cyclised with TBMB as before.

The N-terminal beta-alanine was selected rather than the previously employed glycine as in 17-69-07-N219 so as to minimise diketopiperazine side product formation during the coupling with N-hydroxysuccinimide (NHS) esters (Purdie et al (1973), J. Chem. Soc., Perkin Trans. 2, 1845), specifically in this example with NHS esters of cytotoxic agents (Scheme I, II).

The sarcosine decamer spacer is retained as in 17-69-07-N219 so as to ensure full retention of binding of the bicycle peptide to the hemopexin domain of MT1-MMP.

The maytansine toxin class was selected for conjugation to 17-69-07-N241 based on the efficacy and tolerability in the mouse xenograft model described in Example 4, and the disulphide cleavable linker was again selected.

Four BDCs were prepared (referred to hereinbefore as BT17BDC-17, BT17BDC-18, BT17BDC-19 and BT17BDC-20), whereby both toxin and 17-69-07-N241 were invariant, while the disulphide bond susceptibility to reduction/cleavage was altered by modulating the degree of hindrance adjacent to the sulphur atoms.

The synthetic route to the conjugates is as described in Scheme II, wherein 17-69-07-N219 is replaced with 17-69-07-N241.

For BT17BDC-18, an additional route to synthesis involved generation of a pyridyl-disulphide bicycle precursor (termed 17-69-07-N277), which is reacted with DM1 to form the full conjugate. The synthetic route is described in Scheme III.

-continued

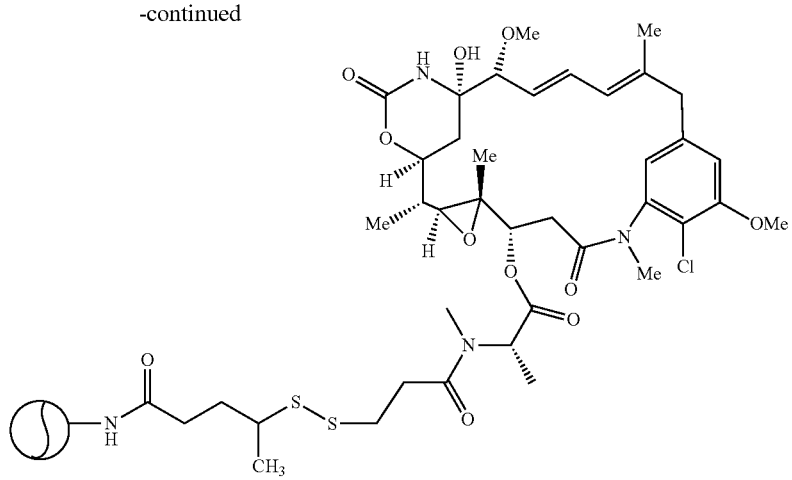

BT17BDC-18

Synthetic strategy for preparation of BDC17BDC-18: The fully purified, TMB cyclised 17-69-07-N241 bicycle precursor containing the free, N-terminal amine, is reacted with the SPP (N-succinimidyl 4-(2-pyridyldithio)pentanoate)), yielding the Intermediate 17-69-07-N277. This is then reacted with DM1 as the free thiol, yielding the desired conjugate BT17BDC-18.

In vitro Characterisation of BT17BDC-17, BT17BDC-18, BT17BDC-19 and BT17BDC-20

The four BDCs were assessed for several in vitro parameters such as retention of potency to the human MT1-MMP hemopexin domain, stability in ex vivo mouse, rat and human plasma, and stability to reducing agents such as dithiothreitol.

The data is summarised in Table 16 below:

TABLE 16

In vitro properties of BT17BDC-17, BT17BDC-18, BT17BDC-19 and BT17BDC-20

| Bicycle Drug Conjugate | Kd (nM) (Hemopexin domain)[a] | $t_{1/2}$ (hrs) (human plasma)[b] | $t_{1/2}$ (hrs) (mouse plasma)[b] | $t_{1/2}$ (hrs) (rat plasma)[b] | Relative Stability to DTT (ADC)[c] | Relative Stability to DTT (BDC)[d] |
|---|---|---|---|---|---|---|
| 17-69-07-N219 | 0.82 ± 0.09 (n = 3)[e] | 30.3 ± 4.7 (n = 1) | 3.9 ± 0.3 (n = 1) | 3.7 ± 0 (n = 1) | n/a | n/a |
| 17-69-07-N241 | 1.4 ± 0.3 (n = 10)[e] | >36 (n = 2) | >36 (n = 2) | >36 (n = 1) | n/a | n/a |
| BT17BDC-17 | 0.7 (n = 1)[e] | 4.2 ± 0 (n = 2) | 5.5 ± 0.7 (n = 1) | 1.2 ± 0.1 (n = 1) | 1 | 1 |
| BT17BDC-18 | 0.99 ± 0.17 (n = 6)[e] | 12.7 ± 2.2 (n = 2) | 14.3 ± 1 (n = 2) | 4.3 ± 0.6 (n = 2) | 7 | 5 |
| BT17BDC-19 | 0.5 (n = 1)[e] | 23.5 ± 4.1 (n = 2) | >36 (n = 1) | >36 (n = 1) | 14 | 30 |
| BT17BDC-20 | 2.95 ± 1.3 (n = 4)[f] | 32 ± 1 (n = 1) | >36 (n = 1) | 34 ± 4 (n = 1) | 170 | 93 | where n/a: not applicable, and where n = numbers of repeats
[a] determined by fluorescence polarisation competition experiments using 17-69-07-N040 as a tracer
[b] determined using quantitative LC-MS. Incubation time up to 24 hrs in plasma, containing 4 μM BDC.
[c] from Kellogg et al (2011) Bioconjugate Chemistry, 22, 717. Note these values relate to antibody drug conjugates containing the disulphide linker described in the text
[d] determined by quantitative LC-MS. Note these values relate to Bicycle Drug Conjugates containing the disulphide linker described in the text. Methods were adapted from Kellogg et al (2011) Bioconjugate Chemistry, 22, 717.
[e] Use of 17-69-07-N004 as tracer in FP competition
[f] Use of 17-69-07-N040 as tracer in FP competition All molecular constructs retain their affinity to the hemopexin target (second column).

The data indicates that plasma stability is governed by the nature of the disulphide bond (as modulated by susceptibility to reduction), and not the nature of the bicyclic peptide, since all BDCs contain the same bicyclic peptide (17-69-07-N241) which is stable in the plasma from the three species tested.

Furthermore, BT17BDC-18, BT17BDC-19 and BT17BDC-20 show stabilities in human plasma adequate for therapeutic use, since the anticipated renal filtration driven clearance of the peptides of this molecular size in man has an estimated half-life of 2 to 4 hours, which is several-fold faster than the degradation half-life of the BDCs in human plasma (>14 hrs BT17BDC-18/19/20, see Table 16). Thus, the bulk of the BDC is expected to clear renally, with only a fraction being degraded in the circulation, making these BDCs potentially suitable for therapeutic purposes.

In vivo Efficacy of BT17BDC-17, BT17BDC-18, BT17BDC-19 and BT17BDC-20

All BDCs containing the stabilised bicycle core sequence were tested for their efficacies in in vivo mouse xenograft models, using the human lung squamous cell carcinoma line EBC-1.

Figure 9:
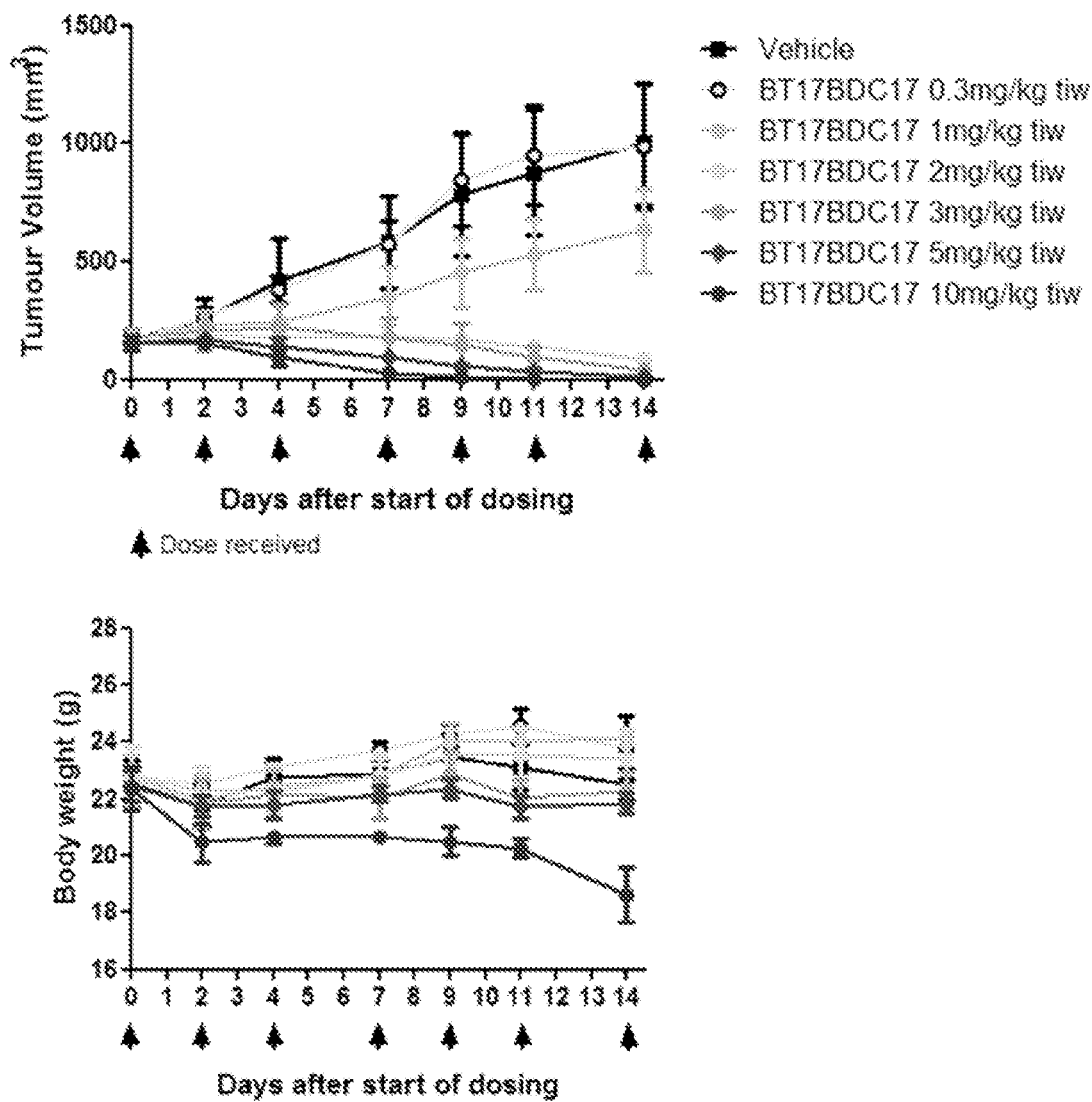
FIG. 9: Top: Plot of mean tumour volume versus time for BT17BDC-17 in EBC-1 xenograft mice. Doses were administered on day 0, 2, 4, 7, 9, 11 and 14. Bottom: Body weight during treatment, which is indicative of drug-associated toxicology and overall animal health.
Figure 10:
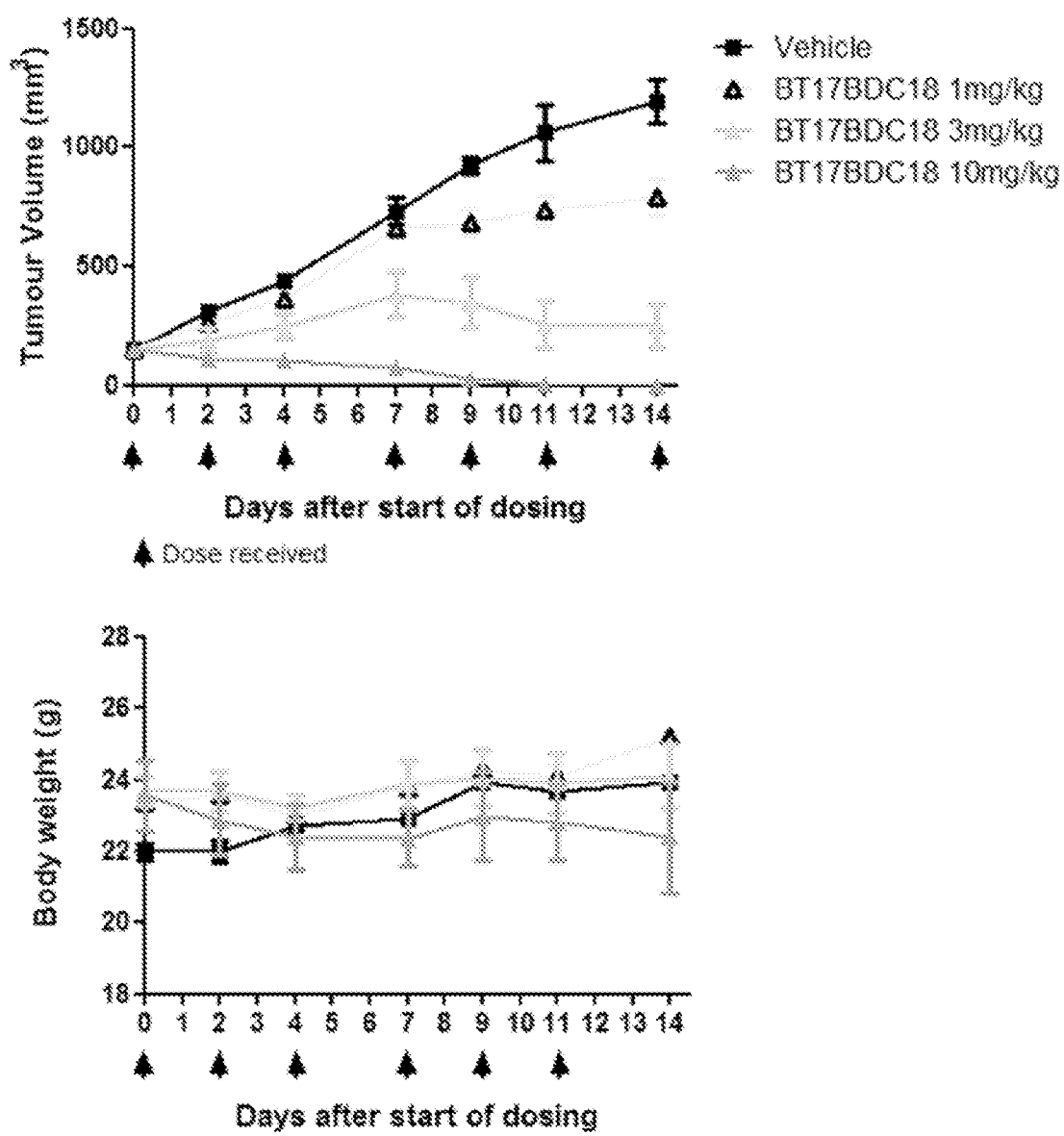
FIG. 10: Top: Plot of mean tumour volume versus time for BT17BDC-18 in EBC-1 xenograft mice. Doses were administered on day 0, 2, 4, 7, 9, 11 and 14. Bottom: Body weight during treatment, which is indicative of drug-associated toxicology and overall animal health.
Figure 11:
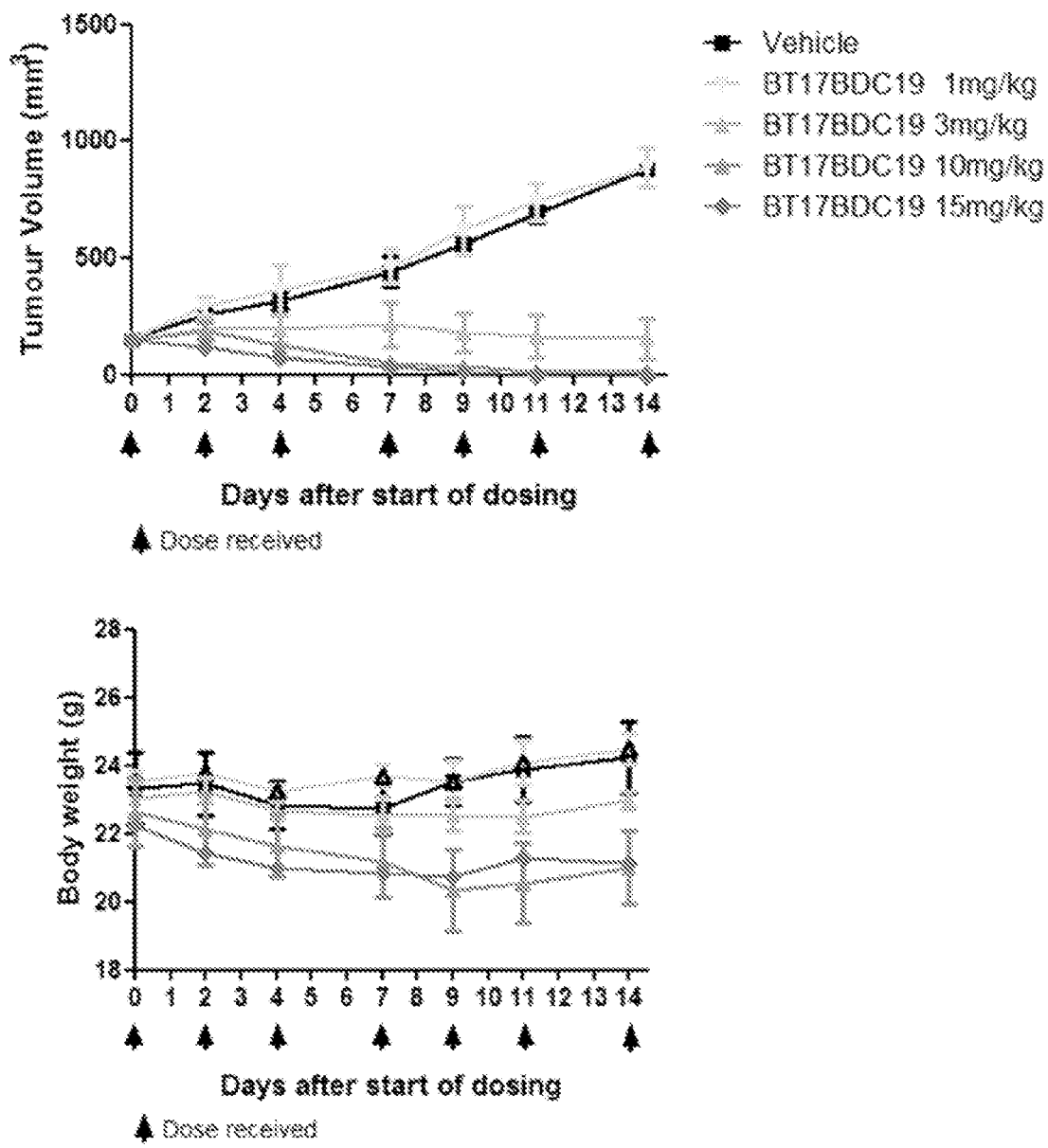
FIG. 11: Top: Plot of mean tumour volume versus time for BT17BDC-19 in EBC-1 xenograft mice. Doses were administered on day 0, 2, 4, 7, 9, 11 and 14. Bottom: Body weight during treatment, which is indicative of drug-associated toxicology and overall animal health.
Figure 12:
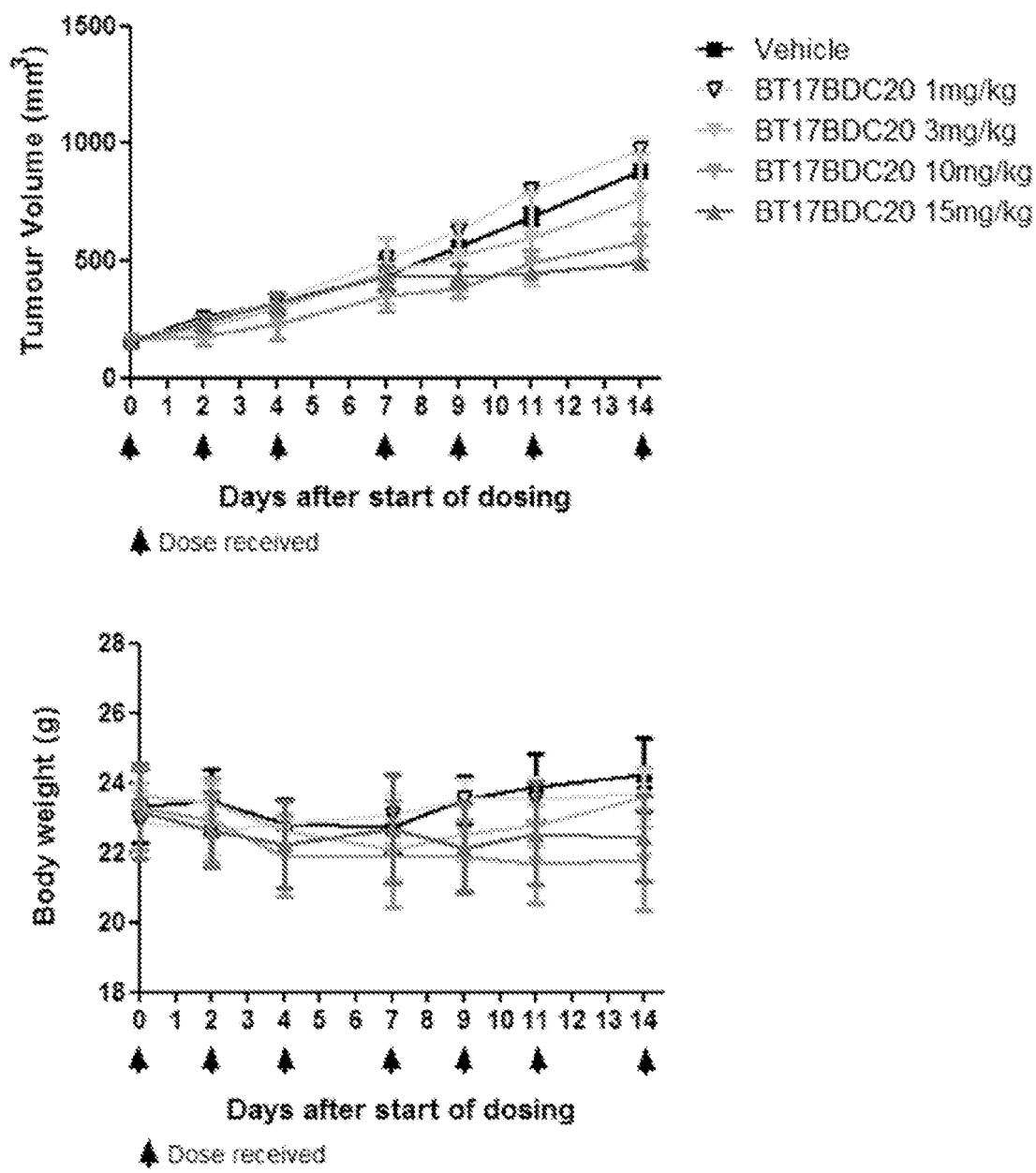
FIG. 12: Top: Plot of mean tumour volume versus time for BT17BDC-20 in EBC-1 xenograft mice. Doses were administered on day 0, 2, 4, 7, 9, 11 and 14. Bottom: Body weight during treatment, which is indicative of drug-associated toxicology and overall animal health.

BT17BDC-17, BT17BDC-18 and BT17BDC-19 were efficacious and cleared tumours in 9 days (FIGS. 9, 10 and 11). BT17BDC-17 showed good efficacy, but some weight reduction at high doses. BT17BDC-20 was, whilst tolerated based on constant weight, not efficacious and only caused a marginal reduction in tumour sizes (FIG. 12).

Figure 13:
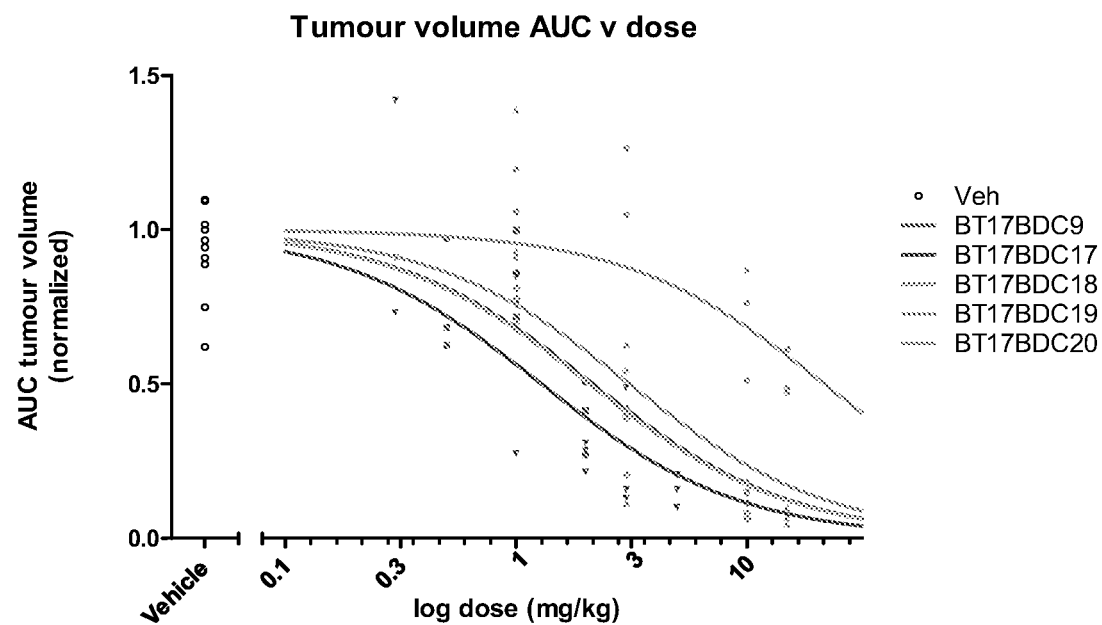
FIG. 13: Plot of the area under the curve (AUC) of tumour volume over time associated with a particular BDC against the corresponding dose group. Curve fits are performed using all available data points normalised for tumour volume at time zero, using standard IC 50 equations.

The area under the curve (AUC) of tumour volume over time and BDC was taken and plotted against the corresponding dose group (FIG. 13). From this, the effective dose to achieve 50% tumour AUC reduction (ED50) can be determined, which is summarised in Table 17.

TABLE 17

Effective dose to achieve 50% tumour AUC reduction for BT17BDC-9, BT17BDC-17, BT17BDC-18, BT17BDC-19 and BT17BDC-20

| BDC | BT17BDC-9 | BT17BDC-17 | BT17BDC-18 | BT17BDC-19 | BT17BDC-20 |
|---|---|---|---|---|---|
| ED50[a] | 2.1 ± 1.1[b] | 1.3 ± 0.6[b] | 2.1 ± 0.8[b] | 3.1 ± 1.6[b] | 22 ± 13[b] |

[a]ED50 ± 95% confidence limit
[b]units in mg/kg, in mouse bearing EBC-1 tumours Thus, BT17BDC-9, BT17BDC-17, BT17BDC-18 and BT17BDC-19 are suitable molecules for use in targeted cancer therapy based on efficacy, and BT17BDC-17, BT17BDC-18 and BT17BDC-19 are well tolerated at efficacious doses.

The invention claimed is:

1. A method of preparing a drug conjugate of formula (IV):

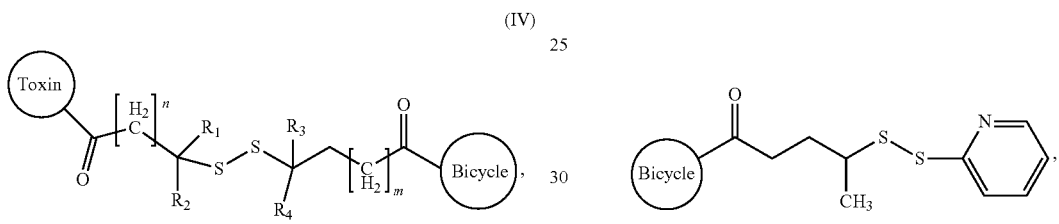

or a salt thereof, wherein:
bicycle represents a peptide ligand specific for MT1-MMP (membrane type 1 metalloprotease) comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein the peptide ligand comprises the amino acid sequence -$C_i$-$X_1$-U/$O_2$-$X_3$-$X_4$-$G_5$-$C_{ii}$-$E_6$-$D_7$-$F_8$-$Y_9$-$X_{10}$-$X_{11}$-$C_{iii}$-(SEQ ID NO: 1), or (β-Ala)-Sar10-AC(D-Ala)NE(1Nal)(D-Ala)CEDFYD(tBuGly)C(SEQ ID NO: 5);

wherein:
$C_i$, $C_{ii}$ and $C_{iii}$ represent first, second and third cysteine residues, respectively;
each of $X_1$, $X_3$, $X_4$, $X_{10}$ and $X_{11}$ represents any amino acid residue;
U/$O_2$ represents that position 2 of the loop sequence between $C_i$ and $C_{ii}$ is U or O;
U represents a polar, uncharged amino acid residue selected from the group consisting of N, C, Q, M, S and T; and
O represents a non-polar aliphatic amino acid residue selected from the group consisting of G, A, I, L, P and V;
toxin is the cytotoxic agent DM1;
$R_3$ represents methyl, and $R_1$, $R_2$ and $R_4$ each represent hydrogen;
m represents 1; and
n represents 1,
the method comprising reacting a compound

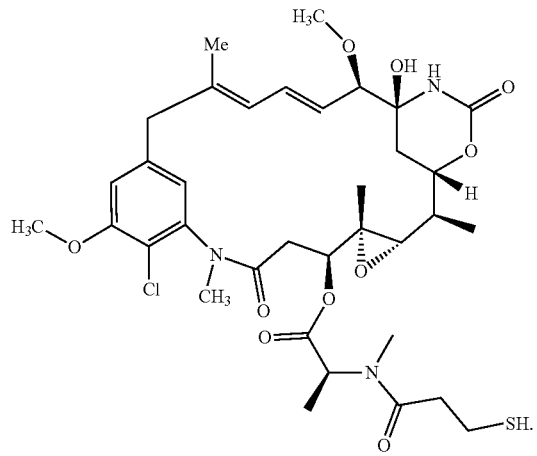

or a salt thereof, with a compound

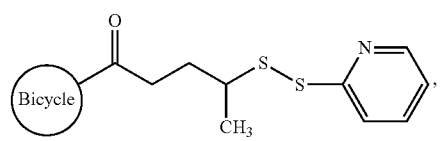

2. The method of claim 1, wherein the compound or a salt thereof, reacts with the compound

[Chemical structure of maytansinoid-SH compound]

in a solution comprising about 50% volume dimethylacetamide, about 50% volume sodium acetate buffer at pH about 5.0, and EDTA.

3. The method of claim 1, wherein $X_1$ is selected from the group consisting of Y, M, F and V.

4. The method of claim 1, wherein $U/O_2$ represents N or G.

5. The method of claim 1, wherein $X_3$ is U or Z, wherein (i) U is selected from the group consisting of N, C, Q, M, S and T, and Z is selected from the group consisting of D and E; or (ii) U is Q and Z is E.

6. The method of claim 1, wherein $X_4$ is selected from the group consisting of F, W and Y.

7. The method of claim 1, wherein $X_{10}$ is selected from the group consisting of D and E; and $X_{11}$ is selected from the group consisting of G, A, I, L, P and V.

8. The method of claim 1, wherein the peptide ligand comprises the amino acid sequence selected from the group consisting of:

-$C_i$-Y-N-E-F-G-$C_{ii}$-E-D-F-Y-D-I-$C_{iii}$-(SEQ ID NO: 2),
βAla-Sar10-A-CYNEFGCEDFYDIC (SEQ ID NO: 3),
C(D-Ala)NEFGCEDFYDIC (SEQ ID NO: 4),
(β-Ala)-Sar10-AC(D-Ala)NE(1Nal)(D-Ala)CEDFYD(tBuGly)C SEQ ID NO: 5),
-$C_i$-Y/M/F/V-U/O-U/Z-J-G-$C_{ii}$-E-D-F-Y-Z-O-$C_{iii}$-(SEQ ID NO: 6),
-$C_i$-Y/M/F/V-N/G-E/Q-F-G-$C_{ii}$-E-D-F-Y-D-I-$C_{iii}$-(SEQ ID NO: 7),
-$C_i$-Y/M/F-N/G-E/Q-F-G-$C_{ii}$-E-D-F-Y-D-I-$C_{iii}$-(SEQ ID NO: 8),
-$C_i$-Y/M-N-E/Q-F-G-$C_{ii}$-E-D-F-Y-D-I-$C_{iii}$-(SEQ ID NO: 9),
-$C_i$-M-N-Q-F-G-$C_{ii}$-E-D-F-Y-D-I-$C_{iii}$-(SEQ ID NO: 10);
-$C_i$-F-G-E-F-G-$C_{ii}$-E-D-F-Y-D-I-$C_{iii}$-(SEQ ID NO: 11);
-$C_i$-V-N-E-F-G-$C_{ii}$-E-D-F-Y-D-I-$C_{iii}$-(SEQ ID NO: 12);
-$C_i$-F-N-E-F-G-$C_{ii}$-E-D-F-Y-D-I-$C_{iii}$-(SEQ ID NO: 13);
-$C_i$-Y-N-E-Y-G-$C_{ii}$-E-D-F-Y-D-I-$C_{iii}$-(SEQ ID NO: 14); and
-$C_i$-Y-N-E-W-G-$C_{ii}$-E-D-F-Y-D-I-$C_{iii}$-(SEQ ID NO: 15).

9. The method of claim 1, wherein the molecular scaffold is TBMB (1,3,5-tris (bromomethyl) benzene), which forms covalent bonds with the cysteine residues of the polypeptide yielding a tri-substituted 1,3,5-trismethylbenzene structure.

10. A method of preparing a drug conjugate of formula (IV):

[Chemical structure of formula (IV) showing Toxin-linker-Bicycle conjugate]

or a salt thereof, wherein:

bicycle represents a peptide ligand comprising:
a polypeptide of the amino acid sequence
(β-Ala)-Sar10-AC(D-Ala)NE(1Nal)(D-Ala)CEDFYD(tBuGly)C (SEQ ID NO: 5); and
a molecular scaffold which is TBMB (1,3,5-tris (bromomethyl) benzene), which forms covalent bonds with the cysteine residues of the polypeptide yielding a tri-substituted 1,3,5-trismethylbenzene structure;

toxin is the cytotoxic agent DM1;

$R_3$ represents methyl, and $R_1$, $R_2$ and $R_4$ each represent hydrogen;

m represents 1; and n represents 1, the method comprising reacting a compound

[Chemical structure showing Bicycle-linker-S-S-pyridyl compound]

or a salt thereof, with a compound

[Chemical structure of maytansinoid-SH compound]

in a solution comprising about 50% volume dimethylacetamide, about 50% volume sodium acetate buffer at pH about 5.0, and EDTA.

11. A compound

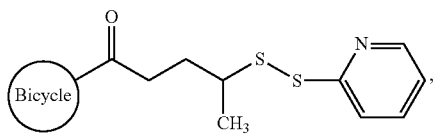

or a salt thereof, wherein bicycle represents a peptide ligand specific for MT1-MMP (membrane type 1 metalloprotease) comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein the peptide ligand comprises the amino acid sequence -$C_i$-$X_1$-U/$O_2$-$X_3$-$X_4$-$G_5$-$C_{ii}$-$E_6$-$D_7$-$F_8$-$Y_9$-$X_{10}$-$X_{11}$-$C_{iii}$-(SEQ ID NO: 1), or (β-Ala)-Sar10-AC(D-Ala)NE(1Nal)(D-Ala)CEDFYD (tBuGly)C SEQ ID NO: 5);

wherein:
$C_i$, $C_{ii}$ and $C_{iii}$ represent first, second and third cysteine residues, respectively;
each of $X_1$, $X_3$, $X_4$, $X_{10}$ and $X_{11}$ represents any amino acid residue;
U/$O_2$ represents that position 2 of the loop sequence between $C_i$ and $C_{ii}$ is U or O;
U represents a polar, uncharged amino acid residue selected from the group consisting of N, C, Q, M, S and T; and
O represents a non-polar aliphatic amino acid residue selected from the group consisting of G, A, I, L, P and V.

12. The compound of claim 11, or a salt thereof, wherein the peptide ligand comprises the amino acid sequence (β-Ala)-Sar10-AC (D-Ala) NE(1Nal) (D-Ala)CEDFYD (tBuGly)C(SEQ ID NO: 5).

13. The compound of claim 11, or a salt thereof, wherein the molecular scaffold is TBMB (1,3,5-tris (bromomethyl) benzene), which forms covalent bonds with the cysteine residues of the polypeptide yielding a tri-substituted 1,3,5-trismethylbenzene structure.

\* \* \* \* \*

SEQUENCE LISTING

```
Sequence total quantity: 80
SEQ ID NO: 1            moltype = AA  length = 14
FEATURE                 Location/Qualifiers
source                  1..14
                        mol_type = protein
                        organism = synthetic construct
VARIANT                 2
                        note = Any amino acid
VARIANT                 3
                        note = N, C, Q, M, S, T, G, A, I, L, P, or V
VARIANT                 4
                        note = Any amino acid
VARIANT                 5
                        note = Any amino acid
VARIANT                 12
                        note = Any amino acid
VARIANT                 13
                        note = Any amino acid
SEQUENCE: 1
CXXXXGCEDF YXXC                                                         14

SEQ ID NO: 2            moltype = AA  length = 14
FEATURE                 Location/Qualifiers
source                  1..14
                        mol_type = protein
                        organism = synthetic construct
SEQUENCE: 2
CYNEFGCEDF YDIC                                                         14

SEQ ID NO: 3            moltype = AA  length = 26
FEATURE                 Location/Qualifiers
source                  1..26
                        mol_type = protein
```

```
                        organism = synthetic construct
SITE                    1
                        note = Beta-alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
SEQUENCE: 3
XXXXXXXXXX XACYNEFGCE DFYDIC                                               26

SEQ ID NO: 4            moltype = AA   length = 14
FEATURE                 Location/Qualifiers
source                  1..14
                        mol_type = protein
                        organism = synthetic construct
SITE                    2
                        note = D-Alanine
SEQUENCE: 4
CANEFGCEDF YDIC                                                            14

SEQ ID NO: 5            moltype = AA   length = 26
FEATURE                 Location/Qualifiers
source                  1..26
                        mol_type = protein
                        organism = synthetic construct
SITE                    1
                        note = Beta-alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
SITE                    14
                        note = D-Alanine
SITE                    17
                        note = 1-naphthylalanine
SITE                    18
                        note = D-Alanine
SITE                    25
                        note = Tert-butylglycine
SEQUENCE: 5
XXXXXXXXXX XACANEXACE DFYDXC                                               26

SEQ ID NO: 6            moltype = AA   length = 14
FEATURE                 Location/Qualifiers
source                  1..14
                        mol_type = protein
                        organism = synthetic construct
```

```
VARIANT                 2
                        note = Y, M, F, or V
VARIANT                 3
                        note = N, C, Q, M, S, T, G, A, I, L, P, or V
VARIANT                 4
                        note = N, C, Q, M, S, or Z
VARIANT                 5
                        note = F, W, or Y
VARIANT                 13
                        note = G, A, I, L, P, or V
SEQUENCE: 6
CXXXXGCEDF YZXC                                                             14

SEQ ID NO: 7            moltype = AA  length = 14
FEATURE                 Location/Qualifiers
source                  1..14
                        mol_type = protein
                        organism = synthetic construct
VARIANT                 2
                        note = Y, M, F, or V
VARIANT                 3
                        note = N or G
VARIANT                 4
                        note = E or Q
SEQUENCE: 7
CXXXFGCEDF YDIC                                                             14

SEQ ID NO: 8            moltype = AA  length = 14
FEATURE                 Location/Qualifiers
source                  1..14
                        mol_type = protein
                        organism = synthetic construct
VARIANT                 2
                        note = Y, M, or F
VARIANT                 3
                        note = N or G
VARIANT                 4
                        note = E or Q
SEQUENCE: 8
CXXXFGCEDF YDIC                                                             14

SEQ ID NO: 9            moltype = AA  length = 14
FEATURE                 Location/Qualifiers
source                  1..14
                        mol_type = protein
                        organism = synthetic construct
VARIANT                 2
                        note = Y or M
VARIANT                 4
                        note = E or Q
SEQUENCE: 9
CXNXFGCEDF YDIC                                                             14

SEQ ID NO: 10           moltype = AA  length = 14
FEATURE                 Location/Qualifiers
source                  1..14
                        mol_type = protein
                        organism = synthetic construct
SEQUENCE: 10
CMNQFGCEDF YDIC                                                             14

SEQ ID NO: 11           moltype = AA  length = 14
FEATURE                 Location/Qualifiers
source                  1..14
                        mol_type = protein
                        organism = synthetic construct
SEQUENCE: 11
CFGEFGCEDF YDIC                                                             14

SEQ ID NO: 12           moltype = AA  length = 14
FEATURE                 Location/Qualifiers
source                  1..14
                        mol_type = protein
                        organism = synthetic construct
SEQUENCE: 12
CVNEFGCEDF YDIC                                                             14

SEQ ID NO: 13           moltype = AA  length = 14
FEATURE                 Location/Qualifiers
```

```
source                  1..14
                        mol_type = protein
                        organism = synthetic construct
SEQUENCE: 13
CFNEFGCEDF YDIC                                                              14

SEQ ID NO: 14           moltype = AA   length = 14
FEATURE                 Location/Qualifiers
source                  1..14
                        mol_type = protein
                        organism = synthetic construct
SEQUENCE: 14
CYNEYGCEDF YDIC                                                              14

SEQ ID NO: 15           moltype = AA   length = 14
FEATURE                 Location/Qualifiers
source                  1..14
                        mol_type = protein
                        organism = synthetic construct
SEQUENCE: 15
CYNEWGCEDF YDIC                                                              14

SEQ ID NO: 16           moltype = AA   length = 15
FEATURE                 Location/Qualifiers
source                  1..15
                        mol_type = protein
                        organism = synthetic construct
SEQUENCE: 16
CKNRGFGCED FYDIC                                                             15

SEQ ID NO: 17           moltype = AA   length = 8
FEATURE                 Location/Qualifiers
source                  1..8
                        mol_type = protein
                        organism = synthetic construct
SEQUENCE: 17
CEDFYDIC                                                                     8

SEQ ID NO: 18           moltype = AA   length = 16
FEATURE                 Location/Qualifiers
source                  1..16
                        mol_type = protein
                        organism = synthetic construct
SEQUENCE: 18
ACYNEFGCED FYDICA                                                            16

SEQ ID NO: 19           moltype = AA   length = 16
FEATURE                 Location/Qualifiers
source                  1..16
                        mol_type = protein
                        organism = synthetic construct
SEQUENCE: 19
ACMNQFGCED FYDICA                                                            16

SEQ ID NO: 20           moltype = AA   length = 26
FEATURE                 Location/Qualifiers
source                  1..26
                        mol_type = protein
                        organism = synthetic construct
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
```

```
SEQUENCE: 20
GXXXXXXXXX XACYNEFGCE DFYDIC                                             26

SEQ ID NO: 21           moltype = AA  length = 4
FEATURE                 Location/Qualifiers
source                  1..4
                        mol_type = protein
                        organism = synthetic construct
SEQUENCE: 21
YNEF                                                                     4

SEQ ID NO: 22           moltype = AA  length = 5
FEATURE                 Location/Qualifiers
source                  1..5
                        mol_type = protein
                        organism = synthetic construct
SEQUENCE: 22
YNEFG                                                                    5

SEQ ID NO: 23           moltype = AA  length = 6
FEATURE                 Location/Qualifiers
source                  1..6
                        mol_type = protein
                        organism = synthetic construct
SEQUENCE: 23
EDFYDI                                                                   6

SEQ ID NO: 24           moltype = AA  length = 14
FEATURE                 Location/Qualifiers
source                  1..14
                        mol_type = protein
                        organism = synthetic construct
SEQUENCE: 24
CCNRWGCEDF YDIC                                                          14

SEQ ID NO: 25           moltype = AA  length = 14
FEATURE                 Location/Qualifiers
source                  1..14
                        mol_type = protein
                        organism = synthetic construct
VARIANT                 2
                        note = Y, W, H, A, M, R, S, G, D, Q, E, L, or T
VARIANT                 4
                        note = E, A, P, D, Q, I, R, Y, F, S, V, H, L, T, M, W, K,
                         or G
VARIANT                 5
                        note = W, Y, or F
SEQUENCE: 25
CXNXXGCEDF YDIC                                                          14

SEQ ID NO: 26           moltype = AA  length = 14
FEATURE                 Location/Qualifiers
source                  1..14
                        mol_type = protein
                        organism = synthetic construct
SEQUENCE: 26
CWNAWGCEDF YDIC                                                          14

SEQ ID NO: 27           moltype = AA  length = 14
FEATURE                 Location/Qualifiers
source                  1..14
                        mol_type = protein
                        organism = synthetic construct
SEQUENCE: 27
CHNPYGCEDF YDIC                                                          14

SEQ ID NO: 28           moltype = AA  length = 14
FEATURE                 Location/Qualifiers
source                  1..14
                        mol_type = protein
                        organism = synthetic construct
SEQUENCE: 28
CANDYGCEDF YDIC                                                          14

SEQ ID NO: 29           moltype = AA  length = 14
FEATURE                 Location/Qualifiers
source                  1..14
                        mol_type = protein
                        organism = synthetic construct
```

```
SEQUENCE: 29
CMNEWGCEDF YDIC                                                             14

SEQ ID NO: 30          moltype = AA  length = 14
FEATURE                Location/Qualifiers
source                 1..14
                       mol_type = protein
                       organism = synthetic construct
SEQUENCE: 30
CANQWGCEDF YDIC                                                             14

SEQ ID NO: 31          moltype = AA  length = 14
FEATURE                Location/Qualifiers
source                 1..14
                       mol_type = protein
                       organism = synthetic construct
SEQUENCE: 31
CRNPWGCEDF YDIC                                                             14

SEQ ID NO: 32          moltype = AA  length = 14
FEATURE                Location/Qualifiers
source                 1..14
                       mol_type = protein
                       organism = synthetic construct
SEQUENCE: 32
CSNIWGCEDF YDIC                                                             14

SEQ ID NO: 33          moltype = AA  length = 14
FEATURE                Location/Qualifiers
source                 1..14
                       mol_type = protein
                       organism = synthetic construct
SEQUENCE: 33
CSNQWGCEDF YDIC                                                             14

SEQ ID NO: 34          moltype = AA  length = 14
FEATURE                Location/Qualifiers
source                 1..14
                       mol_type = protein
                       organism = synthetic construct
SEQUENCE: 34
CGNEYGCEDF YDIC                                                             14

SEQ ID NO: 35          moltype = AA  length = 14
FEATURE                Location/Qualifiers
source                 1..14
                       mol_type = protein
                       organism = synthetic construct
SEQUENCE: 35
CGNRWGCEDF YDIC                                                             14

SEQ ID NO: 36          moltype = AA  length = 14
FEATURE                Location/Qualifiers
source                 1..14
                       mol_type = protein
                       organism = synthetic construct
SEQUENCE: 36
CGNYWGCEDF YDIC                                                             14

SEQ ID NO: 37          moltype = AA  length = 14
FEATURE                Location/Qualifiers
source                 1..14
                       mol_type = protein
                       organism = synthetic construct
SEQUENCE: 37
CMNEYGCEDF YDIC                                                             14

SEQ ID NO: 38          moltype = AA  length = 14
FEATURE                Location/Qualifiers
source                 1..14
                       mol_type = protein
                       organism = synthetic construct
SEQUENCE: 38
CSNPWGCEDF YDIC                                                             14

SEQ ID NO: 39          moltype = AA  length = 14
FEATURE                Location/Qualifiers
source                 1..14
                       mol_type = protein
```

```
                              organism = synthetic construct
SEQUENCE: 39
CDNAWGCEDF YDIC                                                     14

SEQ ID NO: 40              moltype = AA   length = 14
FEATURE                    Location/Qualifiers
source                     1..14
                           mol_type = protein
                           organism = synthetic construct
SEQUENCE: 40
CHNAWGCEDF YDIC                                                     14

SEQ ID NO: 41              moltype = AA   length = 14
FEATURE                    Location/Qualifiers
source                     1..14
                           mol_type = protein
                           organism = synthetic construct
SEQUENCE: 41
CQNYWGCEDF YDIC                                                     14

SEQ ID NO: 42              moltype = AA   length = 14
FEATURE                    Location/Qualifiers
source                     1..14
                           mol_type = protein
                           organism = synthetic construct
SEQUENCE: 42
CSNQYGCEDF YDIC                                                     14

SEQ ID NO: 43              moltype = AA   length = 14
FEATURE                    Location/Qualifiers
source                     1..14
                           mol_type = protein
                           organism = synthetic construct
SEQUENCE: 43
CANQYGCEDF YDIC                                                     14

SEQ ID NO: 44              moltype = AA   length = 14
FEATURE                    Location/Qualifiers
source                     1..14
                           mol_type = protein
                           organism = synthetic construct
SEQUENCE: 44
CGNAYGCEDF YDIC                                                     14

SEQ ID NO: 45              moltype = AA   length = 14
FEATURE                    Location/Qualifiers
source                     1..14
                           mol_type = protein
                           organism = synthetic construct
SEQUENCE: 45
CSNFWGCEDF YDIC                                                     14

SEQ ID NO: 46              moltype = AA   length = 14
FEATURE                    Location/Qualifiers
source                     1..14
                           mol_type = protein
                           organism = synthetic construct
SEQUENCE: 46
CHNQYGCEDF YDIC                                                     14

SEQ ID NO: 47              moltype = AA   length = 14
FEATURE                    Location/Qualifiers
source                     1..14
                           mol_type = protein
                           organism = synthetic construct
SEQUENCE: 47
CYNSYGCEDF YDIC                                                     14

SEQ ID NO: 48              moltype = AA   length = 14
FEATURE                    Location/Qualifiers
source                     1..14
                           mol_type = protein
                           organism = synthetic construct
SEQUENCE: 48
CENAWGCEDF YDIC                                                     14

SEQ ID NO: 49              moltype = AA   length = 14
FEATURE                    Location/Qualifiers
source                     1..14
```

-continued

```
                        mol_type = protein
                        organism = synthetic construct
SEQUENCE: 49
CANYWGCEDF YDIC                                                          14

SEQ ID NO: 50           moltype = AA   length = 14
FEATURE                 Location/Qualifiers
source                  1..14
                        mol_type = protein
                        organism = synthetic construct
SEQUENCE: 50
CGNDWGCEDF YDIC                                                          14

SEQ ID NO: 51           moltype = AA   length = 14
FEATURE                 Location/Qualifiers
source                  1..14
                        mol_type = protein
                        organism = synthetic construct
SEQUENCE: 51
CANRFGCEDF YDIC                                                          14

SEQ ID NO: 52           moltype = AA   length = 14
FEATURE                 Location/Qualifiers
source                  1..14
                        mol_type = protein
                        organism = synthetic construct
SEQUENCE: 52
CRNAWGCEDF YDIC                                                          14

SEQ ID NO: 53           moltype = AA   length = 14
FEATURE                 Location/Qualifiers
source                  1..14
                        mol_type = protein
                        organism = synthetic construct
SEQUENCE: 53
CGNVFGCEDF YDIC                                                          14

SEQ ID NO: 54           moltype = AA   length = 14
FEATURE                 Location/Qualifiers
source                  1..14
                        mol_type = protein
                        organism = synthetic construct
SEQUENCE: 54
CSNHWGCEDF YDIC                                                          14

SEQ ID NO: 55           moltype = AA   length = 14
FEATURE                 Location/Qualifiers
source                  1..14
                        mol_type = protein
                        organism = synthetic construct
SEQUENCE: 55
CENEYGCEDF YDIC                                                          14

SEQ ID NO: 56           moltype = AA   length = 14
FEATURE                 Location/Qualifiers
source                  1..14
                        mol_type = protein
                        organism = synthetic construct
SEQUENCE: 56
CANFWGCEDF YDIC                                                          14

SEQ ID NO: 57           moltype = AA   length = 14
FEATURE                 Location/Qualifiers
source                  1..14
                        mol_type = protein
                        organism = synthetic construct
SEQUENCE: 57
CGNLWGCEDF YDIC                                                          14

SEQ ID NO: 58           moltype = AA   length = 14
FEATURE                 Location/Qualifiers
source                  1..14
                        mol_type = protein
                        organism = synthetic construct
SEQUENCE: 58
CLNQYGCEDF YDIC                                                          14

SEQ ID NO: 59           moltype = AA   length = 14
FEATURE                 Location/Qualifiers
```

```
                        -continued source                  1..14
                        mol_type = protein
                        organism = synthetic construct
SEQUENCE: 59
CYNHFGCEDF YDIC                                                         14

SEQ ID NO: 60           moltype = AA   length = 14
FEATURE                 Location/Qualifiers
source                  1..14
                        mol_type = protein
                        organism = synthetic construct
SEQUENCE: 60
CYNTFGCEDF YDIC                                                         14

SEQ ID NO: 61           moltype = AA   length = 14
FEATURE                 Location/Qualifiers
source                  1..14
                        mol_type = protein
                        organism = synthetic construct
SEQUENCE: 61
CANDFGCEDF YDIC                                                         14

SEQ ID NO: 62           moltype = AA   length = 14
FEATURE                 Location/Qualifiers
source                  1..14
                        mol_type = protein
                        organism = synthetic construct
SEQUENCE: 62
CSNMWGCEDF YDIC                                                         14

SEQ ID NO: 63           moltype = AA   length = 14
FEATURE                 Location/Qualifiers
source                  1..14
                        mol_type = protein
                        organism = synthetic construct
SEQUENCE: 63
CRNWWGCEDF YDIC                                                         14

SEQ ID NO: 64           moltype = AA   length = 14
FEATURE                 Location/Qualifiers
source                  1..14
                        mol_type = protein
                        organism = synthetic construct
SEQUENCE: 64
CSNLWGCEDF YDIC                                                         14

SEQ ID NO: 65           moltype = AA   length = 14
FEATURE                 Location/Qualifiers
source                  1..14
                        mol_type = protein
                        organism = synthetic construct
SEQUENCE: 65
CRNDWGCEDF YDIC                                                         14

SEQ ID NO: 66           moltype = AA   length = 14
FEATURE                 Location/Qualifiers
source                  1..14
                        mol_type = protein
                        organism = synthetic construct
SEQUENCE: 66
CLNRWGCEDF YDIC                                                         14

SEQ ID NO: 67           moltype = AA   length = 14
FEATURE                 Location/Qualifiers
source                  1..14
                        mol_type = protein
                        organism = synthetic construct
SEQUENCE: 67
CMNDWGCEDF YDIC                                                         14

SEQ ID NO: 68           moltype = AA   length = 14
FEATURE                 Location/Qualifiers
source                  1..14
                        mol_type = protein
                        organism = synthetic construct
SEQUENCE: 68
CRNSYGCEDF YDIC                                                         14

SEQ ID NO: 69           moltype = AA   length = 14
```

```
FEATURE              Location/Qualifiers
source               1..14
                     mol_type = protein
                     organism = synthetic construct
SEQUENCE: 69
CSNEFGCEDF YDIC                                                              14

SEQ ID NO: 70        moltype = AA  length = 14
FEATURE              Location/Qualifiers
source               1..14
                     mol_type = protein
                     organism = synthetic construct
SEQUENCE: 70
CGNPWGCEDF YDIC                                                              14

SEQ ID NO: 71        moltype = AA  length = 14
FEATURE              Location/Qualifiers
source               1..14
                     mol_type = protein
                     organism = synthetic construct
SEQUENCE: 71
CRNKWGCEDF YDIC                                                              14

SEQ ID NO: 72        moltype = AA  length = 14
FEATURE              Location/Qualifiers
source               1..14
                     mol_type = protein
                     organism = synthetic construct
SEQUENCE: 72
CGNLFGCEDF YDIC                                                              14

SEQ ID NO: 73        moltype = AA  length = 14
FEATURE              Location/Qualifiers
source               1..14
                     mol_type = protein
                     organism = synthetic construct
SEQUENCE: 73
CQNRYGCEDF YDIC                                                              14

SEQ ID NO: 74        moltype = AA  length = 14
FEATURE              Location/Qualifiers
source               1..14
                     mol_type = protein
                     organism = synthetic construct
SEQUENCE: 74
CRNLWGCEDF YDIC                                                              14

SEQ ID NO: 75        moltype = AA  length = 14
FEATURE              Location/Qualifiers
source               1..14
                     mol_type = protein
                     organism = synthetic construct
SEQUENCE: 75
CGNLYGCEDF YDIC                                                              14

SEQ ID NO: 76        moltype = AA  length = 14
FEATURE              Location/Qualifiers
source               1..14
                     mol_type = protein
                     organism = synthetic construct
SEQUENCE: 76
CGNGYGCEDF YDIC                                                              14

SEQ ID NO: 77        moltype = AA  length = 14
FEATURE              Location/Qualifiers
source               1..14
                     mol_type = protein
                     organism = synthetic construct
SEQUENCE: 77
CTNRWGCEDF YDIC                                                              14

SEQ ID NO: 78        moltype = AA  length = 14
FEATURE              Location/Qualifiers
source               1..14
                     mol_type = protein
                     organism = synthetic construct
SEQUENCE: 78
CYNLWGCEDF YDIC                                                              14
```

-continued

```
SEQ ID NO: 79          moltype = AA  length = 6
FEATURE                Location/Qualifiers
source                 1..6
                       mol_type = protein
                       organism = synthetic construct
SEQUENCE: 79
HHHHHH                                                                         6

SEQ ID NO: 80          moltype = AA  length = 14
FEATURE                Location/Qualifiers
source                 1..14
                       mol_type = protein
                       organism = synthetic construct
SITE                   1
                       note = Acetylated residue
SEQUENCE: 80
CYNEFGCEDF YDIC                                                               14
```